(12) United States Patent
Misharin

(10) Patent No.: US 11,412,943 B2
(45) Date of Patent: *Aug. 16, 2022

(54) METHODS AND SYSTEMS FOR OBTAINING PHYSIOLOGIC INFORMATION

(71) Applicant: Olesya Chornoguz, North Wales, PA (US)

(72) Inventor: Alexander Misharin, North Wales, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/222,031

(22) Filed: Apr. 5, 2021

(65) Prior Publication Data

US 2021/0219855 A1 Jul. 22, 2021

Related U.S. Application Data

(63) Continuation-in-part of application No. 17/153,851, filed on Jan. 20, 2021, which is a continuation of application No. 15/650,850, filed on Jul. 15, 2017, now Pat. No. 10,925,496.

(60) Provisional application No. 63/005,371, filed on Apr. 5, 2020, provisional application No. 62/363,230, filed on Jul. 16, 2016.

(51) Int. Cl.
| | |
|---|---|
| A61B 5/024 | (2006.01) |
| A61B 5/00 | (2006.01) |
| G06T 7/00 | (2017.01) |
| A61B 5/08 | (2006.01) |
| G06T 7/246 | (2017.01) |

(52) U.S. Cl.
CPC ........ *A61B 5/02405* (2013.01); *A61B 5/0077* (2013.01); *A61B 5/0082* (2013.01); *A61B 5/024* (2013.01); *A61B 5/0816* (2013.01); *G06T 7/0012* (2013.01); *G06T 7/246* (2017.01); *A61B 2562/04* (2013.01); *G06T 2207/10016* (2013.01); *G06T 2207/10048* (2013.01); *G06T 2207/20056* (2013.01); *G06T 2207/30048* (2013.01); *G06T 2207/30196* (2013.01)

(58) Field of Classification Search
CPC . A61B 5/02405; A61B 5/0077; A61B 5/0082; G06T 7/0012; G06T 2207/30048
USPC .......................................................... 348/77
See application file for complete search history.

(56) References Cited

U.S. PATENT DOCUMENTS

| | | | |
|---|---|---|---|
| 5,249,163 | A | 9/1993 | Erickson |
| 6,352,517 | B1 | 3/2002 | Flock |

(Continued)

OTHER PUBLICATIONS

Chen J., Chang Z., Qiu Q., Li X., Sapiro G., Bronstein A., Pietikäinen M. "RealSense = Real Heart Rate: Illumination Invariant Heart Rate Estimation from Videos", 6th International Conference on Image Processing Theory Tools and Applications (IPTA), Dec. 12-15, 2016, Oulu, Finland, DOI: doi.org/10.1109/IPTA.2016.7820970; 6 pages.

(Continued)

*Primary Examiner* — On S Mung

(57) ABSTRACT

Methods and systems suitable for obtaining information related to at least one of: respiration rate, heart rate, respiration rate variability, heart rate variability, temporal characteristics of at least a part of a heartbeat, temporal characteristics of at least a part of a respiration cycle, or a duration of a time interval of propagation of a blood pressure pulse from a first point or area or part of a body to a second point or area or part of the body, in a non-contact fashion.

20 Claims, 24 Drawing Sheets

(56) References Cited

U.S. PATENT DOCUMENTS

| | | |
|---|---|---|
| 7,477,571 B2 | 1/2009 | Melese |
| 8,149,273 B2 | 4/2012 | Liu |
| 8,553,940 B2 | 10/2013 | Kirenko |
| 8,693,735 B2 | 4/2014 | Kielkopf |
| 8,792,969 B2 | 7/2014 | Bernal |
| 8,838,209 B2 | 9/2014 | Mestha |
| 8,855,384 B2 | 10/2014 | Kyal |
| 8,897,522 B2 | 11/2014 | Mestha |
| 8,971,985 B2 | 3/2015 | Bernal |
| 9,204,824 B2 | 12/2015 | Lasenby |
| 9,204,825 B2 | 12/2015 | Lasenby |
| 9,226,691 B2 | 1/2016 | Bernal |
| 9,262,826 B2 | 2/2016 | Khachaturian |
| 9,265,456 B2 | 2/2016 | Kirenko |
| 9,301,710 B2 | 4/2016 | Mestha |
| 9,305,350 B2 | 4/2016 | Crawley |
| 9,324,144 B2 | 4/2016 | Khachaturian |
| 9,339,215 B2 | 5/2016 | Van Vugt |
| 9,351,649 B2 | 5/2016 | Mestha |
| 9,364,157 B2 | 6/2016 | Lu |
| 9,636,041 B2 | 5/2017 | Zalevsky |
| 9,704,266 B2 | 7/2017 | Hay |
| 9,854,976 B2 | 1/2018 | Takamori |
| 9,892,505 B2 | 2/2018 | Redtel |
| 9,922,420 B2 | 3/2018 | Wang |
| 10,108,325 B2 | 10/2018 | Hay |
| 10,213,117 B2 | 2/2019 | Lading |
| 10,240,912 B2 | 3/2019 | Muijs |
| 10,292,662 B2 | 5/2019 | Kirenko |
| 10,335,045 B2 | 7/2019 | Sebe |
| 10,349,894 B2 | 7/2019 | Shan |
| 10,352,762 B2 | 7/2019 | Carmon |
| 10,459,615 B2 | 10/2019 | Hay |
| 10,521,098 B2 | 12/2019 | Hay |
| 10,602,971 B2 | 3/2020 | Satoi |
| 10,624,586 B2 | 4/2020 | Noguchi |
| 10,709,342 B2 | 7/2020 | Amelard |
| 10,776,920 B2 | 9/2020 | Linard |
| 10,939,833 B2 | 3/2021 | Khwaja |
| 2011/0142316 A1* | 6/2011 | Wang ............... G06T 11/006 382/131 |
| 2011/0251493 A1 | 10/2011 | Poh |
| 2013/0324875 A1* | 12/2013 | Mestha ............... G06T 7/262 600/534 |
| 2014/0072190 A1 | 3/2014 | Wu |
| 2014/0276104 A1 | 9/2014 | Tao |
| 2015/0257653 A1 | 9/2015 | Hyde |
| 2015/0342535 A1 | 12/2015 | Chen |
| 2016/0217588 A1 | 7/2016 | Hay |
| 2016/0278644 A1 | 9/2016 | He |
| 2017/0055878 A1 | 3/2017 | Chon |
| 2019/0000391 A1 | 1/2019 | De Haan |
| 2019/0082972 A1 | 3/2019 | Tao |
| 2019/0167118 A1 | 6/2019 | Vilenskii |
| 2020/0121262 A1 | 4/2020 | De Haan |
| 2022/0039679 A1 | 2/2022 | Califa |

OTHER PUBLICATIONS

Nakajima K., Osa A., Miike H. "A method for measuring respiration and physical activity in bed by optical flow analysis" in Proceedings of the 19th Annual International Conference of the IEEE Engineering in Medicine and Biology Society, Oct. 30-Nov. 2, 1997, Chicago, IL, USA, vol. 5, pp. 2054-2057, DOI: doi.org/10.1109/IEMBS.1997.758752.

Nakajima K., Matsumoto Y., Tamura T. "Development of real-time image sequence analysis for evaluating posture change and respiratory rate of a subject in bed", Physiological Measurement, 2001, vol. 22, No. 3, pp. N21-N28, DOI: doi.org/10.1088/0967-3334/22/3/401.

Kuo Y.-M., Lee J.-S., Chung P.-C. "A Visual Context-Awareness-Based Sleeping-Respiration Measurement System", IEEE Transactions on Information Technology in Biomedicine, 2010, vol. 14, issue 2, pp. 255-265, DOI: doi.org/10.1109/TITB.2009.2036168.

* cited by examiner

METHODS AND SYSTEMS FOR OBTAINING PHYSIOLOGIC INFORMATION

RELATED APPLICATIONS

This application is a continuation-in-part of the U.S. application Ser. No. 17/153,851 filed on Jan. 20, 2021 which is a continuation of the U.S. application Ser. No. 15/650,850 filed on Jul. 15, 2017 that claims priority from the U.S. provisional patent application No. 62/363,230 filed on Jul. 16, 2016. This application further claims priority from the U.S. provisional patent application No. 63/005,371 filed on Apr. 5, 2020. The U.S. application Ser. Nos. 17/153,851, 15/650,850 as well as the U.S. provisional patent applications No. 62/363,230 and No. 63/005,371 are incorporated herein by reference in their entirety.

BACKGROUND OF THE INVENTION

Information related to pulse, respiration and other processes (e.g., physiologic ones) in the body of a person is typically obtained using various contact devices and methods. Certain contactless approaches are available as well including the ones that use video cameras.

DETAILED DESCRIPTION OF THE INVENTION

Figure 1:
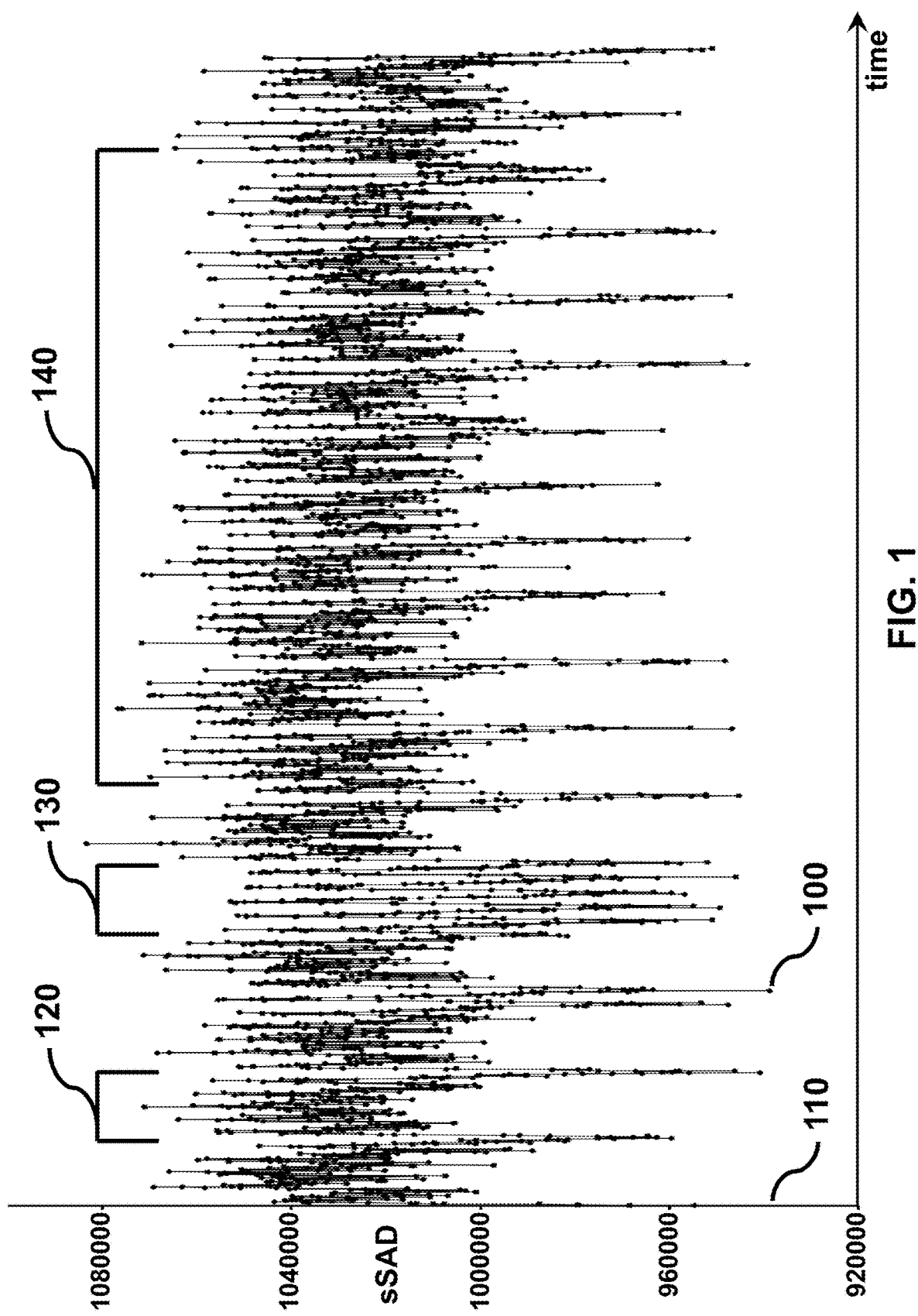
FIG. 1 shows example data obtained using an example embodiment of a system and an example implementation of a method according to the technology disclosed in this patent document.

An ability to obtain information related to pulse, respiration and other processes (e.g., physiologic ones) in the body of a person (the term "person" herein generally refers to an adult person, a child, an infant/baby, and/or a fetus inside a body of a female/mother) in a non-contact fashion can find applications in the fields of sleep medicine, cardiology, maternal-fetal medicine and in situations when direct contact with the person for the purpose of obtaining such measurements is either undesirable or not possible.

The present patent document discloses devices, systems and methods suitable for obtaining, in a non-contact fashion, information related to at least one physiologic parameter of a person such as, for example, respiration rate, heart rate, respiration rate variability, heart rate variability, temporal characteristics of at least a part of a heartbeat, temporal characteristics of at least a part of a respiration cycle, or a (numeric value of) duration (or length or span) of a time interval of propagation of a blood pressure pulse (or a blood pressure wave; or a blood pulse; or a blood wave) from a first point or area or part of a body to a second point or area or part of the body (also referred to as pulse wave transit time), among others. The physiologic parameters mentioned above are referred to, for example, as the "physiologic parameters" or the "group of physiologic parameters" below; any individual physiologic parameter in the said physiologic parameters is referred to as a/the physiologic parameter below.

The duration of the time interval of the blood pressure wave propagation between the first point of the body (e.g., a human body) and the second point of the body determined according to the disclosed technology can be used to determine or obtain pulse wave velocity (PWV) of the blood pressure wave propagation by dividing the duration of the time interval by a distance between the first point and the second point. For example, the distance can be a length of a straight line between the points or a length of a path (real or virtual) between the points. One or more of the obtained PWV numeric value(s) can be further used to obtain a numeric value related to blood pressure (systolic and/or diastolic) of the person.

For example, the methods, devices and systems for non-contact monitoring of physiologic parameters disclosed in this patent document can find applications in the areas of respiration and/or pulse gating for medical imaging (e.g., magnetic resonance imaging (MRI), X-ray computed tomography, etc.), sleep studies for non-contact monitoring of any of the above-mentioned physiologic parameters during sleep of a person, non-contact monitoring of mechanical activity of a heart of an adult person as well as of a fetus in a mother's womb, and in other application areas.

Three key elements of a system according to the technology disclosed in this patent document are: 1) a light source element which main function in the system is to illuminate one or more areas (or parts; referred to as a set of areas (or a set of parts) in this patent document) of a person's body, wherein the areas may be at least partially covered (e.g., by a cloth or an item of clothing or a blanket or any other covering item or items); 2) a video camera element which main function in the system is to collect one or more video frames (referred to as a set of video frames or video frames set in this patent document) capturing at least a part of the areas illuminated by the light source of the system; and 3) a computing element which main function in the system is to perform computations for at least a part of the video frames set. The system elements and their function are described in greater details below. We assume that a body of a person or a part of the person's body or any number of areas of the person's body can be either covered completely or covered partially or not covered at all when we make references to "a body of a person", "a person's body", "a part of a person's body", "an area of a person's body", "one or more areas of a person's body", "a set of areas of a person's body", "two areas of a person's body", "any number of areas of a person's body" and the like below, including the Claims of the present patent document. Also, when an area of a body is covered (partially or completely by any number of any covering items), phrases like "a light source is illuminating the area" or "a light source is projecting light on the area" or "a light source is creating (or projecting) light spots on the area" or "a light source is creating elements of a light texture on the area" and the like assume that the light source can illuminate or create light spots etc. on the said items covering the area of the body (e.g., an area of skin of the body) and/or on the parts of the area of the body which are not covered by the covering items.

Video frame is generally defined herein as one or more numeric values (also referred to as a set or a group or an array of numeric values in this patent document) corresponding to one or more pixels (or sensing elements, or areas; referred to as a set of pixels in this patent document; e.g., physical pixels and/or virtual pixels each of which many be a combination of one or more physical pixels) of a video sensor (e.g., a video sensor of a video camera; for example, a video sensor of a video camera of a system or a device according to the disclosed technology); the set of pixels of the video sensor can be however large or small, ranging from all the sensor pixels (the whole sensor) to a single pixel of the sensor. Terms that can be used instead of the "pixel" of a video sensor include, for example, "photosite", "sensel", "photosensor element", "sensing element", "sensing area", or "area" of the video sensor (or, generally, of a light sensor or a light detector). The set of numeric values corresponding to or contained in a video frame (video frame data of the video frame) can have more than one numeric value corresponding to the same pixel of a video sensor. For example, the set of numeric values can include an array of numeric values (e.g., the array can include more than one numeric value) corresponding to a pixel of the video sensor. Pixel of a video frame is generally defined herein as one or more numeric values corresponding to a single pixel of a video sensor (e.g., the pixel of the video sensor can be a physical pixel or a physical sensing element or a physical sensing area of the sensor and/or it can be a virtual pixel which can include a combination of one or more physical pixels of the sensor each of which can have any physical location within the sensor as well as any size and/or any internal structure). The pixel of a video frame is (typically) contained in the video frame data of the video frame. For example, a pixel of a video frame can include numeric values corresponding to intensities of color components such as red, green, and blue, or cyan, magenta, yellow, and black. For example, each of the red, green, or blue intensity values of the pixel can correspond to a "red", "green", or "blue" pixel or element of a video sensor that was used to produce the video frame containing the pixel. Similarly to the way that pixels of a physical video sensor (or, more generally, a light sensor or a light detector) can be arranged, for example, as a two-dimensional array or a matrix of pixels having a number of rows and a number of columns, numeric values of a video frame (or numeric values that are contained in, correspond to, or associated with a video frame; or numeric values of video frame data of the video frame) can be included in or contained in various data structures or arranged using various data structures including but not limited to one-dimensional arrays (or sets or collections, etc.), two-dimensional arrays or arrays having a dimension larger than two, as well as trees, lists and any other types of data structures. By "an area of a video frame" or "a part of a video frame" or "a section of a video frame" in this patent document we generally mean an area or a part or a section of an image captured in the video frame (as, for example, that image or its area or its part or its section could be viewed by a person) and/or a part of the video frame data of the video frame that corresponds to the part or the area or the section of the image.

The main effect of a light source element and of its function according to the technology disclosed in this patent document is to impart an additional (additional to the present or non-present ambient (natural or artificial) light) light texture to one or more objects around the light source element (e.g., to a part of a person's body). We term the additional light texture the "artificial light texture" or the "ALT". The additional light texture produced by the light source element is preferably characterized by having one or more distinct illumination areas which we term its "elements". For example, one or more light spots (also referred to as a set of light spots in this patent document) created by a light source element of a system according to the disclosed technology on one or more areas of a person's body form the said artificial light texture with each individual light spot being its element. A light spot created by a light source element of a system according to the disclosed technology is, generally, illumination produced by the light source element on an area of an object such that the area of the object having the light spot is generally surrounded by areas that are either not illuminated by the light source or that have levels of illumination produced by the light source that are lower (e.g., in some cases significantly lower) compared to the level of illumination produced by the light source element on the area having the light spot. If the light source element is the only source of light in a scene, then the light spots produced by the light source element on surfaces of objects around the element would look (to a person observing the scene or in an image of the scene obtained by a (video or photo) camera) like illuminated (e.g., bright) areas surrounded by darker (or, in some cases, completely dark) areas. So, a light spot can also refer to an area (for example, an area of an object illuminated by the light source element or an area of a video frame that captured the object illuminated by the light source element) in which illumination is produced by the light source element, wherein the area can be (at least partially) surrounded by or be next to (or proximate to) other areas which have lower levels of illumination produced by the light source element. The level of illumination (or, generally, the level of electromagnetic radiation) that is produced by the light source element on the area covered by a light spot created by the light source element (or within the light spot) can be measured or characterized using, for example, irradiance or illuminance or any other measure of a flux or level of electromagnetic radiation on the surface (or through the surface) covered by the light spot as well as, for example, using spatial distribution of irradiance or spatial distribution of illuminance of light from the light source element on the area covered by the light spot. For example, irradiance of light from the light source element on the area covered by the light spot can have a uniform spatial distribution. For example, irradiance of light from the light source element on the area covered by the light spot can have a normal (or Gaussian) spatial distribution. For example, irradiance of light from the light source element on the area covered by the light spot can have an irregular spatial distribution. For example, irradiance of light from the light source element on the area covered by the light spot can have a random spatial distribution. For example, irradiance of light from the light source element on the area covered by the light spot can have a repeating pattern of spatial distribution at least on a part of the light spot. A light spot can have any shape. For example, the light spot can have an essentially circular shape or an essentially elliptical shape or an essentially rectangular shape or an arbitrary shape or an amorphous shape. Illumination of areas of a person's body by the light source element of a system according to the disclosed technology (e.g., through creating one or more light spots on those areas (or on each of those areas)) can lead to creating or increasing illumination of the areas (or on the areas) relative to other areas of the person's body (which can be described as creating or increasing illumination contrast between the areas illuminated by the light source element relative to the areas that are not illuminated by the light source element), as, for example, observed in video frames captured by a video camera element of a system according to the disclosed technology (the illumination or the illumination contrast can be measured, for example, using video frame data as, for example, described below). Such illumination creates elements of the additional light texture (each of the illuminated areas is an element of the additional light texture).

Figure 9:
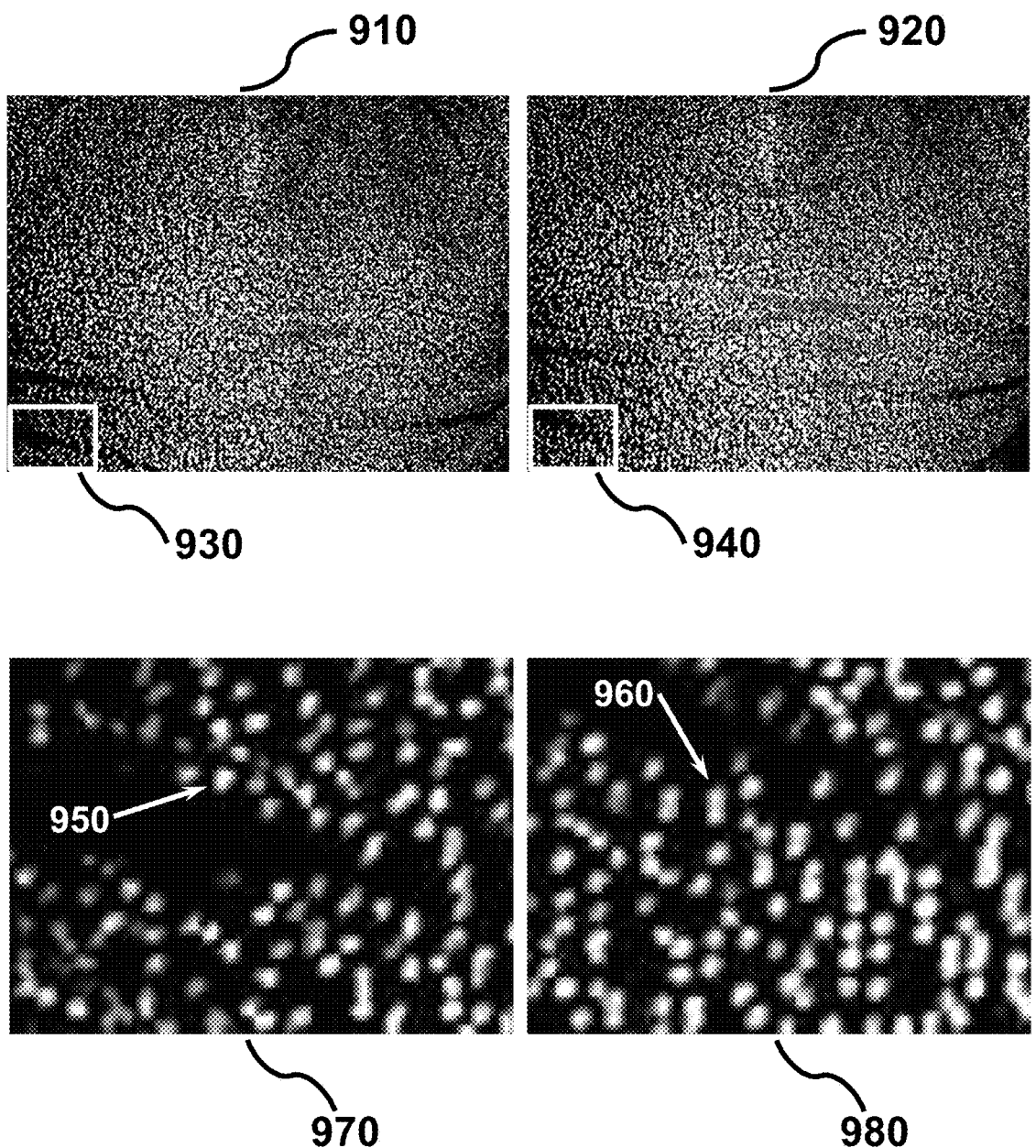
FIG. 9 shows example variations of the elements of the additional light texture associated with the respiration and/or pulse of a person.
Figure 10:
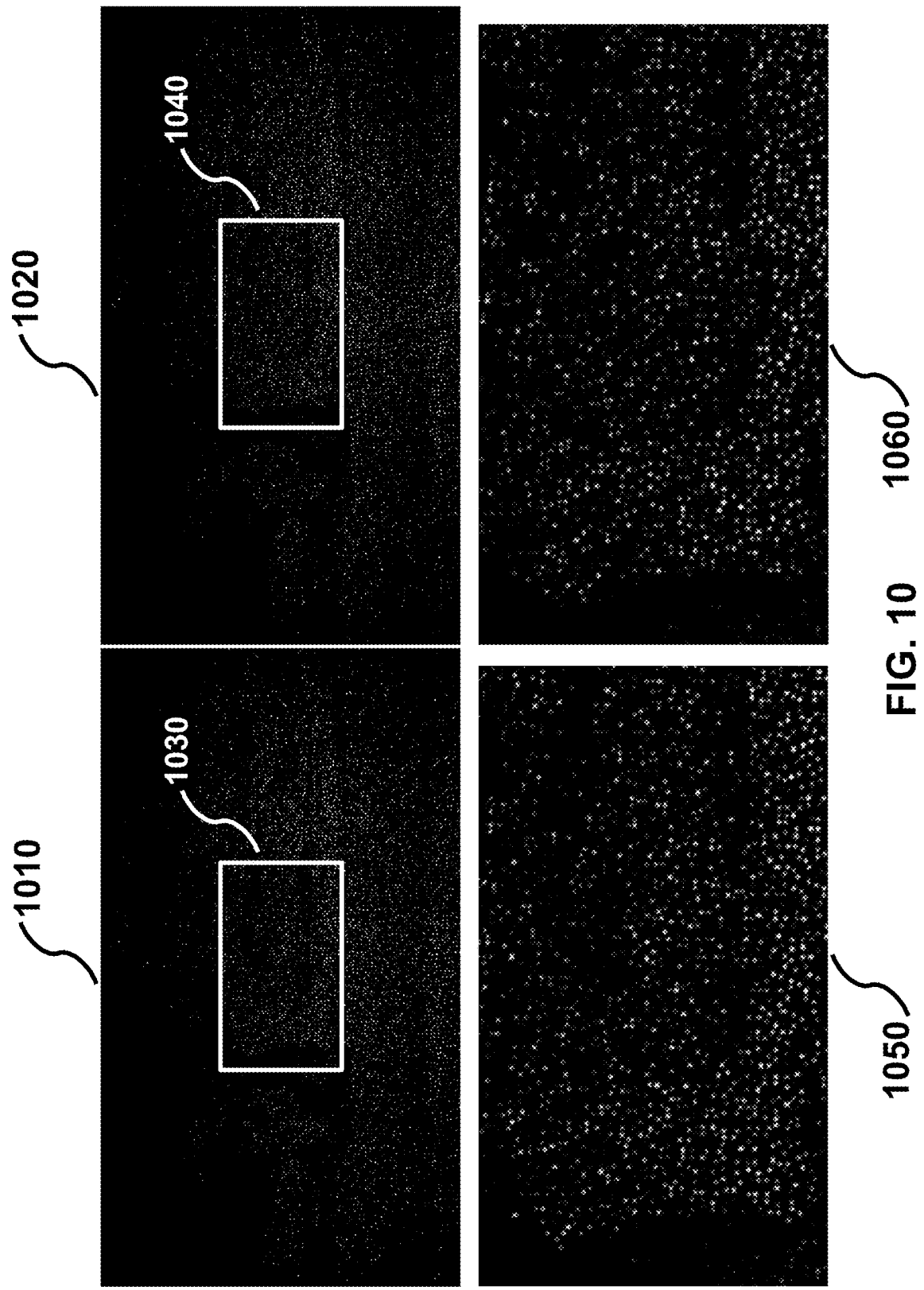
FIG. 10 shows other example variations of the elements of the additional light texture associated with the respiration and/or pulse of a person.

Movements of the body of a person, including those which are related to the person's respiration and/or heartbeats, can lead to a change or a sequence of changes or variations in a curvature and/or shape and/or position and/or tilt and/or size of one or more surfaces of the person's body parts and/or of any of the items which might be covering the person's body, which, in turn, can lead to variations in one or more of illumination, shape, size, location (or position) of one or more elements of the additional light texture produced by a light source on the said surfaces and/or to a variation in a distribution of illumination within an element of the additional light texture or to a variation in a distribution of illumination among the elements of the additional light texture and/or to a variation in a distribution of shapes of the elements of the additional light texture and/or to a variation in a distribution of sizes of the elements of the additional light texture and/or to a variation in a distribution of locations (or positions) of the elements of the additional light texture and/or to a variation in the number of those elements, as observed by a video camera element (as captured in video frames collected by the video camera element) of a system according to the disclosed technology (see, e.g., FIGS. 9 and 10 and the related description below). The said variations are captured, at least in part, by the video camera element in a set of video frames which (video frames) are processed (subsequently to or in parallel with the video frames capture) by a computing element according to a method according to the technology disclosed in this patent document to result in one or more numeric values (also referred to as a set of numeric values), referred to as the "ALT data" in this patent document, wherein the ALT data can be further processed to obtain numeric values related to or representative of the information relevant to the said at least one physiologic parameter of the person and/or the ALT data can be processed to display at least a part of the ALT data using a graphical representation such as, for example, a 2D plot or a 3D plot or an alphanumeric representation or using an audio-based representation.

Application of the additional light texture can greatly increase illumination contrast (contrast between levels of illumination of different areas or objects) in the scene observed by a video camera, especially in a low ambient light environment such as, for example, the one that is typically present during nighttime. As we demonstrate below, the additional light texture can play a role of an amplification medium for small body movements and its application to a person's body can lead to orders of magnitude increase in the components of the ALT data that are related to the heart activity and/or respiration of the person compared to the case when there is no additional light texture present (e.g. when the ALT-generating light element is switched off) during the otherwise equivalent data collection and data processing procedures and under the otherwise equivalent conditions (see FIGS. 3A-3C and the related description below).

The additional light texture created by a light source element can cover parts of the objects which are in contact (direct or via other objects) with the person's body (e.g., a chair, a blanket, a bed, floor, walls etc.) and movements or variations in the shape or size or position of such objects resulting from the movements of the person's body imparted or transferred to them can be picked up in the ALT data too if the objects are observed by a video camera element of a system according to the disclosed technology. This is why systems, devices and methods according to the technology disclosed herein can be used to detect heartbeats and respiration events (e.g., an inhale-exhale sequence as well as various forms or types or patterns of normal, abnormal or dysfunctional or disordered breathing) even when a person is completely hidden under a thick blanket, as we show below (see FIGS. 4A-4B and the related discussion below). Systems, devices and methods according to the technology disclosed in this patent document can also be used to detect heartbeats of a fetus inside the body (uterus) of a female.

The light source element, the video camera element, and the computing element of a system according to the technology disclosed in this patent document may be or may be not housed in a common enclosure. Further, each of the said elements can also be a part, physically and/or functionally, of a device or a system other than a system according to the technology disclosed herein. For example, a processing unit of a laptop computer (a computing element), an infrared (IR) camera of an Intel RealSense R200 unit (Intel Corporation, U.S.) embedded into the laptop computer or externally connected to the laptop computer (a video camera element), and the IR projector of the R200 unit (a light source element) form a system according to the technology disclosed in this patent document when, in combination, they are configured to perform the function of obtaining information related to at least one of the said physiologic parameters according to a method according to the technology disclosed herein. The central unifying element of such a system can be a non-transitory storage medium (e.g., a hard drive of the laptop computer or an optical disk or a flash drive) storing one or more processor-executable instruction that, when executed by a processor cause the processor to: cause a light source to illuminate one or more areas of an object, cause a video camera to collect one or more video frames, and perform computations using the collected one or more video frames and according to a method according to the technology disclosed in this patent document. The non-transitory storage medium can be included in a computing element of a system according to the disclosed technology or the non-transitory storage medium can be an element that is located outside of the computing element of the system. The non-transitory storage medium can be coupled (physically and/or communicatively) to the computing element and/or to other elements (e.g., the video camera element) of a system according to the disclosed technology. The processing unit of the laptop computer can include either a processor or a graphics processing unit (GPU) or both.

Furthermore, for example, a processing unit of a mobile device such as a phone or a tablet or a laptop (a computing element), a camera of a depth-sensing camera (e.g., an infrared camera component of the depth-sensing camera) embedded into the mobile device (a video camera element), and a light emitter of the depth-sensing camera (a light source element) form a system according to the disclosed technology when they are configured to perform the function of obtaining information related to at least one of the said physiologic parameters using a method according to the disclosed technology. The mobile device can comprise a non-transitory storage medium storing processor-executable code that, when executed by a processor (e.g., the processor or processing unit of the mobile device) causes the processor to: cause a light source element (e.g., the emitter of the depth-sensing camera embedded into the mobile device) to illuminate one or more areas of an object (e.g., a person), cause a video camera element (e.g., the infrared camera of the depth-sensing camera (or module) imbedded into the mobile device) to collect or obtain one or more video frames, as well as perform computations according to at least some steps of a method according to the disclosed technology. The processing unit of the mobile device can include either a processor or a graphics processing unit or both.

As another example, a processing unit of a mobile device such as a phone, e.g., a smartphone, or a tablet (a computing element), a camera of the mobile device (a video camera element), and a light emitter connected to (e.g., using a wired or a wireless connection) or attached to or otherwise associated with the mobile device (a light source element; the light source element can, for example, be physically attached to the mobile device or it can be in a form of a separate unit or device that can be positioned independently of the mobile device) form a system according to the disclosed technology when they, in combination, are configured to perform the function of obtaining information related to at least one of the said physiologic parameters using a method according to the technology disclosed herein. The light emitter can be controlled (e.g., activated, deactivated, or powered) by the mobile device (e.g., using the processing unit of the mobile device). For example, the mobile device (e.g., its processing unit) can be used to adjust output power or any other property of the light emitter or of light emitted by the light emitter. As another example, the light emitter can be embedded in a protective case or a (protective) cover of the mobile device. For example, the light emitter can be connected to the mobile device through a communication port of the mobile device and/or via a power port (e.g., a charging port) of the mobile device. The processing unit of the mobile device can include, for example, either a processor or a graphics processing unit (GPU) or both as well as any number of computing elements of any other type.

In one embodiment of a system according to the technology disclosed in this patent document (referred to as "the first embodiment" below), the light source element is the infrared projector of a Microsoft Kinect for Xbox 360 system (Microsoft Corporation, U.S.), the computing element is a Raspberry Pi single-board computer (Raspberry Pi Foundation, UK), and the video camera element is a Pi NoIR camera (Raspberry Pi Foundation, UK) connected to the Raspberry Pi single-board computer. Though the first embodiment can operate in virtually any lighting environment, an optical band pass filter which transmits light having wavelengths near those of the light from the Kinect projector can be used with the Pi NoIR camera to reduce effects of ambient light intensity variations which can be slow or fast (compared to a typical duration of a heartbeat or an inhale/exhale sequence, for example) such as, for example, the ones produced by incandescent light bulbs (at, e.g., 60 Hz in the U.S. or 50 Hz in Europe), especially if the incandescent light bulbs are the only source of light for a scene and/or if the rate of video frames collection by the camera is different from the frequency of the electric grid (e.g., 60 Hz in the US, 50 Hz in Europe) or integer fractions of that frequency (e.g., 30 Hz, 15 Hz, or 6 Hz in the US).

One implementation of a method according to the technology disclosed in this patent document (referred to as "the first method" below), includes:

The infrared projector of the Microsoft Kinect for Xbox 360 system projects a set of light spots onto the objects of a scene, including the body of a person, observed by the Pi NoIR camera, thus adding artificial light texture to the objects of the scene observed by the Pi NoIR camera. The infrared projector of the Microsoft Kinect for Xbox 360 system is turned on or off by the Raspberry Pi single-board computer.

Furthermore, video encoding of the video frames captured by the Pi NoIR camera using, for example, H.264 or any other video encoding or video compression standard and using a video encoder (software and/or hardware) is performed using the Raspberry Pi single-board computer and functionality provided by Picamera library (documentation for the library is available at picamera.readthedocs.io).

Furthermore, a set of the sum of absolute differences (SAD) numeric values is obtained for at least one of the encoded video frames using the motion vector data generated by the video encoder (e.g., H.264 based one) for each (or at least some) of the encoded video frames using the Raspberry Pi single-board computer and functionality provided by the Picamera library. In digital image processing, a sum of absolute differences (SAD) value is a measure of similarity between (two) image blocks within a video frame or between a first image block in a first video frame and a second image block in a second video frame. It is obtained by calculating an absolute difference between each pixel in a first image block and a corresponding pixel in a second image block being used for comparison with the first image block. These differences are summed to create a simple metric of block similarity, the $L^1$ norm of a difference image or Manhattan distance between two image blocks.

Furthermore, for at least one of the encoded video frames for which a set of SAD values was obtained, and for at least one part of the set of SAD values, a sum of the SAD values in the part is calculated to obtain a numeric value referred to as the "sSAD" value below using the Raspberry Pi single-board computer (if the part contains a single SAD value, then that SAD value is provided as the sSAD value). The part of the SAD values set corresponds to the area (or part) of the video frame which was used to obtain the SAD values belonging to the part. The sSAD values (obtained for a single video frame or for several video frames) form a set of the ALT data values referred to above. A sSAD value represents a measure of motion in a video frame or in its part for which the sSAD value was computed.

Python code which runs on a Raspberry Pi single-board computer having a Pi NoIR camera connected to it and implements the video frames capture and processing steps described above for the case when a sum of the SAD values is calculated for the whole set of the SAD values can be found in the LISTING 1 below. Methods according to the technology disclosed herein can be applied to whole video frames or to any part or parts of the video frames without any limitation.

The computed sSAD values contain information about the respiration and/or heartbeats and/or other movements of a person (as well as of the objects (animate or inanimate) that may be in direct or indirect (e.g., through other objects) contact with the person) observed by the Pi NoIR camera over the time period covered by the video frames for which the sSAD values were obtained. Numeric values representative of the respiration rate and/or heart rate of the person over that time period can be obtained, for example, by performing Fourier analysis (e.g., using fast Fourier transform (FFT)) of the sSAD values (see, for example, FIG. 2 and the related description below). Numeric values representative of the heart rate variability and/or respiration rate variability can be obtained, for example, by identifying positions of the peaks corresponding to the heartbeats and/or the respiration events (e.g., inhale and/or exhale) in the sSAD data, determining durations of the time intervals between the successive heartbeat and/or respiration peaks to result in a series of the time interval duration values for the heartbeats and/or respiration, and performing statistical calculations for the obtained series of the time interval duration values, e.g. producing a histogram of the time interval duration values and/or determining parameters such as a mean value and/or a standard deviation value of the distribution of the time interval duration values, in order to thus obtain information about the variation of the time interval durations over the time period covered by the said video frames.

As a practical starting point, the Kinect system can be placed at approximately 5 feet distance from a person with the Pi NoIR video camera placed in the vicinity of the Kinect (Kinect plays the role of a light source element in the first embodiment of a system according to the disclosed technology). The distance between the Kinect and/or the video camera and the person can affect how pronounced the heartbeat signal will be during respiration events (see, e.g., FIGS. 1 and 5A, 13A-13B, and 14A-14B, and the related description below). At a large enough distance between the Kinect and/or the camera and the person there can be virtually no discernable pulse and/or respiration signal in the ALT data. Generally, the closer Kinect and/or the camera gets to the person, the less pronounced the heartbeat signal component in the ALT data becomes during respiration events. Adjustments of the Kinect (light source) and/or the video camera position can be made, for example, based on observing visualizations of the collected ALT data.

Note that there were virtually no movements of a person's body other than the ones related to the person's respiration and heartbeats during collection of the data shown in all FIGS. discussed below.

An example of the ALT data captured by the first embodiment of a system (described above) using the first method (described above) according to the technology disclosed in this patent document is shown in FIG. 1. ALT data collection was performed during daytime at 49 data points per second rate (which corresponds to 49 frames per second video capture setting of the Pi NoIR camera, see LISTING 1 below) with simultaneous HD video (720p) recording (see LISTING 1 below). The video frame size was set to 1280× 720 pixels (see LISTING 1 below). A person was at 1.5 meters (5 feet) distance from the Pi NoIR camera. The camera observed upper ⅔ of the person's body. The H.264 video encoder produced I-type and P-type video frames at a ratio of 1 I-type video frame followed by 59 P-type video frames in this example. Motion vector data for I-type video frames and, consequently, sSAD values for I-type video frames are zero. Zero sSAD value of each I-type video frame was replaced by the sSAD value of the preceding P-type video frame in the sSAD data shown in FIGS. 1, 4A, 5A, 8A, and 8B. H.264 video encoder can be instructed to produce a single I-type video frame followed by P-type video frames only by setting the appropriate parameter for its operation (see LISTING 1 below). "Video compression picture types", article retrieved on Oct. 21, 2018 from the Internet (<URL: https://en.wikipedia.org/wiki/Video_compression_picture-_types>) provided the following description of the I and P types of the video frames: "The three major picture types used in the different video algorithms are I, P and B. They are different in the following characteristics: I-frames are the least compressible but don't require other video frames to decode. P-frames can use data from previous frames to decompress and are more compressible than I-frames. B-frames can use both previous and forward frames for data reference to get the highest amount of data compression."

Each data point 100 in FIG. 1 represents the sSAD value for an encoded video frame. The sSAD values can be determined using the vertical axis 110 in FIG. 1. The time progression in FIG. 1 is from left (earlier-captured frames) to right (later-captured frames). The sSAD value data points are connected by straight lines in FIG. 1. The region 120 of the sSAD values in FIG. 1 approximately corresponds to one respiration cycle of the person (inhale followed by exhale). The sSAD values in the region 120 in FIG. 1 reflect both the person's respiration and heartbeats. The region 130 of the sSAD values in FIG. 1 corresponds to a time interval when the person did not breathe. The sSAD values in the region 130 in FIG. 1 reflect the person's heartbeats only.

Figure 2:
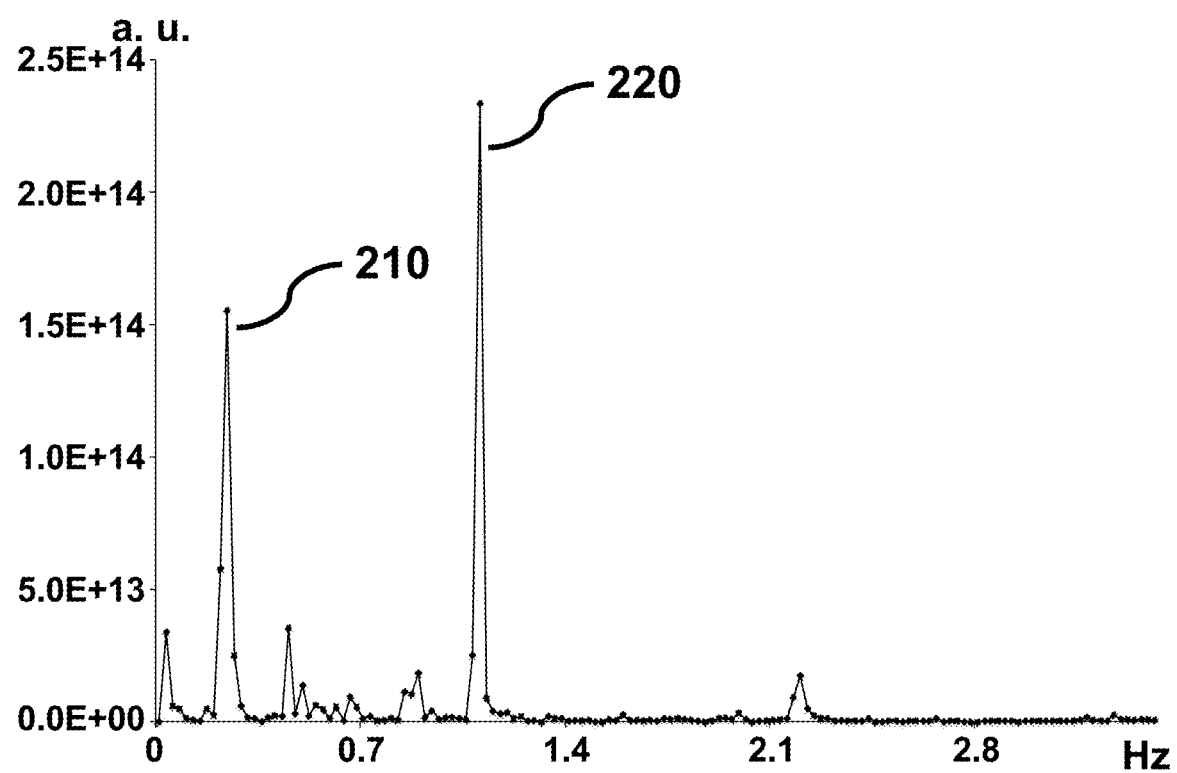
FIG. 2 shows a result of a fast Fourier transform applied to a part of the data shown in FIG. 1.

Region 140 in FIG. 1 containing 2048 sSAD data points was used to produce the frequency spectrum shown in FIG. 2. Time length of the interval 140 in FIG. 1 is approximately 42 seconds. The average value of the sSAD data points in the region 140 in FIG. 1 was subtracted from each of the sSAD values in the region 140 in FIG. 1 followed by application of fast Fourier transform (FFT) to thus obtained average-corrected sSAD values. Frequency peaks 210 (0.24 Hz) and 220 (1.12 Hz) in FIG. 2 correspond to the respiration rate and the heart rate of the person during the time interval 140 in FIG. 1, respectively. The frequency values for the peaks 210 and 220 in FIG. 2 correspond to the equivalent values of 14 respiration cycles per minute and 67 heartbeats per minute, respectively.

Figure 3A:
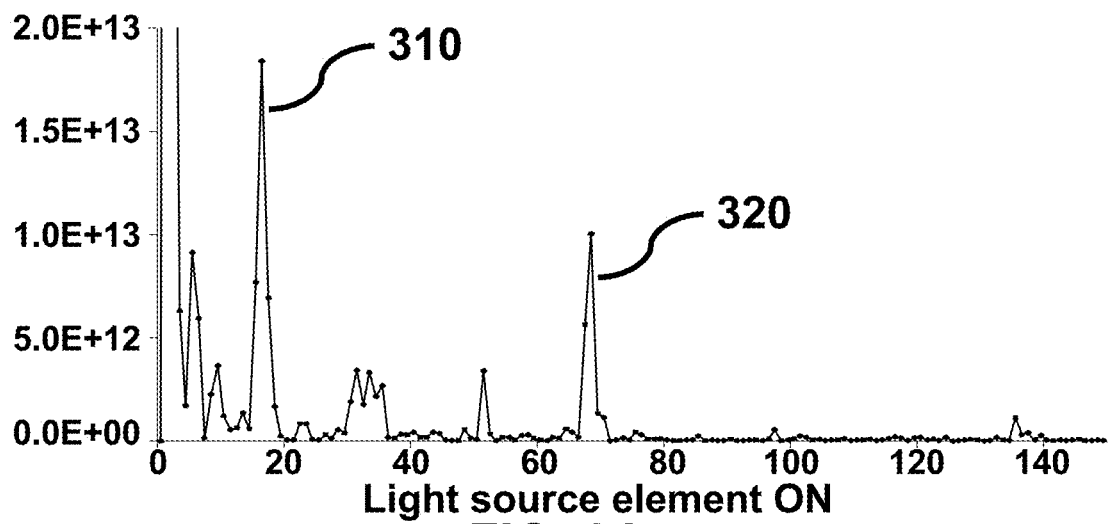
FIGS. 3A-3C show that application of the additional light texture to a person's body by a system according to the technology disclosed herein can lead to a significant increase of the components of the data collected by the system that are related to the respiration and heart activity of the person.
Figure 3B:
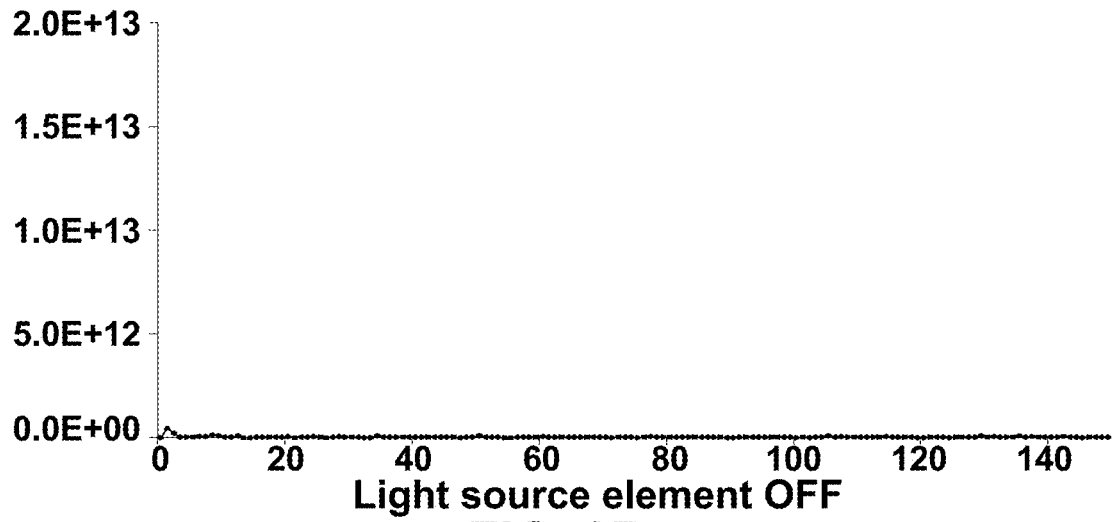
Figure 3C:
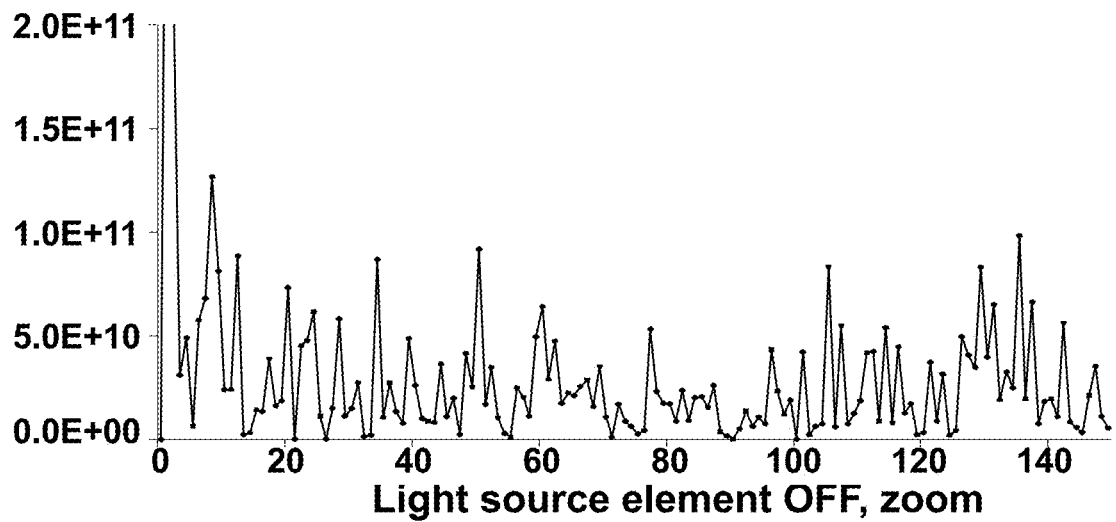

To demonstrate the amplification function of the additional light texture, ALT data collection was performed using the first embodiment of a system and the first method according to the technology disclosed herein, which are described above, during daytime at 90 data points per second rate (which corresponds to 90 frames per second video capture setting of the Pi NoIR camera). The video frame size was set to 640×480 pixels. A person was at approximately 1.3 meters (4.3 feet) distance from the Pi NoIR camera. The camera observed about ½ of the person's body. FIGS. 3A and 3B show frequency spectra which were obtained in the same way as the one in FIG. 2, via fast Fourier transformation of a sSAD values data set. The sSAD data sets used to obtain spectra shown in FIGS. 3A and 3B had the same length and corresponded to one minute long data collection time. The said sSAD data sets were collected under the same ambient lighting conditions in the room (the ones excluding the additional illumination created by a light source element). Light emitter of a Microsoft Kinect for Xbox 360 unit was active (switched ON) during collection of the sSAD data set corresponding to FIG. 3A, and the light emitter was inactive (switched OFF) during collection of the sSAD data set corresponding to FIG. 3B. Note that the vertical scales of the plots in FIGS. 3A and 3B are the same. FIG. 3C shows the same data as FIG. 3B, yet the maximum value of the vertical axis in FIG. 3C is one hundred times smaller compared to the maximum values of the vertical axes of the plots in FIGS. 3A and 3B (2.0E+11 for the plot in FIG. 3C vs. 2.0E+13 for the plots in FIGS. 3A and 3B). Therefore, the frequency components 310 and 320 corresponding to respiration and heartbeats of a person, respectively, in the spectrum shown in FIG. 3A are at least one hundred times larger compared to the frequency components in the same regions of the frequency spectra shown in FIGS. 3B and 3C. Horizontal axis numbers of the plots in FIGS. 3A, 3B, and 3C correspond to the frequency bin numbers of the FFT.

Therefore, the data shown in FIGS. 3A, 3B, and 3C demonstrate that application of the additional light texture leads to at least two orders of magnitude amplification of the frequency components corresponding to a person's respiration and heartbeats (pulse) in the frequency spectra compared to the case when there is no additional light texture present.

Note that both the respiration rate and the heart rate can be determined from the same sSAD data, as, for example, demonstrated above on the example of the sSAD data shown in FIG. 1.

Note that the "baseline" or base level of the sSAD values can be, for example, in the range of hundreds of thousands (see, e.g., FIG. 1) while the respiration and/or heartbeats components of the sSAD signal can have only several percent amplitude relative to the baseline even when the artificial light texture is applied to a person's body.

FIGS. 4B, 5B, 7, 9, and 10 show images captured by a Pi NoIR camera which have been converted to grayscale images.

To demonstrate that systems, devices and methods according to the technology disclosed in this patent document can be used to detect heartbeats and respiration even when a person is completely covered by a thick blanket, ALT data collection was performed using the first embodiment of a system and the first method described above. The data collection was done during nighttime at 49 data points per second rate (which corresponds to 49 frames per second video capture setting of the Pi NoIR camera). The video frame size was set to 1280×720 pixels.

Figure 4A:
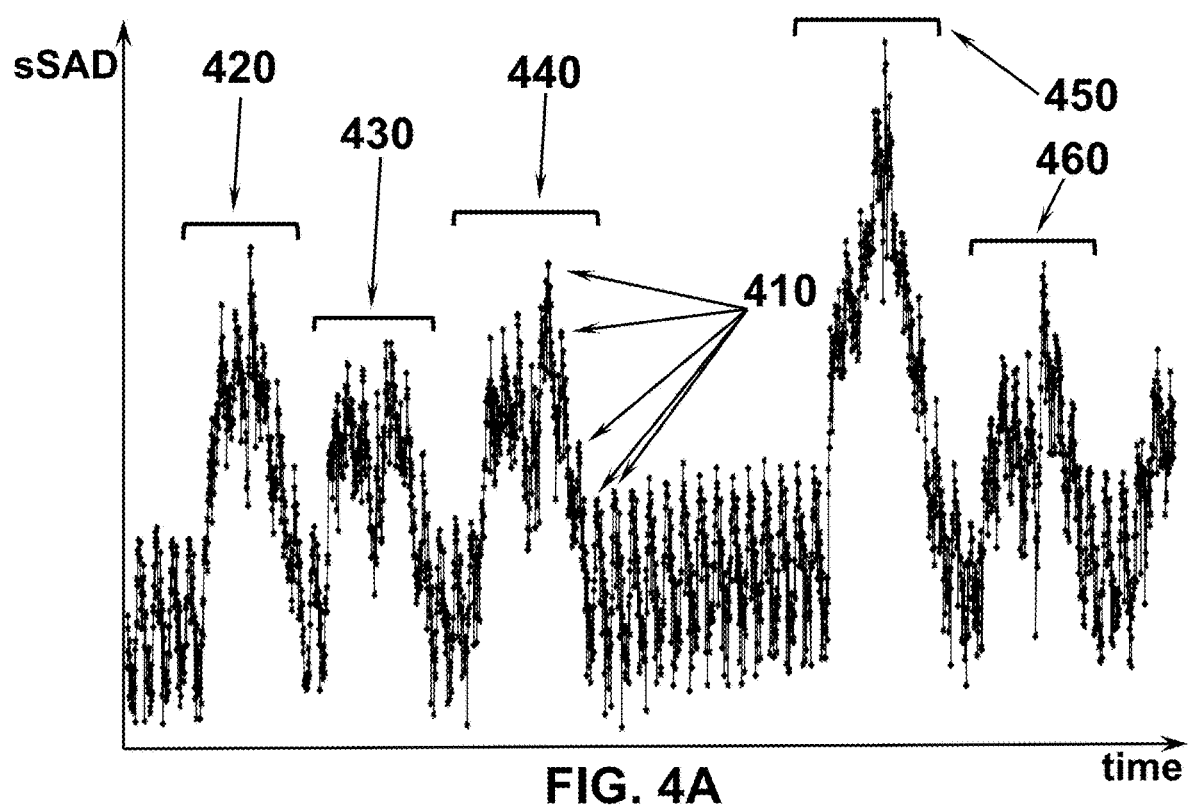
FIGS. 4A-4B show that systems and methods according to the technology disclosed in this patent document can be used to detect heartbeats and respiration of a person even when the person is completely covered by a thick blanket.
Figure 4B:
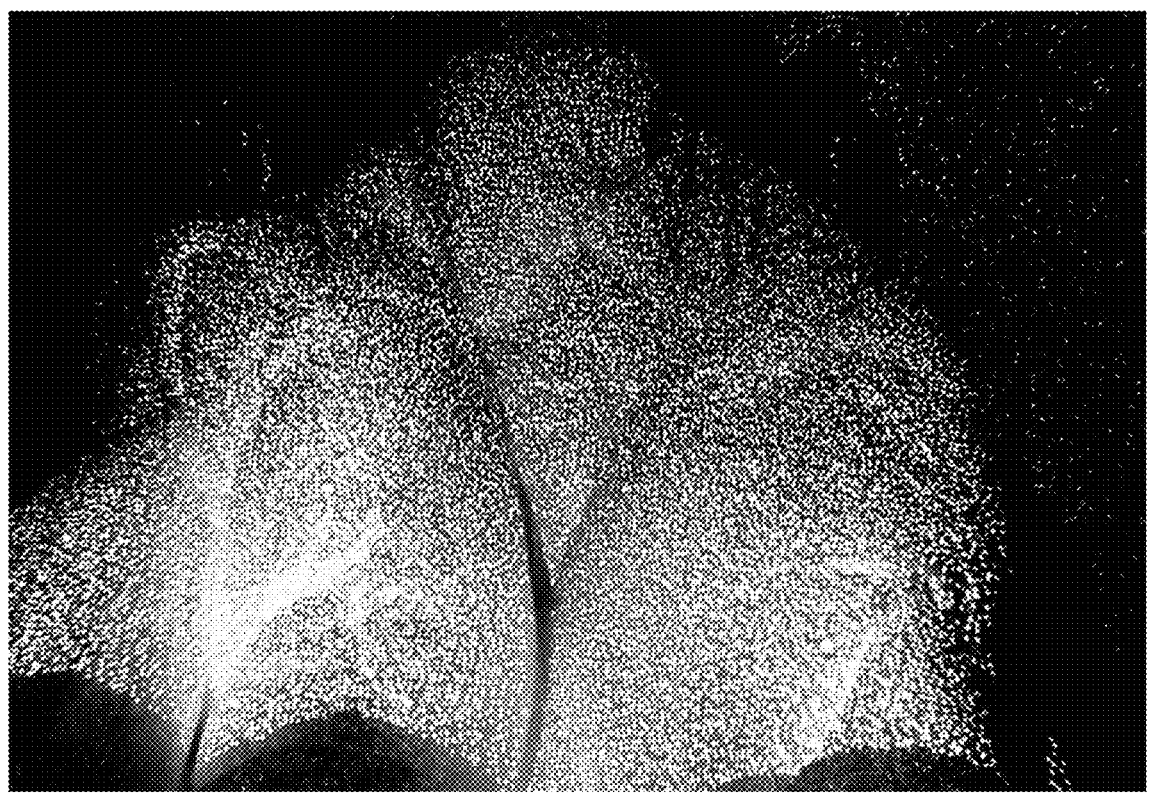

FIG. 4B shows a person reclining in an armchair and completely covered by an "IKEA 365+ MYSA" quilt/blanket having "warmth rate" 6 ("thick and heavy" quilt, 150×200 cm, 1730 g filling weight). The room in FIG. 4B was almost completely dark for a human eye because human eyes are mostly insensitive to the infrared light near the wavelengths on which Kinect's projector operates. The remnant illumination in the room, which could be noticed by a person, was due to the distant streetlights and LEDs of the electronics equipment in the room. Note that ALT works in daylight too, as data in FIGS. 1-3 demonstrate, for example.

FIG. 4A shows ALT data collected for the person under the blanket in FIG. 4B. The duration of the dataset in FIG. 4A is about one minute. Both respiration and pulse signals are pronounced in FIG. 4A. Several of the consecutive heartbeats are marked by the arrows 410 in FIG. 4A. Each of the five regions of the ALT data under the brackets shown in FIG. 4A and marked by the arrows 420, 430, 440, 450, and 460 corresponds to a respiration cycle (inhale followed by exhale). Note that there was breath hold between the respiration cycles 440 and 450 and that the person made a relatively (relative to other respiration cycles shown in FIG. 4A) fast inhale during the respiration cycle 450 following the breath hold, which is reflected in the rate of change and the amplitude of the ALT data for that cycle in FIG. 4A.

Figure 5A:
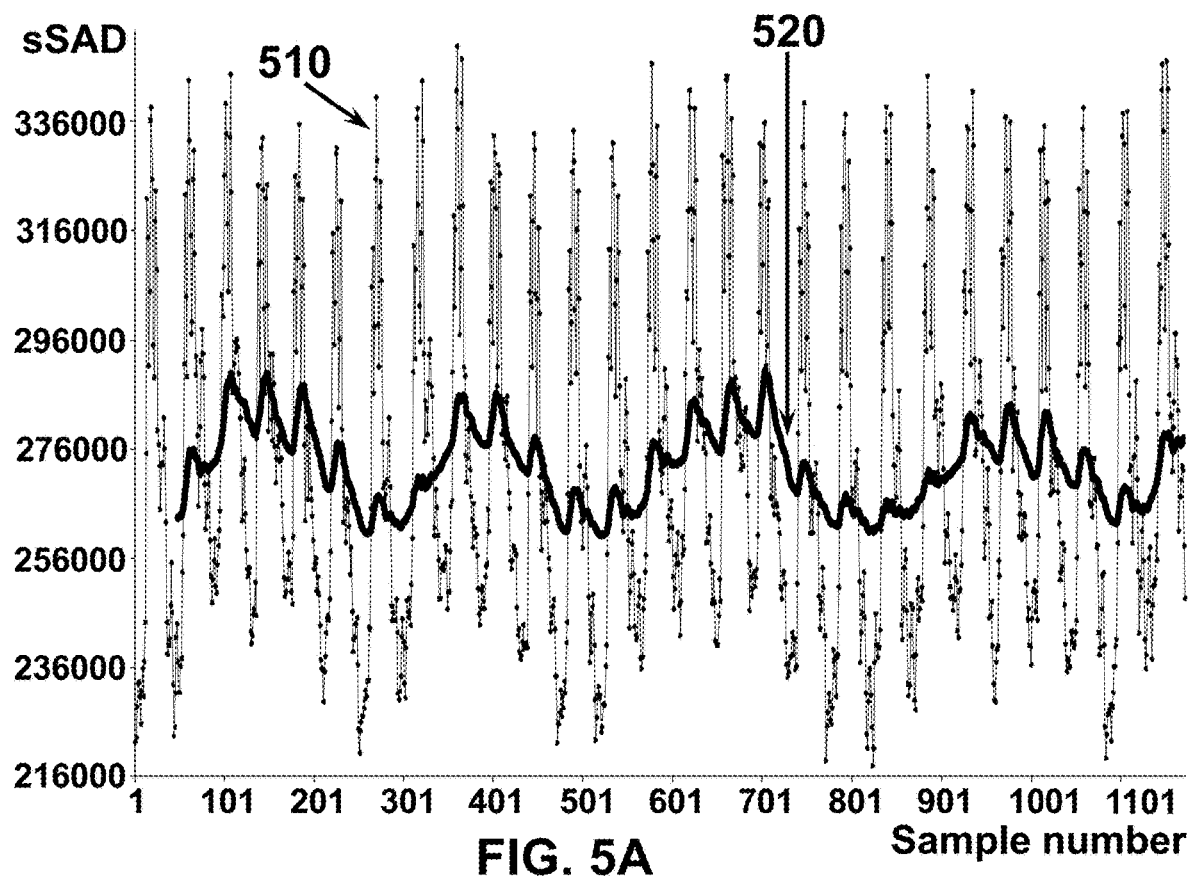
FIGS. 5A-5B show that systems and methods according to the technology disclosed in this patent document can be used to detect heartbeats and respiration of a sleeping person during nighttime without use of additional lighting or illumination.
Figure 5B:

FIG. 5B shows an image of a person sleeping under a blanket on a bed during nighttime. A Pi NoIR camera captured the image. FIG. 5B shows the light spots produced by the light emitter of a Kinect for Xbox 360 unit which accounted for the majority of illumination for the scene observed by the Pi NoIR camera. The light spots formed distinct illumination areas, the elements of the artificial light texture created by the light emitter. The elements of the artificial light texture shown in FIG. 5B will be discussed in more detail below (see, e.g., FIG. 10 and the related discussion below). Both the Pi NoIR camera and the Kinect unit were at about ~2.3 m (7.5 feet) minimum distance (the distance to the closest point of the person's body) from the person in this case.

The ALT data shown in FIG. 5A were collected using the first embodiment of a system and the first method according to the technology disclosed herein, that are described above, at 49 samples per second rate. The frame size of the video captured by the Pi NoIR camera was set to 1280×720 pixels. Thin black lines 510 in FIG. 5A connect the sSAD data points. ALT data in FIG. 5A reflect both respiration and heartbeats of the person. Further, a 49-points moving average was calculated for the sSAD values shown in FIG. 5A to highlight the respiration process captured in the ALT data. The thick black line 520 in FIG. 5A goes through the points which are the result of the said moving average calculations and shows that there were four full respiration cycles captured in the ALT data shown in FIG. 5A. There were 27 heartbeats in total captured in the ALT data shown in FIG. 5A.

As discussed above, application of the additional light texture can greatly increase illumination contrast in the scene observed by a video camera, especially in a low ambient light environment such as the one that is typically present during nighttime. FIG. 5B illustrates this statement well. Without the illumination produced by the Kinect's light emitter FIG. 5B would be (almost) uniformly pitch-black.

If, for example, n is the number of bits used to represent the shades of gray in a grayscale image, such as, for example, the one shown in FIG. 5B, than the minimum ratio (the minimum ratio of a larger value to a smaller value) of grayscale values of the pixels belonging to two areas or parts of a person's body in the image is $1+1/(2^n-2)$. If n=16, the ratio is about 1.000015. The ratio of the said grayscale pixel values reflects the ratio of levels of illumination of the body areas covered by the said pixels in the image and can be used as a measure of illumination contrast between different parts of the image and/or of a video frame captured by a video camera element and/or as a measure of the illumination contrast between the said body areas. If a light source element, such as the one used in the first embodiment of a system according to the technology disclosed in this patent document is the only or the major source of illumination for a scene observed by a video camera element (as is the case for FIGS. 4B and 5B, for example), then objects illuminated by the light source element and, consequently, video frames captured by the video camera element will have areas with vastly different illumination, and hence large values of the illumination contrast between those areas (e.g. $2^n-1$ between the pixels having the minimum non-zero grayscale level value of 1 and the maximum grayscale level value of $2^n-1$; the ratio is 65535 for n=16, for example), as compared to the case when the scene observed by the video camera element has no illumination in it (e.g. when the light source element is switched off; we assume that the minimum grayscale level value for any pixel in a grayscale image is 1 to avoid considering "divide by zero" operations) in which case the ratio (illumination contrast) would be equal to 1. The number N of bits in a binary representation of any numeric value associated with a pixel of a video frame or otherwise related to a video frame can be any integer number. For example, the number of bits used to represent the shades of gray in a grayscale image can be 8, 16 (as used in the example above), 32, 64, 128, 256, 512, 1024, etc. (the values do not have to be equal to powers of two).

Note that a light source which provides substantially spatially uniform illumination of the scene as observed by a video camera element (compared to the illumination created by a light source element which creates the additional light texture) can be used in addition to the light source element which creates the additional light texture, if, for example, such added substantially uniform illumination can aid a person to see the elements of the scene as captured in the video frames by the video camera element better compared to the case when the light source element which creates the additional light texture is the main or the only source of illumination for a scene, as is the case for FIG. 5B, for example. In some implementations, the light source element producing the additional light texture can also produce the said substantially spatially uniform illumination.

In the methods according to the technology disclosed in this patent document, we use measures of motion in at least a part of a video frame such as the one based on the sSAD value. One can also use any other measure of motion in at least a part of a video frame in any of the methods according to the disclosed technology. For example, one can calculate absolute values of the motion vector components generated, for example, by a video encoder (such as H.264 based one, for example) for a macroblock of a video frame (the components of said motion vector are referred to as the X-component and Y-component) and find a sum of the absolute values of the motion vector components for at least a part of the macroblocks of at least a part of the video frame. Such measure of motion is referred to as XYabs below. One can also use a measure of motion based on a sum of the lengths of the motion vectors calculated using motion vector components generated, for example, by a video encoder (e.g., such as the one complying with the H.264 standard or any other video encoder) for at least a part of the macroblocks in at least a part of a video frame. One can also use a measure of motion based on a sum of the lengths of the motion vectors which (the motion vectors) are generated through an optical flow type of analysis of the video frames (e.g., of a sequence of video frames). In the case of using an optical flow-based measure of motion, the elements of artificial light texture created by a light source element of a system according to the disclosed technology can be considered to be the objects which motion is followed in the video frames using optical flow or an optical flow-based method. Optical flow-based methods of video analysis can be applied to these artificial light texture elements created through operation of a light source element according to the technology disclosed herein.

Figure 6:
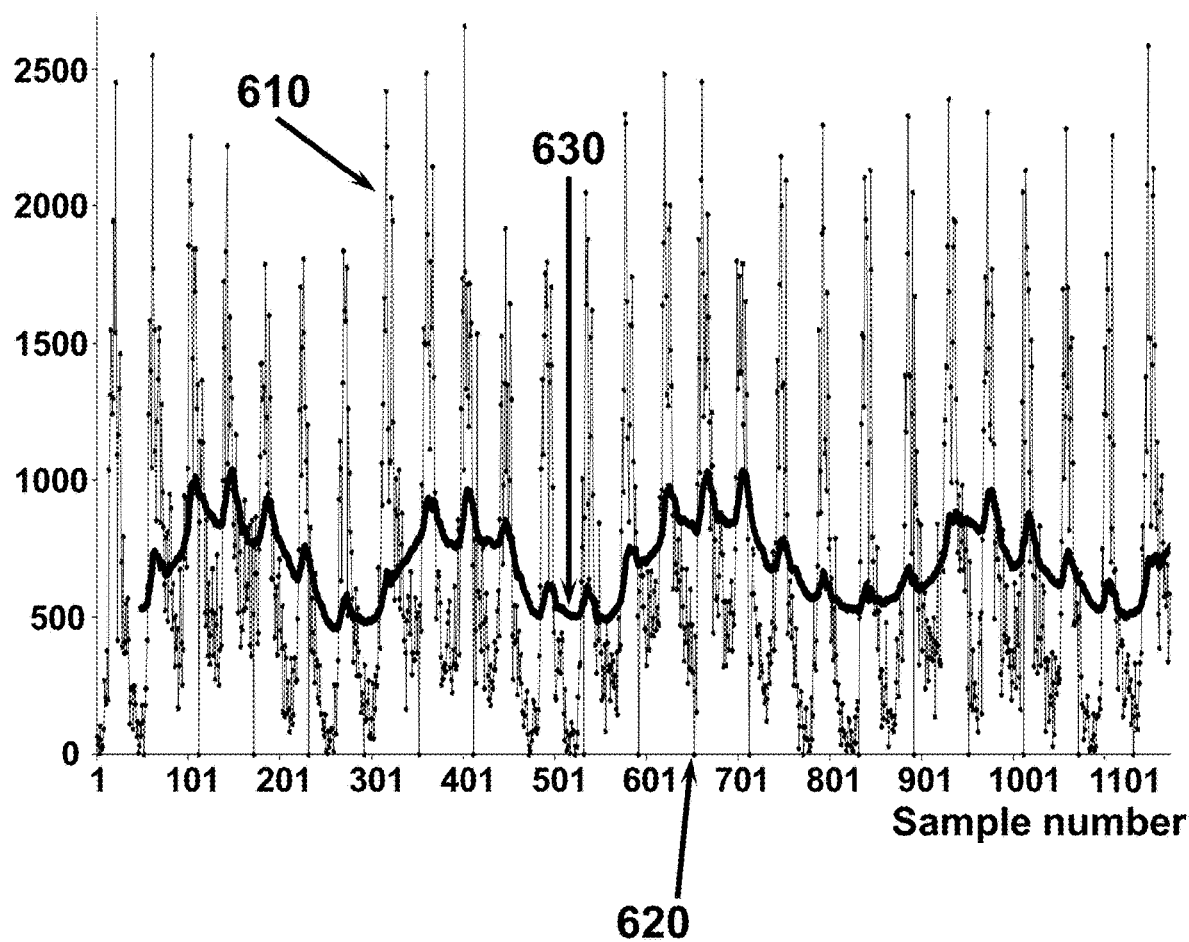
FIG. 6 shows example data obtained by a system according to the disclosed technology using an implementation of a method according to the technology disclosed herein.

FIG. 6 shows the XYabs values computed for the same video frames which were used to produce sSAD data shown in FIG. 5A. Lines 610 in FIG. 6 connect XYabs data points. Similarly to the sSAD values for the I-type video frames, XYabs values for the I-type video frames are equal to zero. XYabs value (zero) for one of the I-type video frames from the video frames set used to generate the data shown in FIGS. 5A and 6 is indicated in FIG. 6 by the arrow 620. Similarly to FIG. 5A, a 49-points moving average was calculated using the XYabs values to highlight the respiration process (inhale followed by exhale) captured in the ALT data. The thick black line 630 in FIG. 6 goes through the points which are the result of the said moving average calculations and shows that there were four full respiration cycles captured in the ALT data shown in FIG. 6. FIG. 6 shows the same number of heartbeats, 27, as does FIG. 5A. An XYabs value represents a measure of motion in a video frame or in its part for which the XYabs value was computed.

Figure 7:
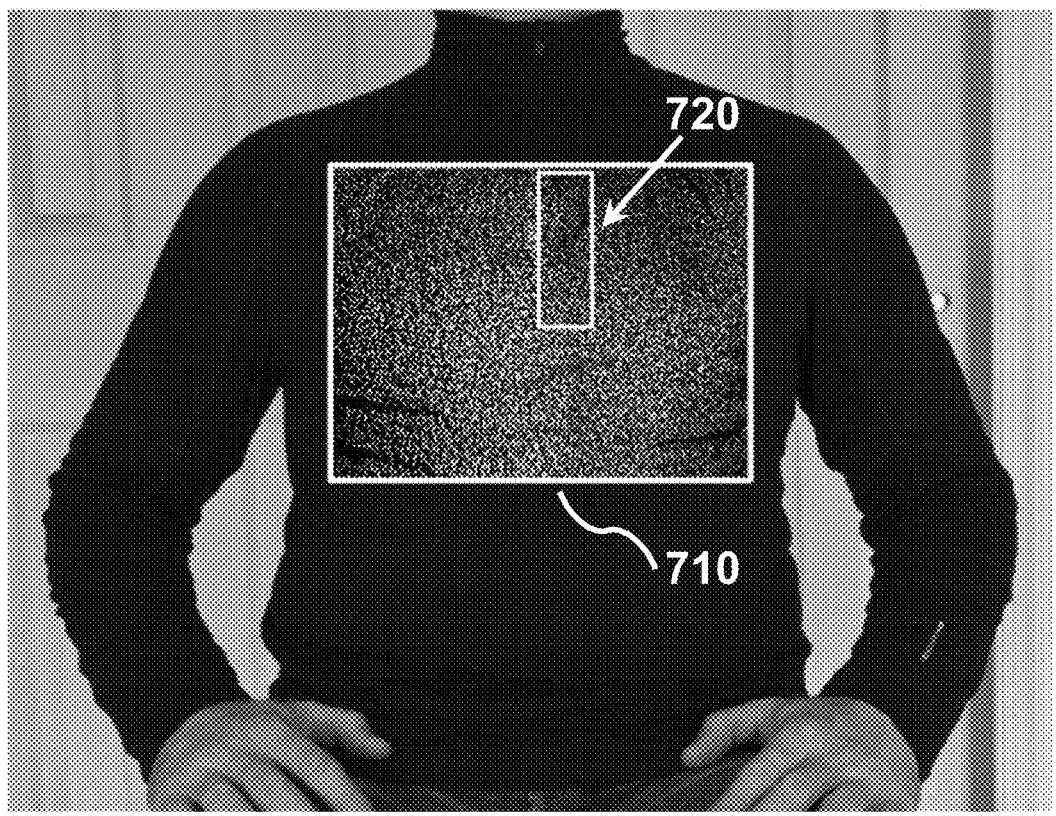
FIG. 7 shows a person sitting on a chair.
Figure 8A:
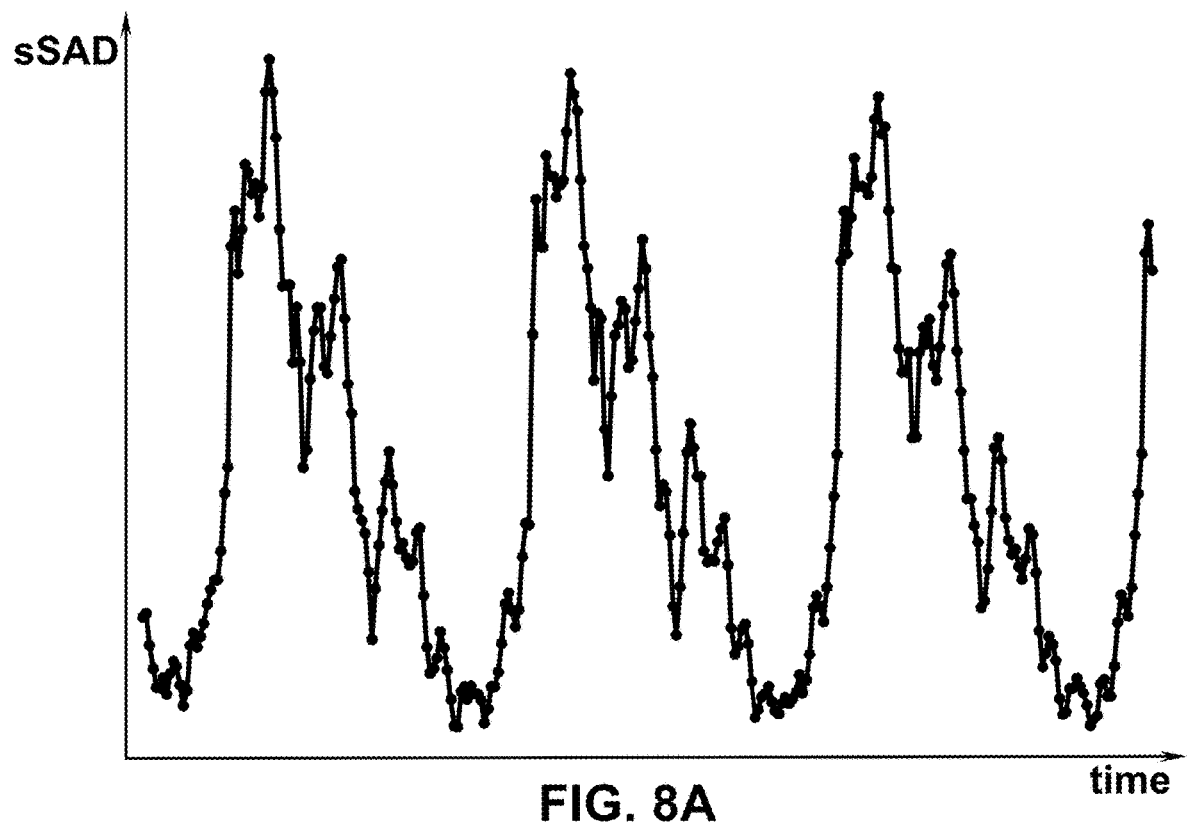
FIGS. 8A-8B show that systems and methods according to the technology disclosed in this patent document can be used to obtain temporal profiles of heartbeats of a person from different parts of the person's body in a non-contact fashion and with high temporal resolution.
Figure 8B:
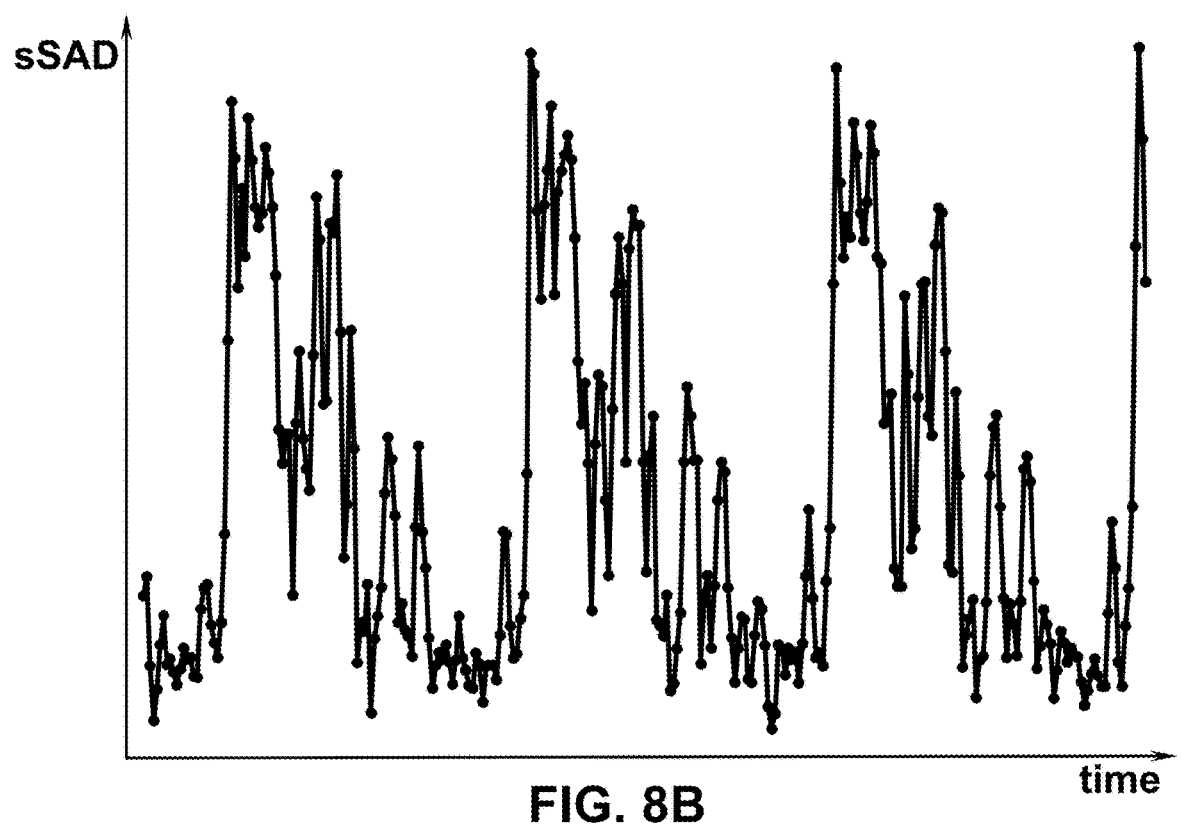

Systems, devices and methods according to the technology disclosed herein can be used to obtain pulse, respiration, and other (mechanical motion) information specific to different parts of a person's body simultaneously and with high temporal resolution via processing respective segments of the captured video frames. FIGS. 7, 8A, and 8B show that systems, devices and methods according to the technology disclosed in this patent document can be used to obtain information about the intricate details of the mechanical movements of a heart in a non-contact fashion. Collection of the ALT data shown in FIGS. 8A and 8B was performed during daytime using the first embodiment of a system and the first method according to the technology disclosed herein (described above).

FIG. 7 shows a part of the upper body of a person. The rectangle 710 in FIG. 7 surrounds the area observed by a Pi NoIR camera and illuminated by the light emitter of a Kinect for Xbox 360 unit. Note that the part of the image shown in FIG. 7 within the rectangle area 710 was obtained separately from the rest of the image and put on top of the said rest of the image to provide a better illustration of the location of the imaged areas of the person's body. The camera's frame size was set to 640×480 pixels. Data in FIGS. 8A and 8B were collected by the Pi NoIR camera running at 90 frames per second rate, which gives 11 milliseconds time interval between the data points, given that the Pi NoIR camera's video capture parameters were fixed during the acquisition of the video frames used to produce sSAD data values shown in FIGS. 8A and 8B (see LISTING 1 below). Both the Pi NoIR camera and the Kinect unit were at about 0.6 m (~2 feet) distance from the person when the image in the area 710 and the data shown in FIGS. 8A and 8B were obtained.

FIG. 8A shows ALT data for three heartbeats obtained by processing the whole video frames captured by the Pi NoIR camera (640×480 pixels, corresponds to the rectangle 710 in FIG. 7). The data in FIG. 8B correspond to the same heartbeats which are shown in FIG. 8A. The ALT data in FIG. 8B were obtained for the areas around the person's heart marked by the rectangle 720 in FIG. 7 by processing the parts of the whole video frames captured by the Pi NoIR camera which correspond to the rectangle 720 in FIG. 7 using the first method according to the technology disclosed in this patent document. Note that the vertical axes in FIGS. 8A and 8B have different scales (not specified).

As FIGS. 8A and 8B demonstrate, the ALT data collected from the small regions 720 close to the person's heart (FIG. 8B) exhibit higher resolution for the details of the heartbeat profile compared to the ALT data for the whole area within the rectangle 710 in FIG. 7 (FIG. 8A).

The data in FIGS. 8A and 8B demonstrate that systems, devices and methods according to the technology disclosed in this patent document can be used to obtain information specific to different parts of a body via processing different segments or areas of the video frames captured by a video camera element. ALT data collection can be performed with high temporal resolution (time interval between the data points in FIGS. 8A and 8B is 11 ms which is limited by the maximum frame rate of the used video camera element). These capabilities of the systems and methods according to the technology disclosed in this patent document can be valuable, for example, for medical imaging applications where tracking pulse, heartbeats, respiration, and other movements is required for the whole body and/or for any number of its specific areas. FIGS. 8A and 8B demonstrate that systems, devices and methods according to the technology disclosed herein can be viewed as a non-contact analog of the seismocardiography and/or ballistocardiography methods of monitoring the mechanical activity of a heart and a vascular system.

Systems and methods according to the technology disclosed in this patent document can be used to obtain information related to the temporal characteristics of at least a part of a heartbeat, and temporal characteristics of at least a part of a respiration cycle via, for example, determining temporal positions of the sSAD values or sSAD values maxima relative to a fixed time point or relative to each other, or determining a duration of time during which sSAD values are above a certain level or within a certain range of numeric values, or by establishing or determining temporal positions of points (or intervals) of an extreme (e.g., a maximum or a minimum (e.g., a local or a global maximum or minimum)) variation among the sSAD values, or by establishing a time dependence (or a function (e.g., a discreet function)) of the sSAD values corresponding to at least a part of a heartbeat or at least a part of a respiration cycle (the established time dependence can be used to determine temporal durations and/or positions of various features of the time dependence including but not limited to the ones mentioned above).

FIG. 9 shows images 910 and 920 obtained by a system according to the first embodiment according to the technology disclosed in this patent document with the Pi NoIR camera focused on the same area of a person's body which is shown within the rectangle 710 in FIG. 7. The images 910 and 920 were obtained under the same conditions as the one within the rectangle 710 in FIG. 7.

White rectangles 930 and 940 in FIG. 9 surround the areas of the images 910 and 920, respectively, which are shown in the images 970 and 980 in FIG. 9, respectively. Rectangles 930 and 940 have the same position within the images 910 and 920, respectively. The images 910 and 920 have the same dimensions.

As the images 910, 920, 970, and 980 in FIG. 9 show, the light emitter element of the system according to the first embodiment according to the disclosed technology that was used to obtain the images shown in FIG. 9 illuminates (is configured to illuminate) a set of areas of a person's body by creating light spots on those areas. Two of those light spots are indicated by the arrows 950 and 960 in FIG. 9. The said light spots generally have arbitrary shapes, as captured by a video camera and are separated from each other by the areas of the person's body having lower illumination compared to that of the light spots. The said light spots form the elements of the additional light texture (also called artificial light texture) produced by the system.

Image 910 and, consequently, its part 970 were taken in between the heartbeats of the person when the person did not breathe. Image 920 and, correspondingly, its part 980 were obtained in the middle of a respiration cycle of the person.

As comparison of the images 910 and 920, and of their parts 930 and 940 shown in the images 970 and 980 in FIG. 9, respectively, indicates, respiration, heartbeats, and/or other movements of the person's body can lead to variations in any of the illumination, shape, size, or location of the individual elements of the artificial light texture, as well as to a difference in the number of the elements of the artificial light texture between the images 910 and 920, and between their parts 930 and 940 shown in the images 970 and 980 in FIG. 9, respectively. Comparison of the images 910 and 920, and of their parts 930 and 940 shown in the images 970 and 980 in FIG. 9, respectively, also demonstrates that respiration, heartbeats, and/or other movements of the person's body (or movements of part(s) (internal or otherwise) of the person's body) can lead to variations in any of a distribution (e.g., a statistical distribution) of illumination (or illumination level or illumination intensity; e.g., average illumination (average level of illumination or average illumination intensity)) within a single element of the artificial light texture and/or among different elements of the artificial light texture, a distribution of shape of the elements of the artificial light texture, a distribution of size of the elements of the artificial light texture, and/or a distribution of location or position of the elements of the artificial light texture. The said variations are captured, at least in part, by a video camera element in a set of video frames which are processed by a computing element according to a method according to the technology disclosed herein to result in a set of numeric values (ALT data) which can be further processed to obtain numeric values representative of the information related to any parameter in the said group of physiologic parameters of the person, as discussed above, for example, and/or processed to display at least a part of the set of numeric values using a graphical representation such as a 2D plot, as shown, for example, in FIGS. 8A and 8B.

FIG. 10 shows images 1010 and 1020 obtained by a system according to the first embodiment according to the technology disclosed in this patent document with the Pi NoIR camera of the system focused on the same scene which is shown in FIG. 5B. The images 1010 and 1020 were obtained under the same conditions as the one in FIG. 5B.

White rectangles 1030 and 1040 in FIG. 10 surround the areas of the images 1010 and 1020, respectively, which are shown in the images 1050 and 1060 in FIG. 10, respectively. Rectangles 1030 and 1040 have the same position within the images 1010 and 1020, respectively. The images 1010 and 1020 have the same dimensions. Rectangles 1030 and 1040 surround the chest and abdomen areas of a person covered by a blanket.

As images 1010, 1020, 1050, and 1060 in FIG. 10 show, the light emitter element of the system according to the first embodiment according to the disclosed technology illuminates (is configured to illuminate) a set of areas of the person's body by creating light spots on those areas. The said light spots can generally have arbitrary shapes, as captured by a video camera element, and are separated from each other by the areas of the person's body having lower illumination compared to that of the light spots. The said light spots form the elements of the additional (artificial) light texture produced by the system according to the first embodiment according to the technology disclosed herein.

Image 1010 and, accordingly, its part 1030 shown in the image 1050 in FIG. 10 were taken in between the heartbeats of the person when the person did not breathe. Image 1020 and, consequently, its part 1040 shown in the image 1060 in FIG. 10 were obtained during a respiration cycle of the person.

As comparison of the images 1010 and 1020, and of their parts shown in the images 1050 and 1060 in FIG. 10, respectively, indicates, respiration, heartbeats, and/or other movements of the person's body predominantly lead to variations in the illumination distribution of the elements of the artificial light texture between the images 1010 and 1020, and between their parts shown in the images 1050 and 1060 in FIG. 10, respectively, as compared to variations in the illumination distribution, the shape distribution, the size distribution, the location distribution, and the difference in the number of the elements of the artificial light texture between the images 910 and 920, and between their parts shown in the images 970 and 980 in FIG. 9, respectively. Note that the light source element and the camera element were positioned at a larger distance from the person in the case shown in FIG. 10 (~2.3 m minimum distance) compared to the case shown in FIG. 9 (~0.6 m). The said variations are captured, at least in part, by a video camera element in a set of video frames which are processed by a computing element according to a method according to the technology disclosed in this patent document to result in at least one set of numeric values (ALT data) which can be further processed to obtain numeric values representative of or indicative of or containing the information related to least one physiologic parameter of the person in the said group of physiologic parameters, as, for example, discussed above, and/or to display at least a part of the set of numeric values using a graphical representation such as a 2D or 3D plot, as shown, for example in FIGS. 5A and 6.

With respect to the mentioned difference between the responses of the elements of the additional light texture to the movements of a person's body, including those associated with the person's respiration and heartbeats, shown in FIGS. 9 and 10, consider the case where the light source element and the video camera element are placed at essentially the same location. At large enough distances between the light source and the camera element, on one end, and the person, on the other end, the elements of the additional light texture created by the light source element on the surfaces of the person's body, as observed by the video camera element, are small, occupying a single pixel or a small group of a few pixels in the video frames captured by the video camera element (the first case of the distance, generally corresponds to the cases shown in FIGS. 5B and 10). In the first case of the distance, movements of the person's body, including those associated with heartbeats and respiration, predominantly result in changes in the illumination distribution of the ALT elements, as observed by the video camera element. As the distance between the video camera element and/or the light source element, on one end, and the person, on the other end, gets smaller, the size and/or the density of the ALT elements, as observed by the video camera element, increases (the second case of the distance, generally corresponds to the cases shown in FIGS. 4B, 7, and 9). In the second case of the distance, movements of the person's body, including those associated with heartbeats and respiration, generally result in changes in one or more of the position, shape, size, or number of the ALT elements in addition to the changes in the illumination distribution of the ALT elements in the video frames captured by the video camera element.

Comparison of the data shown in FIG. 5A (corresponds to the first case of the distance discussed above) and FIGS. 1 and 4A (correspond to the second case of the distance discussed above) indicates that the respiration process becomes more pronounced in the ALT data the smaller the distance between a person and the light source and/or the camera elements of a system according to the technology disclosed in this patent document. Increase of the relative contribution of respiration in the ALT data in the second case of the distance compared to the first case of the distance indicates that the relative contribution of the changes in the position, and/or the shape, and/or the size, and/or the number of the ALT elements associated with respiration into ALT data increases with decreasing the distance between the person and the light source and/or the camera elements of a system according to the technology disclosed herein.

Although the patterns of the Kinect-generated light spots (ALT elements) shown in FIGS. 4B, 5B, 7, 9, and 10 are not the patterns of subjective speckles which can be produced by observing a single laser spot, the same interference phenomena which can lead to formation of a speckle pattern by using a single laser beam and the corresponding laser light spot can contribute to the illumination distribution within each individual element of the additional light texture, as captured by the video camera element, along with the contributions to the illumination distribution within the element due to the geometric (e.g. tilt, curvature) as well as various physical properties (e.g., optical properties) of different parts and/or surfaces of a human body.

Some of the other example embodiments of the devices and systems according to the technology disclosed in this patent document use Intel RealSense cameras (Intel Corporation, U.S.) and will be discussed below.

Light emitters of RealSense cameras can be used as light source elements in various embodiments of devices and systems according to the technology disclosed in this patent document. Systems according to the technology disclosed herein can use RealSense cameras themselves or use another camera such as, for example, a Raspberry Pi NoIR camera as a video camera element for video frames capture.

Systems and methods according to the technology disclosed in this patent document can work with different types of static light patterns generated by various devices such as Microsoft Kinect for Xbox 360 (see above; see, e.g., FIGS. 4B, 5B, 7, 9, and 10), and Intel RealSense R200 cameras (see below; see, e.g., FIGS. 11 and 13A-13B; for example, the paper [Keselman L., Woodfill J. I., Grunnet-Jepsen A., Bhowmik A. "Intel® RealSense™ Stereoscopic Depth Cameras", retrieved on Jun. 20, 2017 from the Internet: <URL: https://arxiv.org/pdf/1705.05548.pdf> (arXiv: 1705.05548v1); the paper was posted to arxiv.org on May 16, 2017] provides the following description: "Each R200 also includes an infrared texture projector with a fixed pattern . . . . The pattern itself is designed to be a high-contrast, random dot pattern"). Systems and methods according to the technology disclosed in this patent document can also work with any dynamically projected patterns, such as, for example, the ones generated by Intel RealSense F200 cameras (see below; see, e.g., FIGS. 12 and 14A-14B).

Note that the common feature of such different types of light patterns which can be used by the systems, devices and methods according to the technology disclosed in this patent document is illumination of a set of areas (e.g., one or more areas) of an object (e.g., a body of a person), wherein the said illumination leads to creating or increasing illumination of the said areas relative to other areas of the object (e.g., the person's body), which can be described as creating or increasing illumination contrast between the areas illuminated by the light source element relative to areas that are not illuminated by the light source element, as observed in video frames captured by a video camera element of a system according to the disclosed technology (the illumination or the illumination contrast can be measured, for example, using video frame data as, for example, discussed above). The said illumination creates elements of the additional light texture (e.g., light spots (such as the light spots (e.g., 950 and 960) shown in the images 970 and 980 in FIG. 9)). As discussed above, movements of the person's body, including those which are related to the person's respiration and/or heartbeat(s), can lead to variations in one or more of the illumination, shape, size, or position/location of the elements of the additional light texture (and/or to variations in one or more of an illumination distribution, a shape distribution, a size distribution, or a location distribution of the elements of the additional light texture) and/or to variations in the number of those elements, as observed by a video camera element (see, e.g., FIGS. 9 and 10 and the related discussion above). The said variations are captured, at least in part, by the video camera element in a set of video frames which are processed by a computing element according to a method according to the technology disclosed in this patent document to result in a set of numeric values (referred to as the "ALT data") which can be further processed to obtain numeric values containing or representative of the information related to a physiologic parameter of the person and/or to display at least a part of the set of numeric values using a graphical representation such as a 2D or a 3D plot or an alphanumeric representation or any other form of visual or audio representation.

As we have discussed above, one of the possible implementations of a method according to the technology disclosed in this patent document includes obtaining sum of absolute differences (SAD) numeric values generated by a video encoder for the video frames captured by a video camera. Alternatively to using a video encoder data, calculation of the sum of absolute differences numeric values can be incorporated in the methods according to the technology disclosed herein in other ways, as we describe below.

As a possible implementation, SAD-generating computations can include iterating over pixels of a given captured video frame, for each pixel of the video frame calculating a difference between a numeric value of a certain kind associated with that pixel (for example, that value can be included/stored in the video frame data of the video frame (e.g., in the pixel itself), e.g. that value can correspond to (e.g., be equal to) the pixel's grayscale level or the value corresponding to intensity of blue (or red or green) color of the pixel; for example, that value can be obtained as a result of calculations involving one or more numeric values in the video frame data; if, for example, the pixel contains a single numeric value (e.g., the one corresponding to a grayscale level of the pixel), then the numeric value associated with the pixel can be, for example, equal to the single numeric value contained in the pixel or can be obtained in the course of computations involving that single numeric value included in the pixel (the computations can include, for example, computing an average numeric value of the grayscale levels of the pixel and one or more of its neighboring pixels and/or scaling the grayscale level of the pixel using a scaling factor)) and a numeric value associated with a corresponding pixel of another captured video frame, calculating an absolute value of the found difference, and adding the calculated absolute value to the sum of the absolute values calculated on the previous step of the iteration process (at the beginning of the iteration process the value of the sum can be initialized to zero, for example). The sum of absolute differences numeric value thus computed (referred to as the "mSAD" value) for a given video frame is analogous to the sSAD value obtained from the data generated by a video encoder. Two pixels belonging to different video frames can be designated as corresponding to one another if these pixels are located in the same pixel row and in the same pixel column within the video frames; other rules can be used to designate the corresponding pixels; the corresponding pixels can occupy different pixel rows and/or different pixel columns within the video frames. An mSAD value can be calculated for any part of a video frame (ranging from the whole video frame to a single pixel of the video frame) following the procedure described above.

The mSAD value computed for a (whole) captured video frame, as described above, is a simple metric of the similarity between that video frame and another (whole) video frame (called the "reference" video frame) whose data were used in the computation of the mSAD value. The mSAD value is the "Manhattan distance" between the two video frames computed using numeric values associated with the video frame pixels of those video frames. An mSAD value computed for a video frame (or a part of the video frame) represents a measure of motion in the video frame (or in its part for which the mSAD value was computed).

The Manhattan distance (also referred to as taxicab distance), D, between vector p having coordinates of its end point $(p_1, p_2, \ldots, p_n)$ and vector q having coordinates of its end point $(q_1, q_2, \ldots, q_n)$ in an n-dimensional real vector space with a (fixed) Cartesian coordinate system (the origin points of both vectors p and q are at the center of the coordinate system, $(0, 0, \ldots, 0)$), is the sum of the lengths of the projections of the line segment between the end point of the vector p and the end point of the vector q onto the coordinate axes of the coordinate system. More formally, $D(p, q) = \|p-q\|_1 = \Sigma_{i=1}^{n} |p_i - q_i|$. For example, the Manhattan (taxicab) distance between $(p_1, p_2)$ and $(q_1, q_2)$ is $|p_1 - q_1| + |p_2 - q_2|$.

A pixel of a video frame is, generally, one or more numeric values (a set of numeric values) that correspond to a physical pixel of a sensor (or a group (one or more) of pixels or other elements of the sensor) of a video camera (e.g., a video camera element of a system according to the disclosed technology that was used to obtain the video frame). Let's consider two video frames, video frame P and video frame Q. Coordinates of the vector p (vector p corresponds to the video frame P) can correspond to (e.g., be equal to) numeric values associated with one or more pixels of the video frame P. For example, the numeric values can be contained in the data (video frame data) of the video frame P. For example, the data of the video frame P can be provided by a camera (e.g., a video camera element of a system according to the disclosed technology that was used to obtain the video frame P). Each coordinate $p_i$ of the vector p corresponds to (e.g., equals to) a numeric value associated with a pixel of the video frame P. For example, the numeric value can be contained in the data (video frame data) of the video frame P (e.g., in the pixel itself). For example, the video frame data of the video frame P can be received (e.g., by a computing element of a system according to the disclosed technology) from a camera (e.g., a video camera element of the system according to the disclosed technology). Similarly, coordinates of the vector q (vector q corresponds to the video frame Q) can correspond to (e.g., be equal to) numeric values associated with one or more pixels of the video frame Q. For example, the numeric values can be contained in the data (video frame data) of the video frame Q. For example, the data of the video frame Q can be provided by a camera (e.g., a video camera element of a system according to the disclosed technology that was used to obtain the video frame Q). Each coordinate $q_i$ of the vector q corresponds to (e.g., equals to) a numeric value associated with a pixel of the video frame Q. For example, the numeric value can be contained in the data (video frame data) of the video frame Q (e.g., in the pixel itself). For example, the video frame data of the video frame Q can be received (e.g., by a computing element of a system according to the disclosed technology) from a camera (e.g., a video camera element of the system according to the disclosed technology).

Similarly, a SAD value generated by a video encoder (e.g., a H.264 based one) for a macroblock of a video frame, which we have used above, is a measure of similarity between the macroblock and a corresponding macroblock of another video frame (the reference video frame), the "Manhattan distance" between these two macroblocks. Therefore, sSAD value can be viewed as "Manhattan distance" between two video frames computed using video encoder-generated data.

Similarly to the mSAD value computation described above, a SAD value generated by a video encoder for a macroblock of a video frame can be obtained by calculating, for each pixel of the macroblock, an absolute difference between a numeric value associated with the pixel and a numeric value associated with a pixel of a corresponding macroblock of a reference video frame and finding a sum of these absolute difference values.

Note that the corresponding macroblocks (correspondence between the macroblocks is established, for example, by a video encoder) can generally have different position within the video frames containing the macroblocks. Also, two pixels for which an absolute difference between numeric values associated with the pixels is calculated can generally have different positions within the macroblocks containing the pixels. Two pixels used in an absolute value calculation can have different position within the corresponding video frames containing the pixels too in an implementation of a method according to the technology disclosed in this patent document whether it uses data generated by a video encoder or not.

For an implementation of a method according to the technology disclosed herein, the numeric value associated with a pixel of a video frame can be taken directly from the video frame data for the pixel (e.g. pixel's grayscale or blue or red or green or cyan or yellow or magenta or black level) or obtained as a result of calculations using one or more of the video frame data values for the pixel and/or other pixels of the video frame (e.g. an average of the grayscale level values of the pixel and all or some of its neighboring pixels in the video frame).

Note that although for any captured video frame the methods according to the technology disclosed in this patent document typically use the one immediately preceding it as the reference video frame in the computations of SAD and/or XYabs and/or sSAD and/or mSAD values, any one of the captured video frames can be used as the reference video frame for any other captured video frame for the data generation purposes according to any of the methods according to the technology disclosed herein.

Moreover, by letting the reference video frame to be separated from a given video frame in the video frames set by one or more video frames one can obtain mSAD data, for example, corresponding to different timescales or different effective frame rates. For example, video frames capture done at 100 frames per second rate (typically referred to as "fps"), which corresponds to 10 ms time interval between the consecutive video frames when the camera settings such as exposure duration are fixed (see, e.g., LISTING 1), for 30 seconds results in a video frames set having 3000 video frames. One can process video frames in this set by selecting for each video frame for which mSAD value is to be obtained the immediately preceding one as the reference video frame to produce mSAD data corresponding to 10 ms time interval between the video frames or 100 frames per second capture rate. One can form a sub-set of the collected set of the video frames by selecting each 10th video frame of the set. mSAD data obtained by processing the sub-set of the video frames by selecting for each video frame for which mSAD value is to be obtained the immediately preceding one in the sub-set as the reference video frame will correspond to 100 ms time interval between the mSAD data points or to the effective 10 frames per second rate.

Respiration, heartbeats and/or other movements of a person's body cause additional variations of the "Manhattan distance" between the captured video frames compared to the case when there are no body movements (and/or body-caused movements of other objects) in the scene. Thus, the computed sSAD and/or mSAD values, both of which represent the "Manhattan distance" between the captured video frames, contain information about the respiration and/or heartbeats and/or other movements of a person over the time period covered by the captured video frames.

Application of the artificial light texture to a person's body and/or to the objects surrounding the person can lead to a significant enhancement of the variations in the "Manhattan distance" between the captured video frames which (the variations) are associated with the respiration and/or heartbeats and/or other movements of the person compared to the case when the artificial light texture is absent (e.g. when the ALT-generating light emitter is switched off) and otherwise identical data collection and data processing steps are performed.

Provided that video frames are captured at equal time intervals, the computed sSAD and/or mSAD values can be viewed as the integral of (the sum of) the rate of change of the numeric values which are associated with the video frame pixels and used in the sSAD and/or mSAD values computations.

Note that the methods according to the technology disclosed in this patent document can use SAD and/or XYabs and/or mSAD and/or sSAD values for a measure of motion in a video frame or in a part of the video frame, as well as any other measure of motion such as the one based on calculation of a sum of lengths of motion vectors computed for a video frame or a part of the video frame using, for example, data generated by a video encoder or by an optical flow-based method, irrespective of the type of the additional light texture (e.g., static or dynamic and/or a type of a (illumination) pattern or patterns used in the light texture) created by the systems according to the technology disclosed herein.

Note that the main reason for using the absolute value of the difference between two numeric values associated with the pixels of the video frames in some of the implementations of the methods according to the technology disclosed in this patent document is that we are interested in the amplitude of the change between the said values rather than in the sign (e.g., positive vs. negative) of the change. Therefore, the absolute value calculation operation can be replaced by another operation which has the same effect of providing information about the magnitude rather than the sign of the change between the numeric values associated with the pixels of the video frames in other implementations of the methods according to the technology disclosed in this patent document. For example, one can perform calculation of the squared value of the difference, $difference^2$, instead of calculating its absolute value, |difference|, in an implementation of a method according to the technology disclosed herein.

Figure 11:
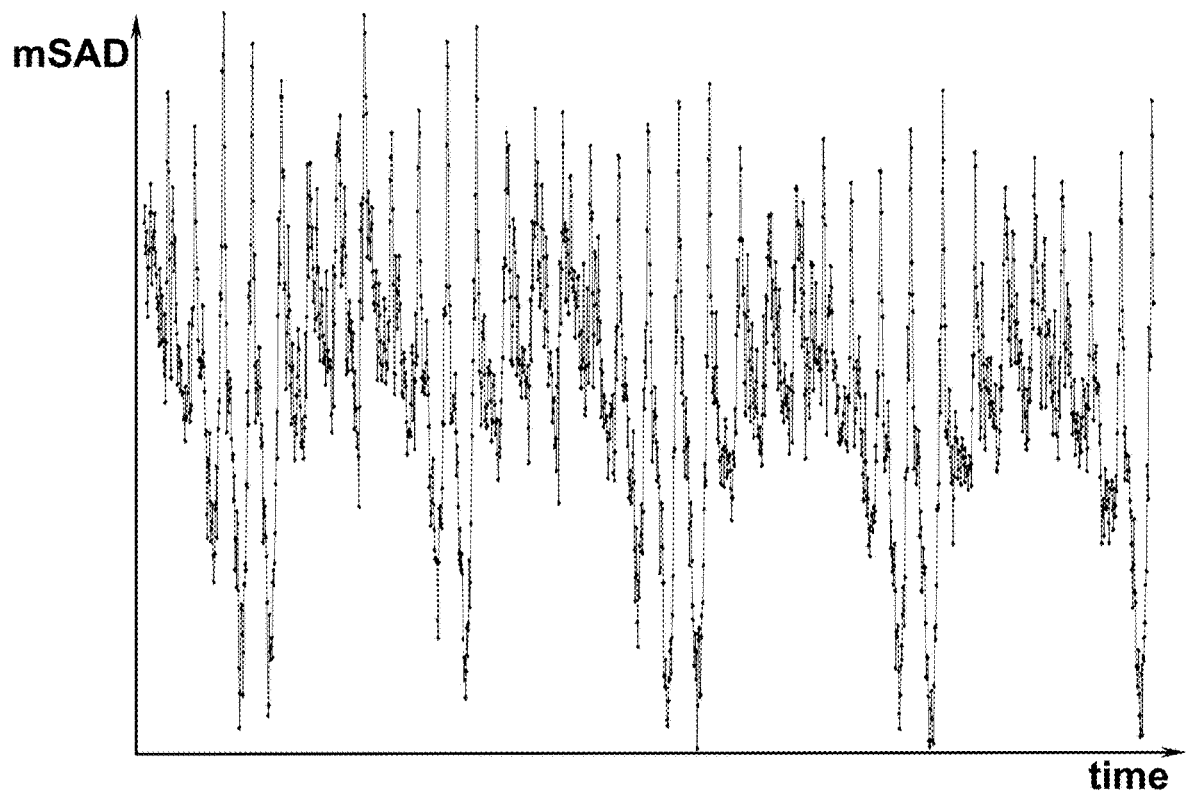
FIG. 11 shows example data obtained using an embodiment of a system and an implementation of a method according to the technology disclosed herein.
Figure 11:
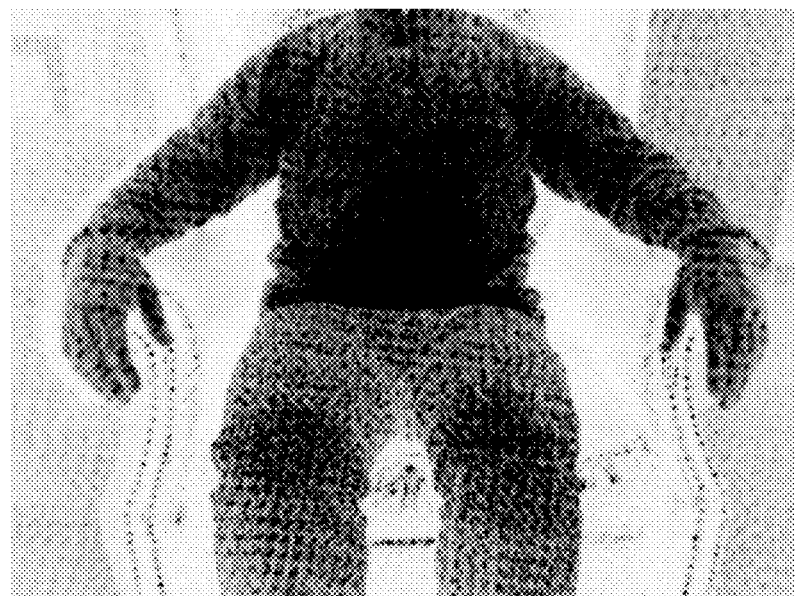
Figure 12:
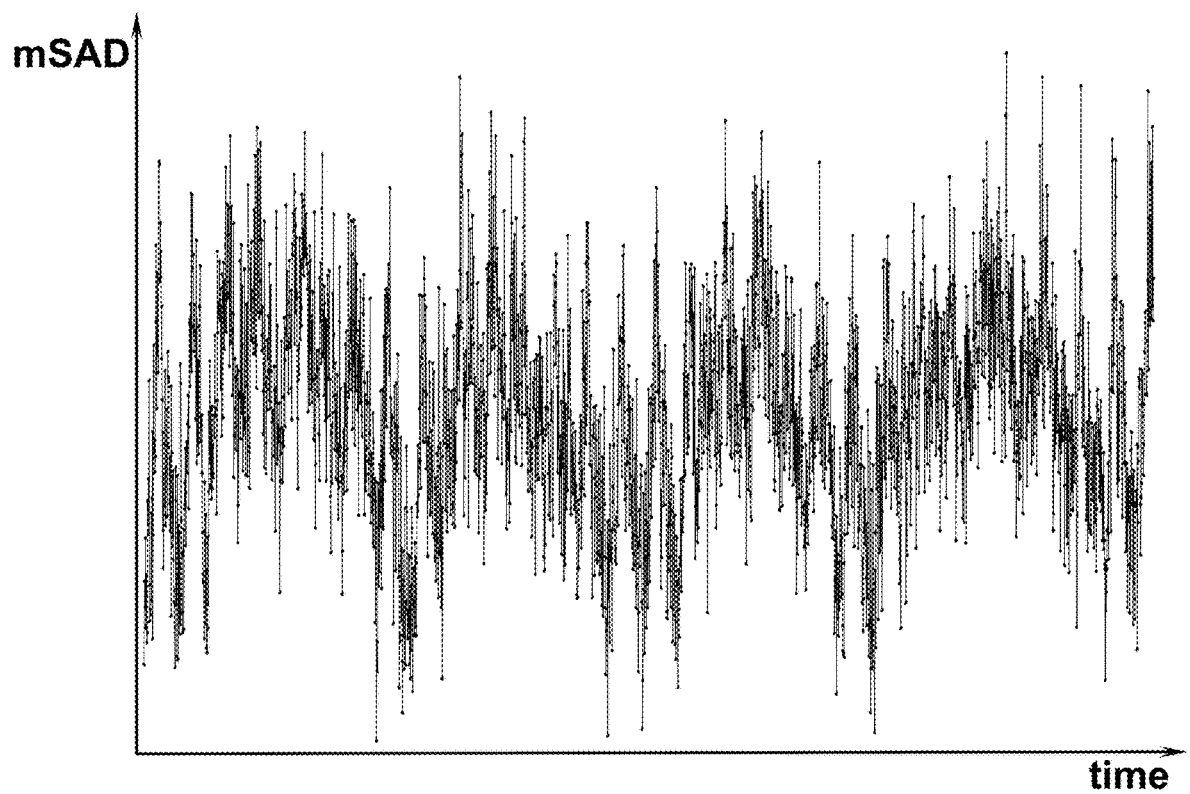
FIG. 12 shows another example data obtained using an embodiment of a system and an implementation of a method according to the technology disclosed in this patent document.
Figure 12:

The raw mSAD ALT data are shown in the FIGS. 11, 12, 13A-13B, and 14A-14B by lines connecting the data points (the computed mSAD values for the captured video frames shown by dots). Snapshots of the scene captured by the video camera elements are shown below the corresponding data plots in FIGS. 11 and 12. Two pixels which were designated as corresponding to one another in the computations of the mSAD values shown in FIGS. 11, 12, 13A-13B, and 14A-14B were located in the pixel rows having the same number and in the pixel columns having the same number within two different video frames used for a mSAD value computation. We used grayscale level of a pixel as the numeric value associated with the pixel in mSAD values computations. Also, for any given video frame we used the one immediately preceding it as the reference video frame for computations of the mSAD values shown in FIGS. 11, 12, 13A-13B, and 14A-14B.

mSAD data shown in FIG. 11 were obtained using the light emitter and IR video stream of an R200 Intel RealSense camera running at 60 frames per second frames capture rate. A snapshot of the scene taken from the R200 IR video stream is shown below the mSAD data plot in FIG. 11. A person is sitting in an armchair at about 3 feet distance from the R200 camera. mSAD data in FIG. 11 captured four full respiration cycles of the person (and a small part of a fifth respiration cycle towards its end, as shown at the very beginning of the dataset shown in FIG. 11). Numeric values for the heart rate and/or respiration rate of the person can be obtained, for example, via Fourier analysis of the mSAD data or via a correlation type of analysis of the mSAD data (e.g., via a self-correlation of a single series of mSAD values).

mSAD data in FIG. 12 were obtained using the light emitter and IR video stream of a F200 Intel RealSense camera running at 100 frames per second rate. A snapshot of the scene taken from the F200 IR video stream is shown below the mSAD data plot in FIG. 12. A person is sitting on a chair at about 3 feet distance from the F200 camera. mSAD data in FIG. 12 captured four full respiration cycles of the person.

Computing element (a desktop PC) was executing the same video frames processing algorithm described above to generate mSAD data both for F200 and for R200 cameras (FIGS. 11 and 12, respectively) in real time.

In the case of the dynamically projected patterns, as demonstrated on the example of using a F200 Intel RealSence device (FIG. 12), body movements, including the ones associated with heartbeats and respiration, lead to the changes in the non-uniform illumination distribution of the scene that is dynamically created by the light emitter of the F200 device, as captured by the infrared camera of the F200 device (the captured non-uniform (dynamic) illumination distribution forms the artificial light texture, as observed in the captured video frames), which otherwise would have been absent provided the absence of any motion in the scene.

One can note that there is a higher level of noise in the mSAD data in FIG. 12 compared to the mSAD data in FIG. 11. The higher noise level can be explained by lack of synchronization between the patterns generation by the light emitter of the F200 camera and heartbeats and respiration of the person meaning that consecutive heartbeats and/or consecutive respiration cycles correspond to different (average) exposure of the body areas to the camera's dynamically projected light patterns and also that different (but equal in duration) parts of a heartbeat time interval and/or of a respiration cycle duration correspond to different exposure of the body areas to the camera's patterns.

Note that, similarly to the first embodiment of a system according to the technology disclosed in this patent document, the distance between the F200 or R200 camera and the person can affect how pronounced the heartbeat signal will be during the respiration events. Generally, the closer the camera gets to the person the less pronounced the heartbeat signal component in the ALT data becomes during respiration events. Note also that at a large enough distance between the camera and the person there can be virtually no discernable pulse or respiration signal in the ALT data. Adjustments of the camera's position relative to a subject can be made, for example, based on observing visualizations of the collected ALT data.

Figure 13A:
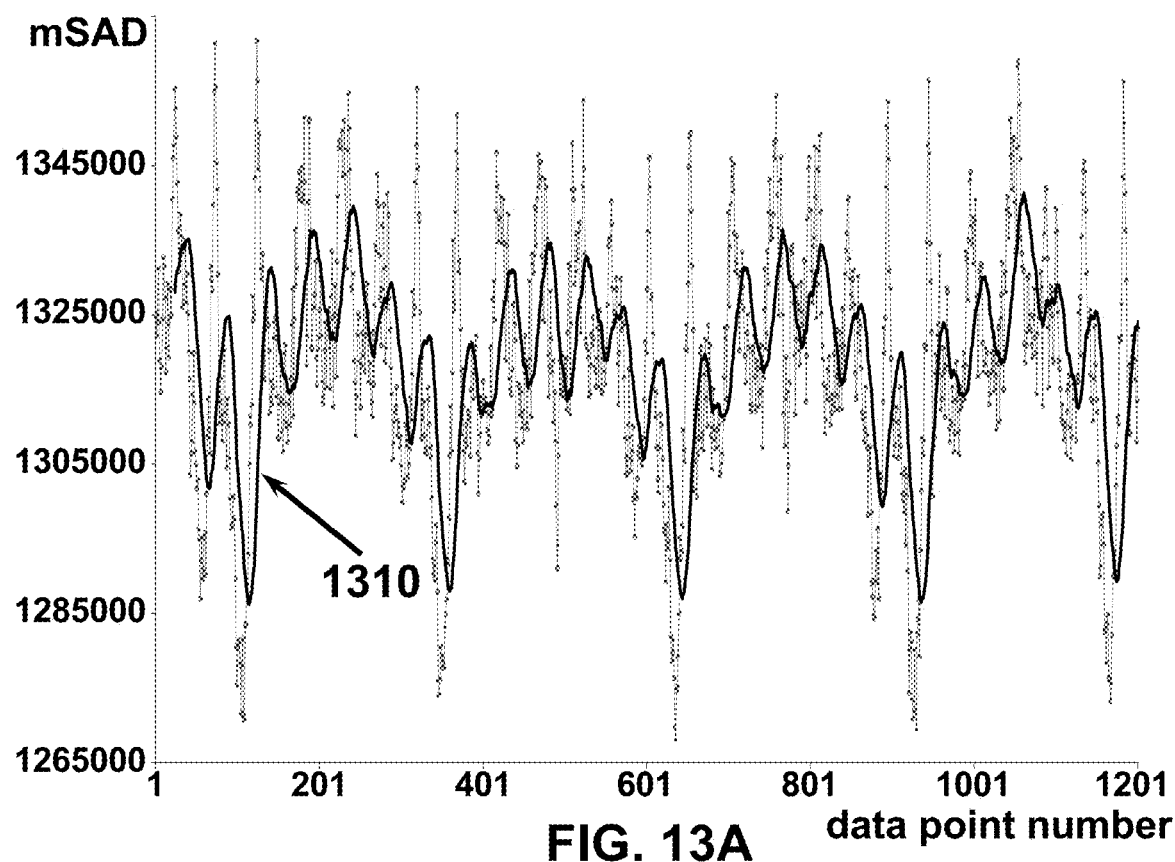
FIGS. 13A-13B show an example dependence of the data obtained by a system according to the technology disclosed in this patent document using a method according to the technology disclosed herein on the distance of the system from a person.
Figure 13B:
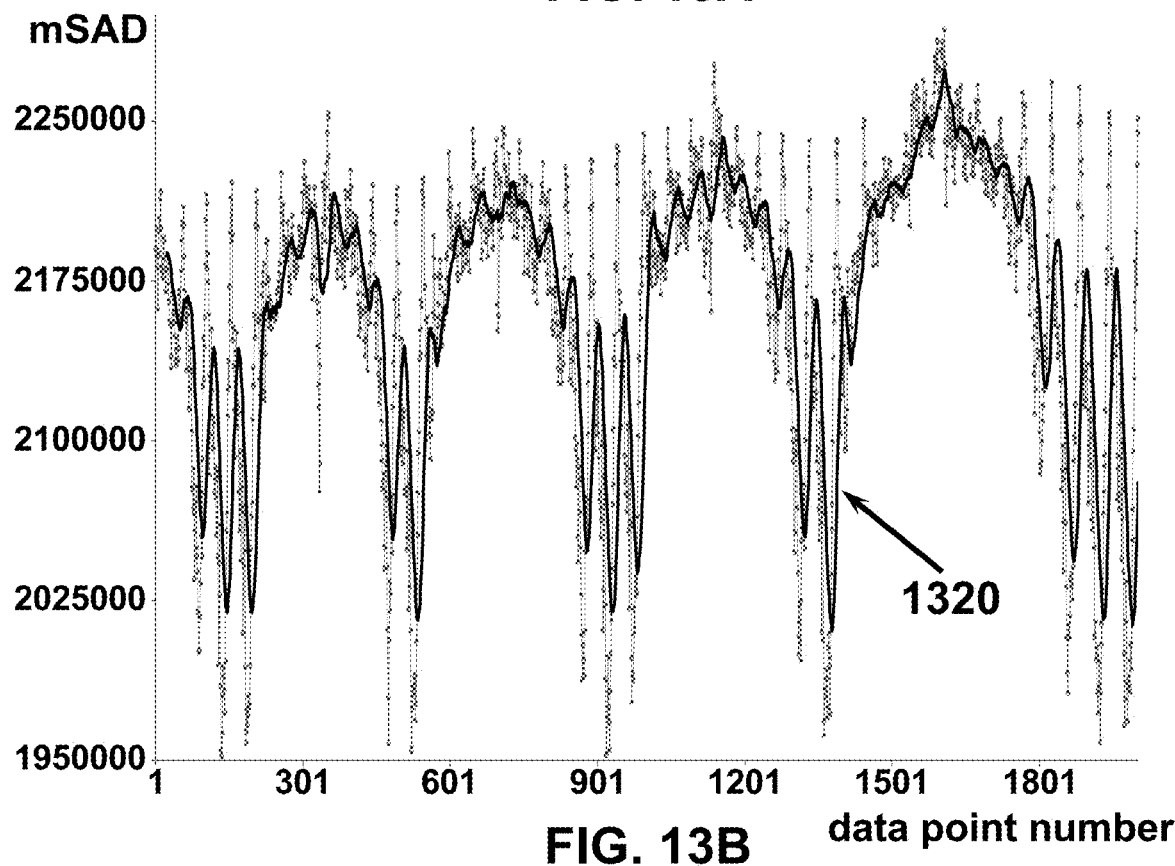

FIGS. 13A and 13B show mSAD data obtained using the IR light emitter and IR video stream of a R200 Intel RealSense camera running at 60 frames per second rate for two distances of the R200 camera from a person sitting in an armchair in front of the R200 camera, as shown in FIG. 11. FIG. 13A corresponds to the distance of ~152 cm (60 in) between the camera and the backrest of the armchair. FIG. 13B corresponds to the distance of ~102 cm (40 in) between the camera and the backrest of the armchair. mSAD data in both FIG. 13A and FIG. 13B captured four full respiration cycles of the person. Raw mSAD data are shown in FIGS. 13A and 13B by gray lines connecting the mSAD data points. Black lines 1310 and 1320 in FIG. 13A and FIG. 13B, respectively, are 24-points moving averages of the raw mSAD data. As data in FIGS. 13A and 13B demonstrate, variations in the mSAD data related to heartbeats are less pronounced during respiration cycles in FIG. 13B compared to FIG. 13A. One can also say that the relative contribution of the respiration into the mSAD data increases with decreasing the distance between the person and the video camera and the light source elements (both of these elements are housed within the common enclosure of the R200 unit in this case).

Figure 14A:
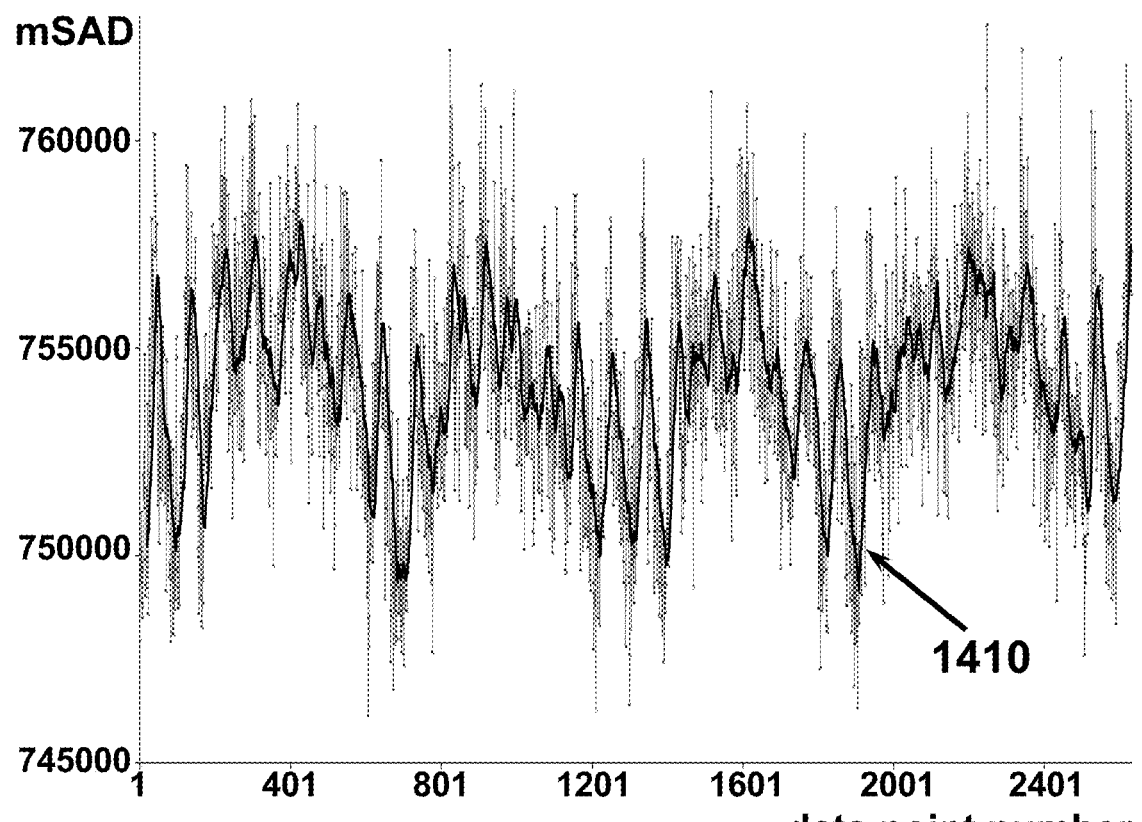
FIGS. 14A-14B show another example dependence of the data obtained by a system according to the technology disclosed in this patent document using a method according to the technology disclosed herein on the distance of the system from a person.
Figure 14B:
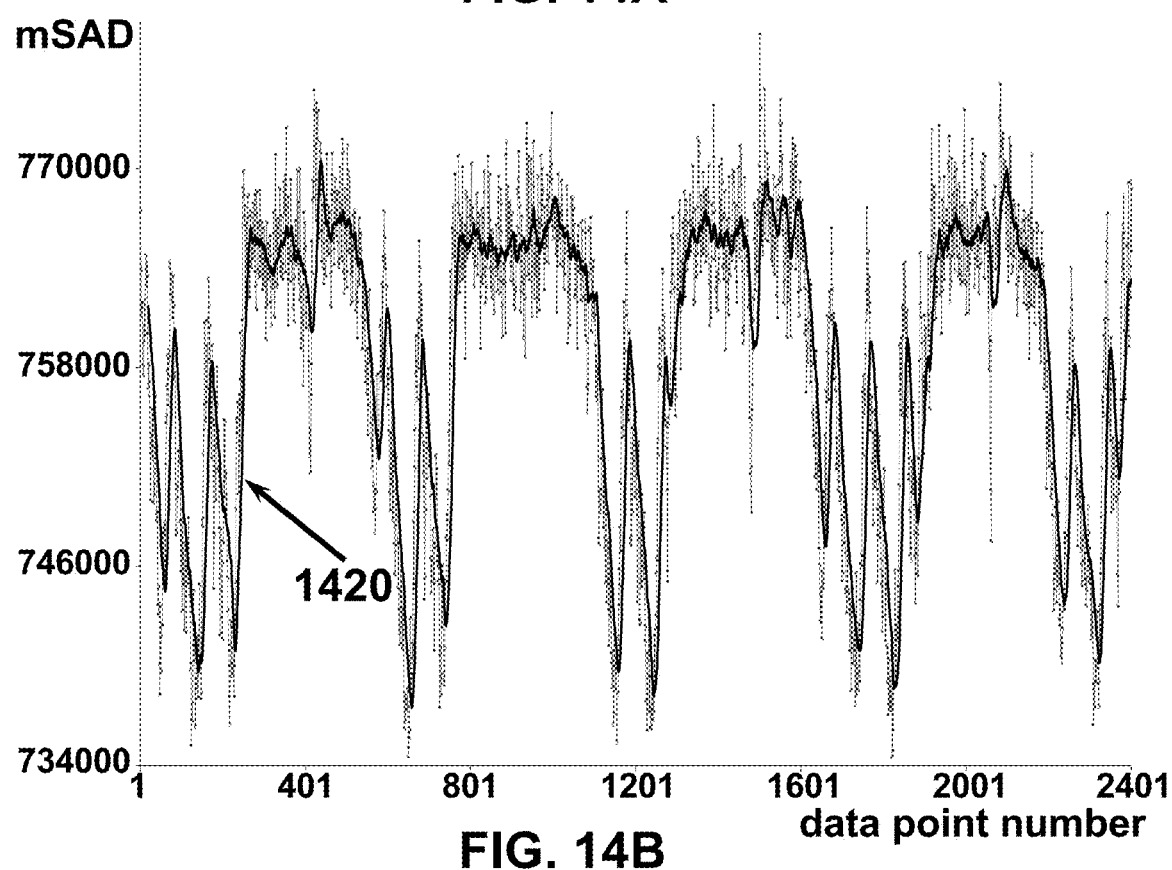

FIGS. 14A and 14B show mSAD data obtained using the IR light emitter and IR video stream of a F200 Intel RealSense camera running at 100 frames per second rate for two distances of the F200 camera from a person sitting on a chair in front of the F200 camera, as shown in FIG. 12. FIG. 14A corresponds to the distance of ~119 cm (47 in) between the camera and the backrest of the chair. FIG. 14B corresponds to the distance of ~81 cm (32 in) between the camera and the backrest of the chair. mSAD data in both FIG. 14A and FIG. 14B captured four full respiration cycles of the person. Raw mSAD data are shown in FIGS. 14A and 14B by gray lines connecting the mSAD data points. Black lines 1410 and 1420 in FIG. 14A and FIG. 14B, respectively, are 20-points moving averages of the raw mSAD data. As data in FIGS. 14A and 14B demonstrate, variations in the mSAD data related to heartbeats are less pronounced during respiration cycles in FIG. 14B compared to FIG. 14A. One can also say that the relative contribution of the respiration into the mSAD data increases with decreasing the distance between the person and the video camera and the light source elements (both of these elements are housed within the common enclosure of the F200 unit in this case).

As different embodiments of the technology disclosed in this patent document described above demonstrate, systems and methods according to the technology disclosed herein do not rely on any particular kind of light pattern (statically and/or dynamically projected). As comparison of the data shown in FIGS. 1 and 5A, 13A and 13B, and 14A and 14B demonstrates, the systems and methods according to the technology disclosed in this patent document generate data exhibiting the same qualitative dependence on the distance between a person and the video camera element and/or the light source element. This dependence is related to the changes in responses of the elements of the additional light texture to the movements of the person's body, including the ones that are related to the person's heartbeats and/or respiration, as captured by a video camera element, which occur with changes of the distance between the person and the light source element and/or the video camera element, as illustrated above for one of the example embodiments of a system according to the technology disclosed herein (see FIGS. 9 and 10, and the related discussion above).

As demonstrated above, embodiments of the systems according to the technology disclosed in this patent document can use inexpensive hardware components such as, for example, a Raspberry Pi single-board computer and a Pi NoIR camera, and are compatible with light emitters of different consumer electronics devices traditionally used for depth sensing applications, such as, for example, Kinect for Xbox 360, Intel RealSense R200 and F200 cameras, which generate vastly different, both in terms of the spatial characteristics and in terms of the temporal characteristics, light patterns.

As demonstrated above, methods according to the technology disclosed herein can use algorithms based on the differential (between video frames) data processing and can use different measures of motion in a video frame (relative to another video frame). Note that the methods according to the technology disclosed in this patent document can be applied to the video frames that have not been processed by a video encoder ("raw" video frames), as well as to the video frames that have been processed by a video encoder ("encoded" video frames). The methods according to the technology disclosed herein enable one to use inexpensive/cheap video camera and computing elements and provide vast degree of compatibility with and independence from particular spatial and temporal characteristics of the light patterns generated by various light sources.

As demonstrated above, for the purpose of obtaining information related to the said group of physiologic parameters, systems and methods according to certain embodiments of the technology disclosed in this patent document do not use or obtain any depth or distance information or depth or distance values (e.g., numeric values) or depth or distance data that are encoded in the light patterns projected by light emitters (light source elements) and captured by camera elements (e.g., infrared cameras) of the depth sensing devices such as, e.g., Kinect and RealSense cameras used in some example embodiments of the systems according to the disclosed technology. For the purpose of obtaining information related to the said group of physiologic parameters, systems and methods according to some embodiments of the technology disclosed in this patent document do not use or obtain any other depth or distance information or depth or distance values (e.g., numeric values) or depth or distance data that are related to or are associated with any object, including the body of a person or any part of the said body, in a scene that is captured in a video frame by a video camera (e.g., a video camera element of a system according to the disclosed technology) or a scene that is observed by a video camera (e.g., a video camera element of a system according to the disclosed technology) or a scene that in a field of view of a camera (e.g., a video camera element of a system according to the disclosed technology). For the purpose of obtaining information related to the said group of physiologic parameters, systems and methods according to certain embodiments of the technology disclosed in this patent document do not use or obtain any information about any distance.

As also demonstrated above, for the purpose of obtaining information related to the said group of physiologic parameters, systems and methods according to certain embodiments of the technology disclosed herein do not use or obtain any information about or any numeric values or data related to (or associated with) a position (e.g., coordinate(s) and/or distance(s)) of any element of an image of a scene, the image being captured in a video frame by a video camera (e.g., a video camera element of a system according to the disclosed technology), within the said image. For the purpose of obtaining information related to the said group of physiologic parameters, systems and methods according to certain embodiments of the technology disclosed herein do not use or obtain any information about or any numeric values or data related to (or associated with) a position (e.g., coordinate(s) and/or distance(s)) of any feature of any function computed or calculated or otherwise obtained using data of any video frame captured by a video camera (e.g., a video camera element of a system according to the disclosed technology) within any of the video frames captured by the video camera.

As described above, certain measures of motion that can be used by systems and methods according to the technology disclosed herein use distance values (e.g., lengths of motion vectors or lengths of projections of a motion vector on one or more axes of a coordinate system) that relate an element of a first video frame (e.g., a pixel or a macroblock of the first video frame) and an element of a second video frame (e.g., a pixel or a macroblock of the second video frame).

As demonstrated above, systems and methods according to the disclosed technology do not require an area of skin of a subject to be exposed to a camera or to any other device. The camera of a system according to the disclosed technology can be focused on any part of the body of a subject which can be, for example, completely covered by one or more covering items (e.g., by a blanket or clothes, including loose-fitting ones; the camera can be focused, for example, on the back or on the legs of the subject wearing clothes that are completely covering the back and/or the legs of the subject). Accordingly, some embodiments of the systems and/or methods according to the disclosed technology do not use or obtain any information and/or any data about any changes in (or of) color of skin of a person (e.g., changes which can be observed by a person and/or captured by a video camera when, for example, the skin is uniformly illuminated by white light) which (changes) are caused by the pulse (heartbeats) of the person or/and by any other physiologic process in the person. One can say that some embodiments of systems, devices, and methods according to the disclosed technology refrain from obtaining or using any information about any changes or variations of skin color of a subject (e.g., a person) which are cause by the heartbeats of the subject.

Systems, devices and methods according to the technology disclosed in this patent document also do not require a subject to be in line of sight of a camera.

The preferred embodiment of a system according to the technology disclosed in this patent document includes a light source element which illuminates (which is configured to illuminate) one or more areas of a person's body by creating light spots on those areas. Further, the light source element has at least one capability from: a capability to change a distance at least between two of the light spots, a capability to change a size of at least one of the light spots, a capability to change a shape of at least one of the light spots, or a capability to change illumination intensity of at least one of the light spots. The preferred embodiment of a system according to the technology disclosed herein also includes a video camera element which has at least one capability from: a capability to change the rate of acquisition of video frames, or a capability to change the size of the video frames or a capability to change exposure duration of at least one video frame. The preferred embodiment of a system according to the technology disclosed in this patent document further includes a computing element capable of performing computations of the SAD and/or sSAD and/or mSAD and/or XYabs numeric values and/or computations of a sum of the lengths of motion vectors (e.g., generated by or using a video encoder or produced using an optical flow-based method of video frames analysis) for the video frames captured by the video camera element, Further, the computing element preferably has a capability to perform at least a part of the said computations using a graphics processing unit (GPU).

The computing element of a system or a device according to the disclosed technology can be one of or can include one of: an integrated circuit, a processor, a microprocessor, a multi-core processor, a graphics processing unit (GPU), an application-specific integrated circuit (ASIC), a field-programmable gate array (FPGA).

The video camera element of a system or a device according to the disclosed technology can be one of or can include one of: an infrared camera (e.g., a camera or a device or a light detector or a light sensor that is configured to or that is capable of producing or generating electric signals (e.g., using electrons and/or holes) using light (e.g., photons) of one or more wavelengths (or having or including one or more wavelengths) above approximately 700 nm or using light having one or more wavelengths between approximately 700 nm and approximately 1000 nm or using photons of one or more wavelengths between approximately 700 nm and approximately 1 mm), a visible-spectrum camera (e.g., an RGB camera; e.g., a camera or a light sensor or a light detector or device that is configured to generate electric signals using light (e.g., photons) of one or more wavelengths (or having or including one or more wavelengths) between approximately 400 nm and approximately 700 nm).

The sSAD, mSAD, XYabs, or a sum of the lengths of the motion vectors measures of motion in at least a part of a video frame that can be used by methods according to the disclosed technology play the role of measures of the said variations in one or more of the illumination, shape, size, or location of the elements of the additional light texture and/or measures of variations in the number of those elements, as observed by a video camera element of a system according to the disclosed technology. As such, these measures of motion are not the only ones which can be used in the methods according to the technology disclosed herein. Any other measure of motion in a video frame or in at least a part of a video frame can be used by the methods according to the technology disclosed herein.

The above-mentioned characteristics of the systems and methods according to the disclosed technology can be used to obtain information related to the functioning of the cardiovascular system of a person, particularly the information which is related to the duration of the time interval of propagation of a blood pressure wave (or pulse) between two points or areas of a subject as well as pulse wave velocity (PWV) characteristics of the cardiovascular system of the subject and/or blood pressure (systolic and/or diastolic) of the subject, in a non-contact and continuous fashion.

Pulse wave velocity (PWV), in the context of a cardiovascular system, is the velocity at which a pressure pulse of blood (or a pressure wave of blood; or, simply, a pulse of blood or wave of blood) propagates through the circulatory system of an organism (e.g., a human organism). The circulatory system can include an artery or a combined length of arteries. PWV is used clinically as a measure of arterial stiffness. Currently, measurement of carotid to femoral PWV (cfPWV) is the recommended method of PWV measurements. cfPWV is obtained by measuring duration of propagation of a blood pressure pulse between a first point on the carotid artery of a person and a second point on the femoral artery of the person. cfPWV is highly reproducible and can predict future cardiovascular events and all-cause mortality independent of conventional cardiovascular risk factors. cfPWV has been recognized by the European Society of Hypertension as an indicator of target organ damage and a useful additional test in the investigation of hypertension.

A system according to the technology disclosed in this patent document which can be used to obtain a value of a time interval (or a length or a duration of a time interval) of propagation of a blood pressure pulse (or a blood pressure wave) from a first point or area or part of a body (e.g., a body of a subject/person) to a second point or area or part of the body is referred to as a PWV system below. A PWV system can be also used, in some example embodiments, to obtain pulse wave velocity value(s) or data or pulse wave velocity-related information as well as blood pressure (e.g., systolic blood pressure and/or diastolic blood pressure) data or values. A PWV system can include, for example, a light source element (for example, the light emitter of an Intel RealSense camera such as a D435 or a D435i or a D455 camera), a video camera element (e.g., at least one of the infrared (IR) cameras of the Intel RealSense camera), and a computing element (e.g., a Microsoft Surface Go tablet or any other computer). For example, the video camera element of a PWV system and/or the light source element of the PWV system can be connected to the computing element of the PWV system using a wired or a wireless connection(s). Generally, any system according to the disclosed technology can be a PWV system. Generally, any device according to the disclosed technology can be a PWV device.

For the purpose of obtaining information related to the pulse wave velocity and/or blood pressure characteristics of the cardiovascular system of a person, the light source element of a system according to the disclosed technology illuminates (is configured to illuminate) one or more areas (a set of areas) of the person's body by, for example, projecting one or more light spots (a set of light spots) onto them. As described above, the said illumination creates elements of the additional light texture (also referred to as the artificial light texture) on at least a part of the body of the person. As described above, movements of the person, including those which are related to the person's heartbeats and respiration, including movements caused by propagation of a blood pressure wave (or a blood pressure pulse) along the body of the person (e.g., from a first point (or a rea or part) of the body to a second point (or area or part) of the body), can lead to variations in one or more of the illumination, shape, size, or location of the elements of the additional light texture and/or to variations in the number of those elements, as observed by a video camera element of a system according to the disclosed technology (or as observed or captured in video frames collected by the video camera element). The said variations can be captured, at least in part, by the video camera element in one or more video frames (a set of video frames) which can be processed by a computing element of the system according to a method according to the technology disclosed herein to result in one or more numeric values referred to as the "ALT data" which can be further processed to obtain numeric values representative of the information related to the duration of the blood pulse propagation as well as to PWV and/or blood pressure of the person.

For the purpose of obtaining information related to blood pressure pulse propagation characteristics (e.g., duration, velocity) of the cardiovascular system of a person, the said video frames processing can be done in the following example manner:

Two areas are selected in each video frame of a set of video frames captured by a video camera element of a system according to the disclosed technology. These areas are referred to as the first area and the second area below. For at least one of the first areas selected in the video frames, a first numeric value corresponding to (e.g., equal to or otherwise related to) a measure of motion in the area (e.g., the measure of motion in a first area can be determined relative to (or using) an area of another video frame (another video frame means a video frame other than the one which has the said first area)) is obtained (e.g., is computed). For at least one of the second areas selected in the video frames, a second numeric value corresponding to (e.g., equal to or otherwise related to) a measure of motion in the area is obtained (e.g., is computed; e.g., this or any other measure of motion in a second area can be obtained/computed relative to (or using) an area of a video frame other than the one which has the said second area selected in it or areas (same (e.g., having the same position within the video frames) or different (e.g., having different positions within the video frames)) of several video frames). Any measure of motion mentioned in this patent document as well as any other measure of motion can be used to obtain the first numeric value and the second numeric value just mentioned. The first and second numeric values are related to movements of the person's body caused by the heartbeats (including blood pressure waves created by the heartbeats) and/or respiration of the person, to the extent that such movements are captured in the said first and second areas of the video frames. The numeric values obtained for the first areas of the video frames are referred to as the first set of motion values, and the numeric values obtained for the second set of areas of the video frames are referred to as the second set of motion values. A part of the first set of motion values and a part of the second set of motion values that correspond to the same heartbeat are selected or identified. Parts of the first and second sets of motion values can be deemed corresponding to the same heartbeat if, for example, that heartbeat has the same serial number among the heartbeats captured in the first set of motion values as it has among the heartbeats captured in the second set of motion values when the heartbeats are counted starting from a common time reference for both sets of motion values. Parts of the first and second sets of motion values can be deemed corresponding to the same heartbeat if, for example, those parts correspond to the same time interval (e.g., were obtained using video frames having time stamps within that time interval). Within the said part of the first set of motion values, at least a first motion value is selected or identified and a video frame corresponding to the first motion value is identified or selected. Within the said part of the second set of motion values, at least a second motion value is selected or identified and a video frame corresponding to the second motion value is identified or selected. For example, a video frame corresponds to a motion value in the first (second) set of motion values if the motion value was determined for the first (second) area of the video frame. The video frame corresponding to the first motion value is referred to as the first frame below. The video frame corresponding to the second motion value is referred to as the second frame below. The first and the second frames are used to determine a time interval corresponding to (e.g., equal to or otherwise related to) the duration of propagation of a blood pressure wave between an area of the person's body captured in (or otherwise related to) at least one of the first areas of the video frames and an area of the person's body captured in (or otherwise related to) at least one of the second areas of the video frames. The time interval can be equal, for example, to the time interval between the first frame and the second frame (as determined, for example, using time stamps of the first and the second frames that are provided, for example, by the camera that obtained or captured the first and the second frames or by a computing element of a system according to the disclosed technology that received the first and the second frames from the camera), or can be obtained as a result of calculations involving time positions (e.g., time stamps mentioned above) of one or more of the video frames (including or excluding the first and the second frames). A numeric value representative of the pulse wave velocity can be obtained by using the determined time interval and a numeric value related to (e.g., equal to or otherwise associated with) a distance (e.g., a direct distance (e.g., a distance along a line or a curve) or an effective distance or a virtual distance) between the said area of the person's body captured in (or otherwise related to) at least one of the first areas of the video frames and the said area of the person's body captured in (or otherwise related to) at least one of the second areas of the video frames by, for example, dividing the numeric value related to the said distance by the determined time interval.

In some example embodiments, the first motion value corresponds to a minimum (e.g., a local (or a global) minimum) motion value in the first set of motion values. In some example embodiments, the first motion value corresponds to a maximum (e.g., a local (or a global) maximum) motion value in the first set of motion values. In some example embodiments, the first motion value corresponds to a maximum (or minimum) value or a maximum (or minimum) value of a slope or a rate of change (e.g., a local (or a global) maximum (or minimum) value or a local (or a global) maximum (or minimum) value of a slope or a rate of change) of a dependence of the motion values in the first set of motion values (or a dependence of a function (e.g., a motion average function or any other type of averaging or filtering function or any other type of function) of the motion values in the first set of motion values) on a parameter such as, for example, video frame number or time stamp of the frame for which the motion value in the first set of motion values was obtained or any other parameter. In some example embodiments, the first motion value corresponds to a motion value in the first set of motion values or to a value of a function of the motion values in the first set of motion values.

In some example embodiments, the second motion value corresponds to a minimum (e.g., a local (or a global) minimum) motion value in the second set of motion values. In some example embodiments, the second motion value corresponds to a maximum (e.g., a local (or a global) maximum) motion value in the second set of motion values. In some example embodiments, the second motion value corresponds to a maximum (or minimum) value or a maximum (or minimum) value of a slope or a rate of change (e.g., a local (or a global) maximum (or minimum) value or a local (or a global) maximum (or minimum) value of a slope or a rate of change) of a dependence of the motion values in the second set of motion values (or a dependence of a function (e.g., a motion average function or any other type of averaging or filtering function or any other type of function) of the motion values in the second set of motion values) on a parameter such as, for example, video frame number or time stamp of the frame for which the motion value in the second set of motion values was obtained or any other parameter. In some example embodiments, the second motion value corresponds to a motion value in the second set of motion values or to a value of a function of the motion values in the second set of motion values.

In some example embodiments of the technology disclosed in this patent document, video frames processing can be done in the following example manner for the purpose of obtaining information or data or numeric values related to blood pressure wave (or pulse) propagation characteristics (e.g., duration, velocity) of the cardiovascular system of a person:

In each video frame of a set of video frames (the set includes one or more video frames) captured by a video camera element of a system according to the disclosed technology, two areas of the video frame are selected or identified. These areas are referred to as the first area and the second area below. Alternatively, a first area is selected in each of a first number (one or more) video frames and a second area is selected in each of a second number of video frames (one or more video frames), wherein at least some or all of the video frames in which the first area is selected are different from the video frames in which the second area is selected. For at least one of the first areas selected or identified in the video frames, a numeric value corresponding to (e.g., equal to or otherwise related to) a measure of motion in the area is determined or obtained (e.g., computed). For example, a measure of motion in a first area of a video frame can be determined relative to and/or using an area of a different video frame. For at least one of the second areas selected or identified in the video frames, a numeric value corresponding to (e.g., equal to or otherwise related to) a measure of motion in the area is determined or obtained (e.g., computed). For example, a measure of motion in a second area of a video frame can be determined relative to and/or using an area of another video frame. Any measure of motion mentioned in this patent document as well as any other measure of motion can be used to determine or obtain the numeric values just mentioned. The said numeric values are related to movements of the person's body caused by the heartbeats (including blood pressure wave(s) created by the heartbeats) and/or respiration of the person, to the extent that such movements are captured in the said first and second areas of the video frames. The numeric values determined or obtained for the first areas of the video frames are referred to as the first set of motion values, and the numeric values determined or obtained for the second areas of the video frames are referred to as the second set of motion values. A part of the first set of motion values and a part of the second set of motion values that correspond to a same heartbeat are identified in or selected from the first and the second sets of motion values, respectively. Parts of the first and second sets of motion values can correspond to the same heartbeat if, for example, that heartbeat has the same serial number among the heartbeats captured in the first set of motion values as it has among the heartbeats captured in the second set of motion values when, for example, the heartbeats are counted starting from a common time reference for both sets of motion values. Parts of the first and second sets of motion values can correspond to the same heartbeat if, for example, those parts correspond to the same time interval (e.g., those parts were obtained using video frames having time stamps within that time interval). In certain example embodiments of the technology disclosed herein, time markers (or time values or time positions) are assigned to (or linked to or otherwise put into a relationship or correspondence with) motion values in the first set of motion values and motion values in the second set of motion values. The assigned time markers can be obtained, for example, using time stamps and/or other time indicators and/or markers of the video frames (or time stamps and/or other time indicators and/or markers that are in any way associated with the video frames) captured by the video camera element (for example, the time stamps can be assigned to the video frames by the camera itself or by a computer (e.g., a computing element of a system according to the disclosed technology)). In some example embodiments, time markers that are assigned to the motion values can be obtained, for example, using time stamps of the video frames that correspond to the motion values (for example, a video frame corresponds to a motion value in the first (second) set of motion values if the motion value was determined for the first (second) area of the video frame). In certain example embodiments, a time marker for a motion value from the second (first) set of motion values is equal to the time stamp of the video frame from the second (first) set of video frames for which the motion value was obtained (the motion value was obtained for the second (first) area of that video frame). The above operations produce a first set of time markers that corresponds to the first set of motion values; a first correspondence or a first discrete function between a motion value in the first set of motion values and a time marker in the first set of time markers is thus established. The above operations also produce a second set of time markers that corresponds to the second set of motion values; a second correspondence or a second discrete function between a motion value in the second set of motion values and a time marker in the second set of time markers is thus established. Some example embodiments of the disclosed technology further include interpolating the first discrete function between at least two motion values in the first set of motion values and two time markers corresponding to those motion values to produce an interpolated first discrete function. Some example embodiments of the disclosed technology also include interpolating the second discrete function between at least two motion values in the second set of motion values and two time markers corresponding to those motion values to produce an interpolated second discrete function. Any interpolation method can be used such as a linear or a polynomial or a spline interpolation method. In some example embodiments, the interpolation results in one or more additional motion values and one or more additional time markers corresponding to those additional motion values that are located between the points (motion values and corresponding time markers) for which (between which) the interpolation was performed. According to some example embodiments, a first time value is obtained or selected using one of the first discrete function or the interpolated first discrete function. According to some example embodiments, a second time value is obtained or selected using one of the second discrete function or the interpolated second discrete function. In some example embodiments, a time interval is determined using the first time value and the second time value. For example, the time interval can be equal to a difference between the first time value and the second time value. The determined time interval can correspond to (e.g., be equal to or otherwise related to) the duration of propagation of a blood pressure pulse between an area of the person's body captured in (or otherwise related to) at least one of the first areas of the video frames and an area of the person's body captured in (or otherwise related to) at least one of the second areas of the video frames. A numeric value related to the pulse wave velocity characteristic of the cardiovascular system of the person can be obtained, for example, by using the time interval and a numeric value related to (e.g., equal to or otherwise associated with) a distance (e.g., a physical distance (e.g., a distance along a line or along a curve) or an effective distance or a virtual distance) between an area or a part of the person's body captured in (or otherwise related to) at least one of the first areas of the video frames and an area or a part of the person's body captured in (or otherwise related to) at least one of the second areas of the video frames by, for example, dividing the numeric value related to the distance by the time interval.

In some example embodiments, the first time value corresponds to a minimum (e.g., a local (or a global) minimum) motion value of the first discrete function or of the interpolated first discrete function. In some example embodiments, the first time value corresponds to a maximum (e.g., a local (or a global) maximum) motion value of the first discrete function or of the interpolated first discrete function. In some example embodiments, the first time value corresponds to a maximum (or minimum) value of a slope or a rate of change (e.g., a local (or a global) maximum (or minimum) value of a slope or a rate of change) of the first discrete function or of the interpolated first discrete function. In some example embodiments, the first time value corresponds to a value of the first discrete function or to a value of the interpolated first discrete function.

In some example embodiments, the second time value corresponds to a minimum (e.g., a local (or a global) minimum) motion value of the second discrete function or of the interpolated second discrete function. In some example embodiments, the second time value corresponds to a maximum (e.g., a local (or a global) maximum) motion value of the second discrete function or of the interpolated second discrete function. In some example embodiments, the second time value corresponds to a maximum (or minimum) value of a slope or a rate of change (e.g., a local (or a global) maximum (or minimum) value of a slope or a rate of change) of the second discrete function or of the interpolated second discrete function. In some example embodiments, the second time value corresponds to a value of the second discrete function or to a value of the interpolated second discrete function.

Figure 15:
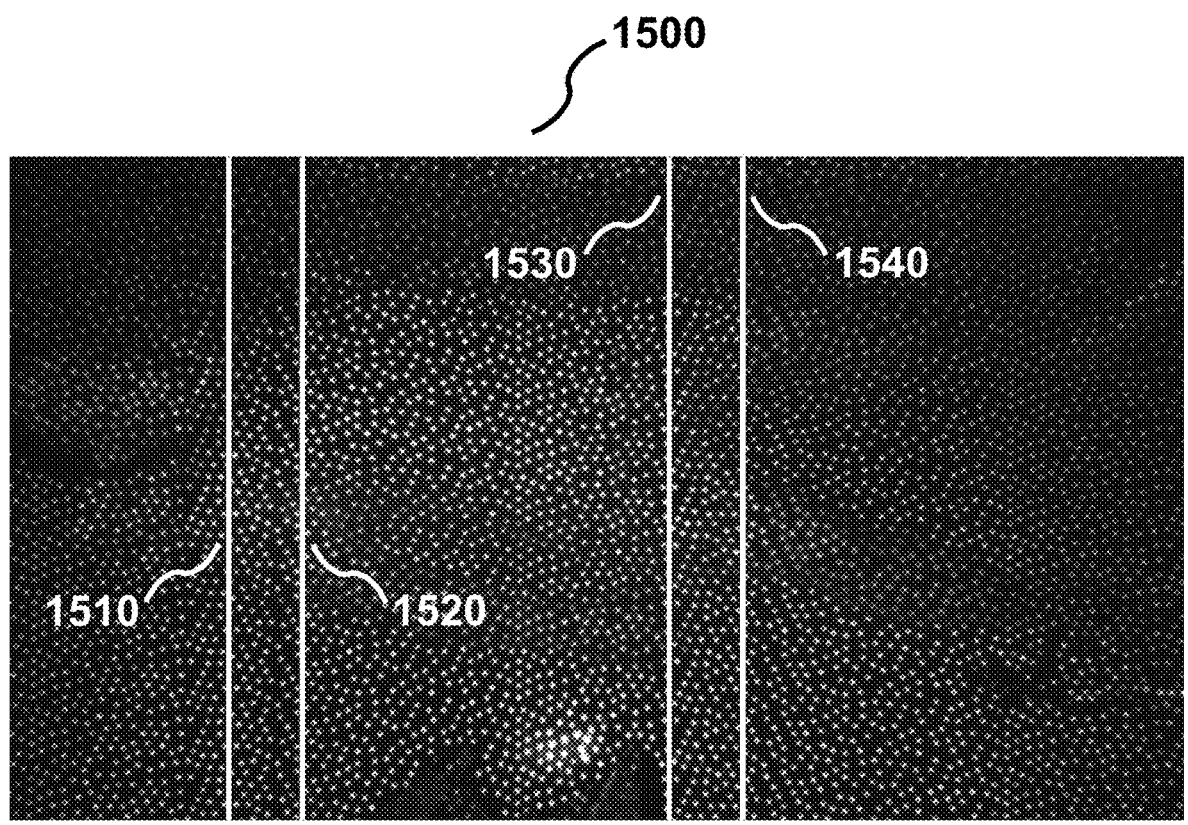
FIG. 15 illustrates an example video frame captured by a system according to the disclosed technology and showing a person lying on a firm surface.

FIG. 15 shows one of the IR video frames (video frame 1500) captured by the video camera element of a PWV system according to the disclosed technology. The frame shows a person lying on a firm surface. The first area of the video frame shown in FIG. 15 is the one between the lines 1510 and 1520 in FIG. 15. The second area of the video frame shown in FIG. 15 is the one between the lines 1530 and 1540 in FIG. 15. Note that, as shown in FIG. 15, both the first area and the second area of the video frame captured both some parts of the person's body and some parts of the objects surrounding the person. Such particular case does not limit the scope of the technology disclose herein. Other situations are possible when, for example, both the first and the second video frame areas or only one of these video frame areas capture only a part or several parts of the person's body or only a part or parts of the objects surrounding the person. Also, any of the first area or the second area can have any shape which can be different from the rectangular shape shown in FIG. 15. For example, the shape of an area (e.g., the first area or the second area) or a border of the area can follow a contour of the person's body (or, e.g., a contour of an object proximate to the person). The shape of the first area can be different from the shape of the second area. The size of the first area can be different from the size of the second area. Furthermore, any of the first area or the second area of the video frame can occupy or cover or include any percentage or fraction of the video frame. The second area can have a position within the video frame that is different from a position of the first area. The second area can at least in part overlap with the first area.

The first area having the same position within the video frame as the first area of the video frame 1500 shown in FIG. 15 was also selected in each of a number of other video frames captured by the video camera element of the PWV system. The second area having the same position within the video frame as the second area of the video frame 1500 shown in FIG. 15 was also selected in each of the said other video frames captured by the video camera element of the PWV system in which the first area was selected. The video frames in which both the first area and the second area were selected are referred to as a set of PWV video frames below.

An mSAD value, a measure of motion, was computed for each of the first areas in the set of PWV video frames to result in the first set of motion values. An mSAD value, a measure of motion, was also computed for each of the second areas in the set of PWV video frames to result in the second set of motion values.

Any computations using a motion value from the first set of motion values can be performed to result in a numeric value which will also represent a measure of motion in a first area of a video frame (e.g., the first area for which the motion value was computed or calculated). For example, for an mSAD value in the first set of motion values and any other k (k is an integer number) mSAD values belonging to the first set of motion values, a value equal to an average (e.g., a weighted average, or an arithmetic average or any other type or combination of different types of averaging) of the mSAD value and those other k mSAD values in the first set can be obtained (e.g., computed). The average values obtained for the first set of motion values are referred to as the first set of average motion values.

Similarly, any computations using a motion value from the second set of motion values can be performed to result in a numeric value which will also represent a measure of motion in a second area of a video frame (e.g., the second area for which the motion value was computed or calculated). Computations performed using the motion value from the second set of motion values can be of the same or of a different kind or type than computations performed using the motion value from the first set of motion values. For example, a value equal to an average (e.g., a weighted average, or an arithmetic average, or any other type or a combination of different types of averaging) of an mSAD value and any other n (n is an integer number) mSAD values in the second set can be computed. The average values obtained for the second set of motion values are referred to as the second set of average motion values.

Instead, or in addition to applying an averaging operation to the set(s) of motion values (or to any number of motion values in any of the sets of motion values), any other operation can be performed on or any function or operator can be applied to any number of motion values in any of the sets of motion values. For example, a frequency filter (e.g., a band-pass or a band-stop or a high-pass or a low-pass filter and/or any combination of filters) can be applied to one or more motion values in one or more of the sets of motion values.

A value from a set of average motion values is referred to as a mSADaverage value. Any mSADaverage value, similarly to any mSAD value, represents a measure of motion in an area of a video frame.

Figure 16:
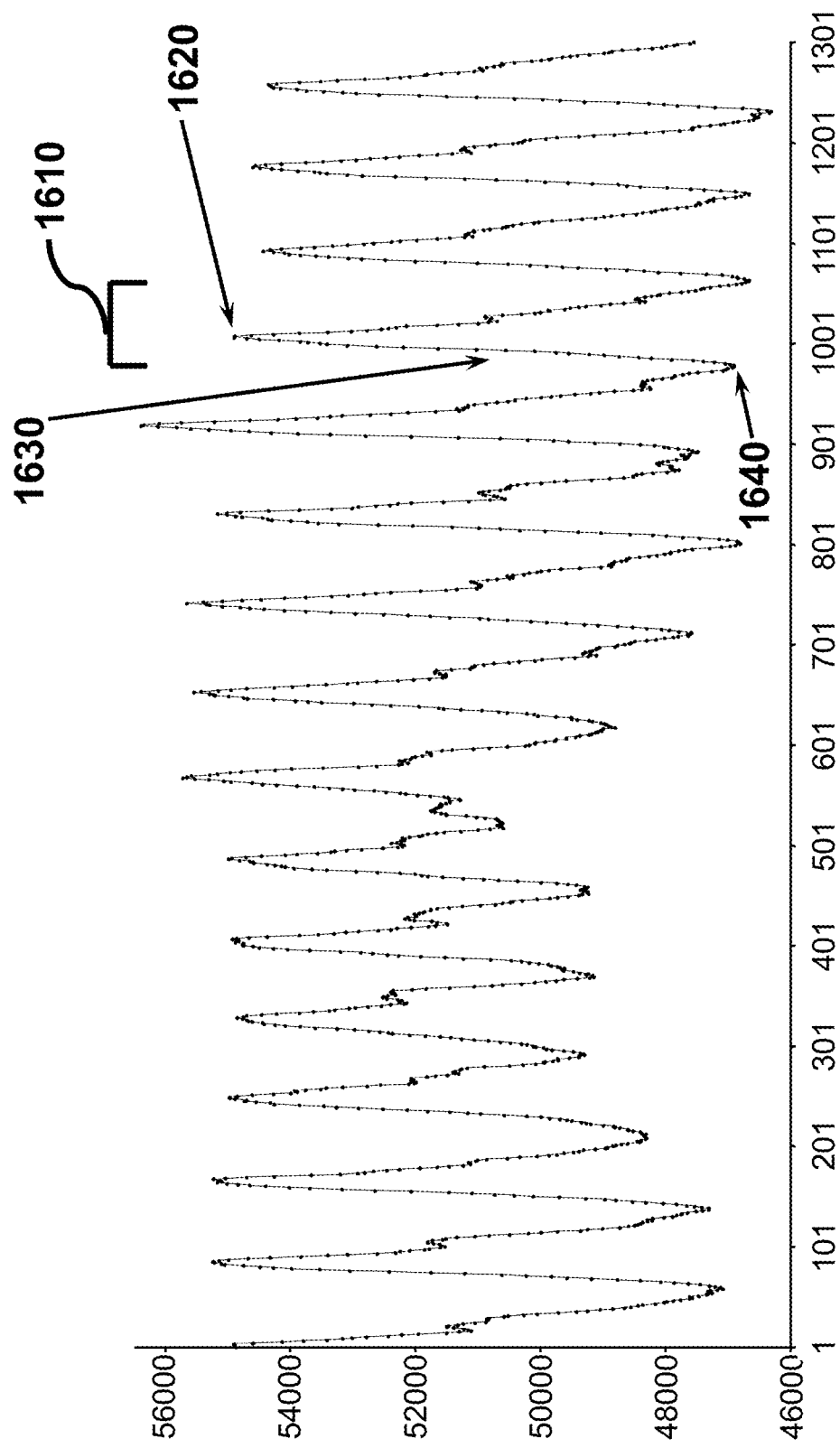
FIG. 16 shows a plot of example data obtained by a system according to the disclosed technology for the person shown in FIG. 15.
Figure 17:
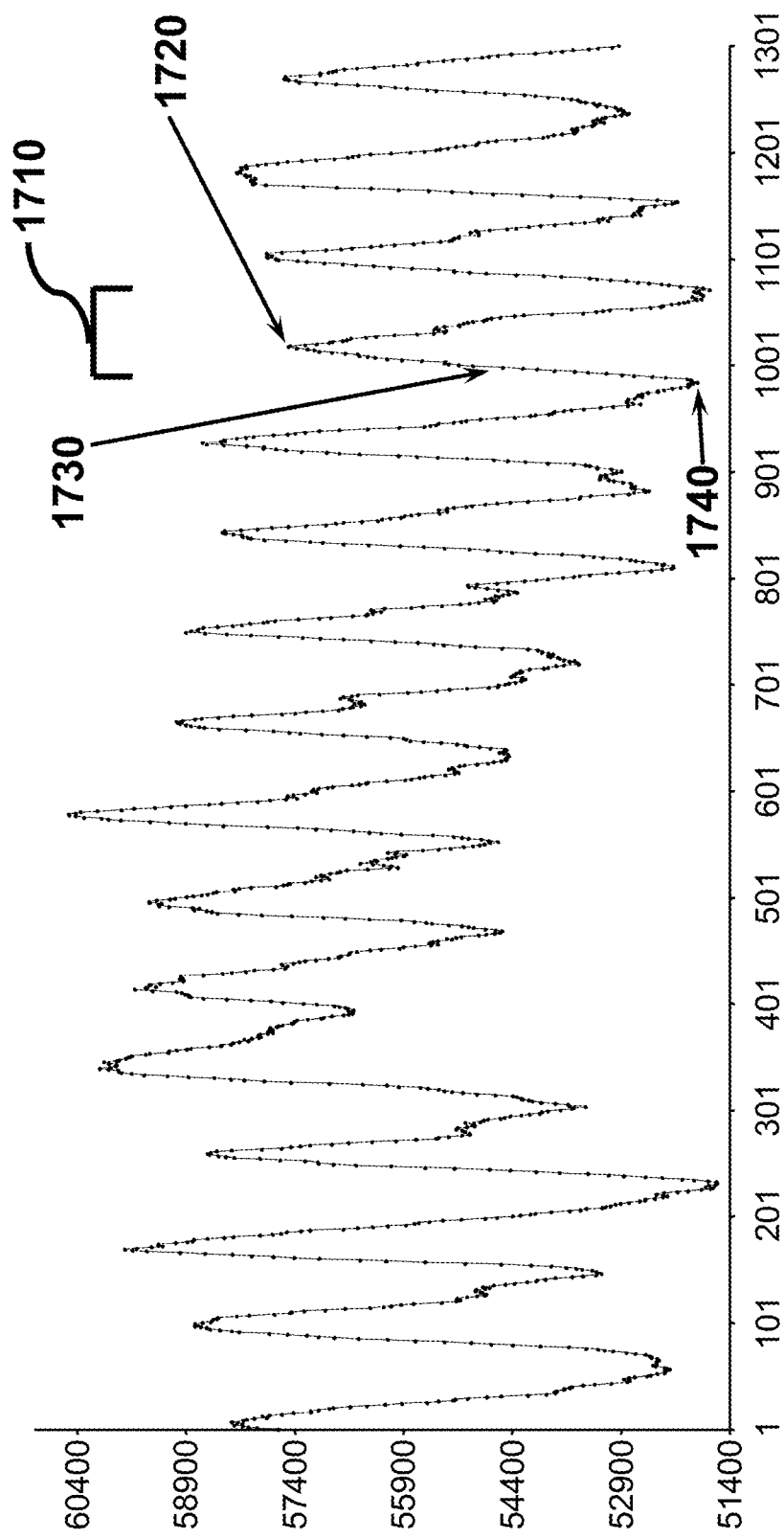
FIG. 17 shows another plot of example data obtained by a system according to the disclosed technology for the person shown in FIG. 15.

For the data plots of mSADaverage values shown in FIGS. 16 and 17 the value of k was equal to 14 and the value on n was equal to 14 as well. mSADaverage values were obtained as an arithmetic average of an mSAD value and k (or n) previous (timewise; e.g., values obtained using frames having timestamps prior to that of the frame that was used to obtain the mSAD value) mSAD values in a set of mSAD motions values. Particular choice of the values of k and/or n does not limit the scope of the technology disclosed in this patent document.

Figure 19:
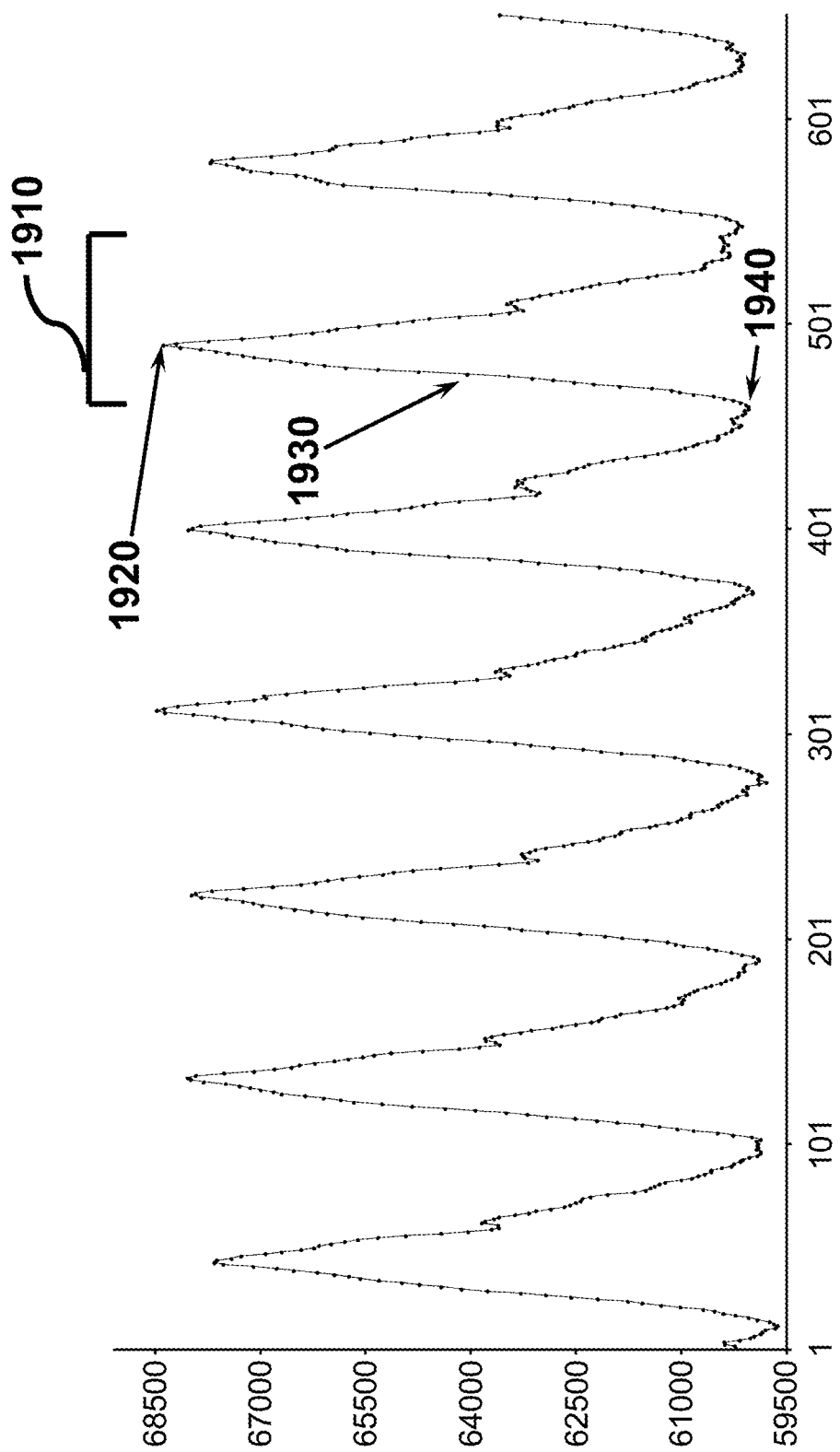
FIG. 19 shows a plot of example data obtained by a system according to the disclosed technology for the person shown in FIG. 18.
Figure 20:
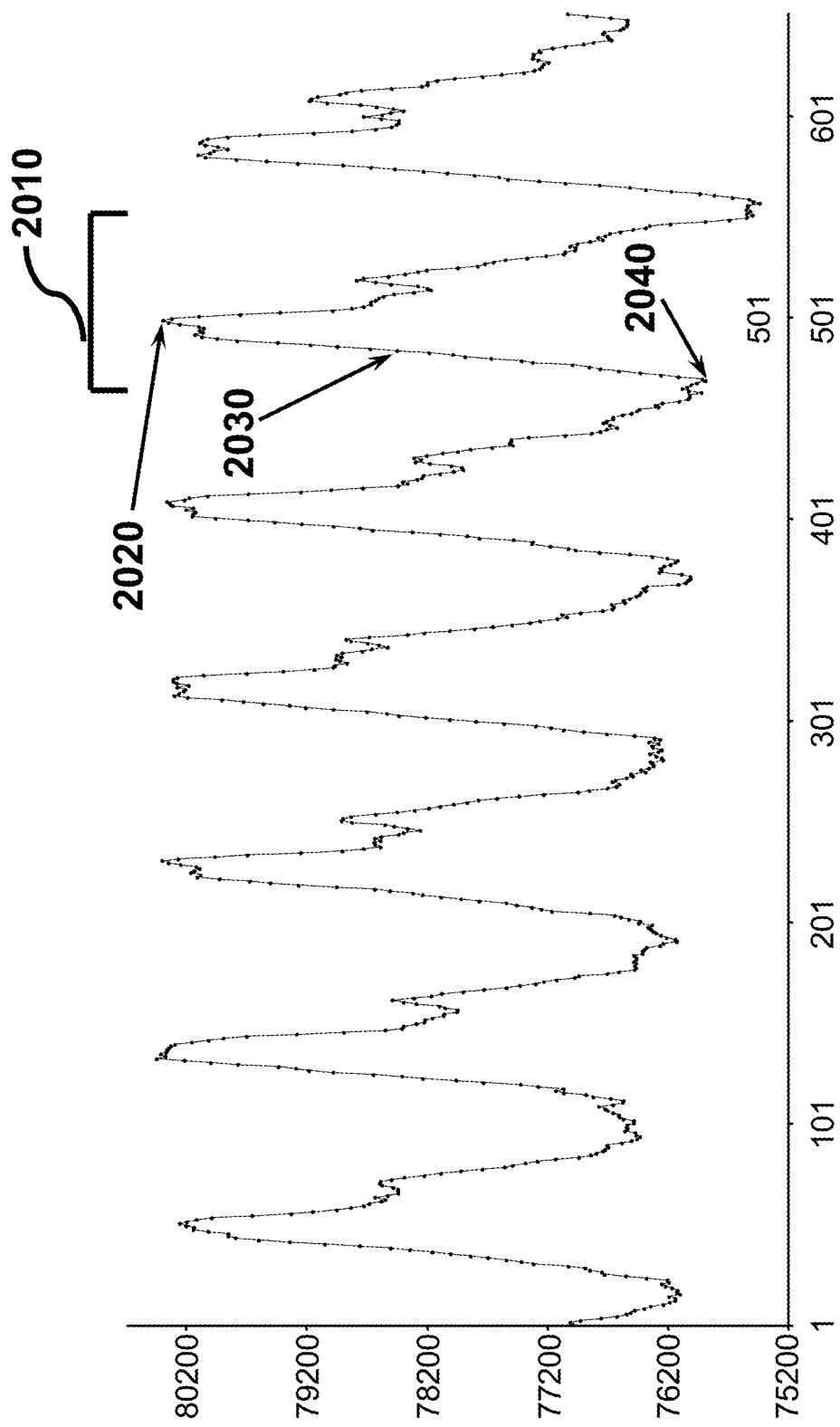
FIG. 20 shows another plot of example data obtained by a system according to the disclosed technology for the person shown in FIG. 18.

FIG. 16 shows a plot of an example first set of average motion values (obtained for the first areas of a number of video frames; all of those first areas had the same position within their respective video frames as the first area (between the lines 1510 and 1520) of the video frame 1500 shown in FIG. 15; in certain implementations, any two of the said first areas can have different positions and/or sizes and/or shapes within the respective video frames containing the said first areas). FIG. 17 shows a plot of an example second set of average motion values (obtained for the second areas of a number of video frames (the same ones for which the first set of average motion values was obtained; as discussed above, the first and the second sets of (average) motion values can have all video frames in common or some video frames in common, the sets can have the same video frames or at least one of the video frames of the first set can be different from any of the video frames in the second set); all of those second areas had the same position within their respective video frames as the second area (between the lines 1530 and 1540) of the video frame 1500 shown in FIG. 15; in certain implementations, any two of the said second areas can have different positions and/or sizes and/or shapes within the respective video frames having the said second areas selected in them). The mSADaverage points in the plots in FIG. 16 and FIG. 17 are connected by lines. Horizontal axis in FIG. 16 and horizontal axis in FIG. 17 show numbers assigned to the video frames for which the mSADaverage values were computed. These numbers can be translated into the time values (or time markers) using, for example, values of time intervals between the video frames or values of times stamps of the video frames (those values can be generated, for example, by the video camera element of the PWV system or by the computing element of the PWV system (e.g., by hardware and/or an operating system of the computing element)). Vertical axis in FIG. 16 and vertical axis in FIG. 17 show the mSADaverage values. Note that the plots in FIGS. 16, 17 as well as the plots in FIGS. 19 and 20 are shown for illustration purposes only. Instead of or along with mSADaverage values, systems and methods according to the disclosed technology can use any type of numeric values (averaged or not or filtered or processed in any way or not) that represent a measure of motion in an area of a video frame.

Data points under the bracket 1610 in FIG. 16 were selected as belonging to a heartbeat of the person shown in FIG. 15. Data points under the bracket 1710 in FIG. 17 were selected as belonging to the same heartbeat of the person.

mSADaverage data point 1620 (FIG. 16) was selected within the said heartbeat (part of the plot/data under the bracket 1610 in FIG. 16) for the first set of motion values. The point 1620 corresponds to the maximum mSADaverage value within the heartbeat, as captured in the first set of motion values. mSADaverage data point 1720 (FIG. 17) was selected within the said heartbeat (part of the data/plot under the bracket 1710 in FIG. 17) for the second set of motion values. The point 1720 corresponds to the maximum mSADaverage value within the heartbeat, as captured in the second set of motion values. Points other than the one corresponding to a maximum (local or global) value of a measure of motion within the heartbeat can be selected for any of the sets of motion values. For example, a point corresponding to a maximum rate of change (e.g., rate of increase or rate of decrease) of a measure of motion during, e.g., the systolic part (or any other part) of a heartbeat (or during the whole heartbeat) can be selected. For example, the point 1630 corresponding to a maximum rate of change of mSADaverage values during systolic part of the heartbeat under the bracket 1610 in FIG. 16 can be selected within the said heartbeat for the first set of motion values. Similarly, the point 1730 corresponding to a maximum rate of change of mSADaverage values during systolic part of the heartbeat under the bracket 1710 in FIG. 17 can be selected within the said heartbeat for the second set of motion values. As another example, a point corresponding to the "foot" of a heartbeat peak can be selected. For example, a point corresponding to a centroid of a peak or a point corresponding to a centroid of a part of a peak can be selected. For example, the point 1640 corresponding to a minimum mSADaverage value within the heartbeat under the bracket 1610 in FIG. 16 can be selected within the said heartbeat for the first set of motion values. For example, the point 1740 corresponding to a minimum mSADaverage value within the heartbeat under the bracket 1710 in FIG. 17 can be selected within the said heartbeat for the second set of motion values. Selection of the particular type of point (minimum, maximum, centroid, etc.) does not limit the scope of the technology disclosed herein. Points of different types can be selected for the first set and for the second set of motion values. The point selected for the second set of motion values can be of a different type compared to the type of the point selected for the first set of motion values. For example, a point corresponding to the maximum value of a measure of motion within a heartbeat can be selected for the first set of motion values and a point corresponding to the maximum rate of change (e.g., rate of increase or rate of decrease) of a measure of motion during, e.g., systolic part (or any other part) of the heartbeat (or during the whole heartbeat) can be selected for the second set of motion values. Moreover, the first set of motion values can include motion values of a first kind (e.g., mSAD values) while the second set of motion values can include motion values of a second kind that is different from the first kind (e.g., motion values each of which corresponds to a sum of the lengths of motion vectors in a part of a video frame; or motion values obtained using an optical flow analysis of video frames).

Video frames corresponding to the mSADaverage data points 1620 and 1720 were identified and are referred to as the first and the second video frames below, respectively.

The time interval corresponding to the duration of propagation of a blood pressure wave between an area of the person's body captured in the area of the video frame 1500 shown in FIG. 15 between the lines 1510 and 1520 (the first area of the body) and an area of the person's body captured in the area of the video frame 1500 shown in FIG. 15 between the lines 1530 and 1540 (the second area of the body) was chosen to be equal to the time interval between the first and the second video frames and was determined to be 0.12 s by calculating a difference between the time stamps of the first and the second video frames.

Instead of or in addition to or in parallel with the ways of determining time interval between a first characteristic point belonging to a heartbeat, as it (the heartbeat) is captured in a set of first video frame areas and a second characteristic point belonging to the same heartbeat, as it (the heartbeat) is captured in a set of second video frame areas which are described above, the time interval corresponding to a duration of blood pressure wave propagation between two points or two areas or two parts of a body (e.g., a human body) can be obtained using a correlation (e.g., a correlation dependence or a correlation function or the like) between a first set of motion values obtained for (e.g., computed or calculated or otherwise derived from or using) the first set of the video frame areas and a second set of motion values obtained for (e.g., computed or calculated or otherwise derived from or using) the second set of the video frame areas. For example, a (discrete or continuous) correlation function can be computed between the said sets of motion values and, in order to determine the value of the said time interval, a point of this function (e.g., the one corresponding to a maximum (e.g., a local maximum) value of the correlation function) can be determined and/or selected and used to determine the said time interval.

Note that according to some example embodiments, obtaining the time interval (or duration) of blood pressure wave propagation between two points or two areas or two parts of a body, as well as obtaining data and/or information related to any of the said physiologic parameters of the person mentioned above, does not involve using or (the word "or" can be replaced with "and/or" anywhere in this patent document) obtaining any information about any distance (the term "distance" can be replaced by any of the terms "displacement", "length", "shift", "space", "span", "gap", "interval", "separation", "interspace", "extent", "stretch", "width", "height", "depth", "range" and the like anywhere in this patent document) related to any element of a scene captured in any video frame obtained by a video camera element of a system according to the technology disclosed herein. According to some example embodiments, obtaining a duration of the time interval of blood pressure wave propagation between two points or two areas or two parts of a body, as well as obtaining data and/or information related to any of the said physiologic parameters of the person, does not include using and/or obtaining any information about any distance at all. According to some example embodiments, obtaining a duration of blood pressure wave propagation between two points or two areas or two parts of a body, as well as obtaining data (e.g., numeric values) and/or information related to any physiologic parameters of the person mentioned above, does not comprise using or obtaining any information about any position of any element of an image within the said image, wherein the image is, e.g., contained in a video frame captured by a video camera element of a system according to the technology disclosed herein. According to some example embodiments, obtaining the time interval (or duration) of blood pressure wave propagation between two points or two areas or two parts of a body, as well as obtaining information and/or data related to or corresponding to or associated with any of the physiologic parameters of the person mentioned in this patent document, does not comprise using or obtaining any information about any position of any feature of a function, computed using an image, within the said image (e.g., wherein the image is captured in a video frame obtained using a video camera element of a system according to the disclosed technology). One can say that some embodiments of systems, devices, and methods according to the disclosed technology refrain from obtaining or using any information or data about or related to or associated with any distance and/or any position of any object or of any feature or part of the object or of a feature of a function or of an element of an image for the purpose of obtaining a length of the time interval of blood pressure wave propagation between two points or two areas or two parts of a body as well as for the purpose of obtaining data and/or information related to any of the physiologic parameters of the person mentioned in this patent document. Some embodiments of the systems, devices and/or methods according to the disclosed technology do not use or obtain any information or data (e.g., numeric values) related to any color changes of skin of a subject. Some embodiments of the systems, devices and/or methods according to the disclosed technology do not use or obtain any information about any color changes of skin (of any area of the skin) of a subject (e.g., a person) which (changes) are caused by the heartbeats of the subject (including blood pulses or blood waves created by the heartbeats). The said color changes can be observed, for example, by a person or captured by a video camera when, for example, the skin is uniformly illuminated by white light. One can say that some embodiments of systems, devices, and methods according to the disclosed technology refrain from obtaining or using any information about any changes or variations of skin color of a subject. One can say that some embodiments of systems, devices, and methods according to the disclosed technology refrain from obtaining or using any information or data about any changes or variations of skin color of a subject (e.g., a person) that (changes or variations) are caused by the heartbeats of the subject. According to some example embodiments, obtaining the time interval (or duration) of blood pressure wave propagation between two points or two areas or two parts of a body, as well as obtaining data (e.g., numeric values) and/or information related to or associated with any of the physiologic parameters of the person mentioned in this patent document, does not comprise using or obtaining information about any color changes of any skin area of a subject (e.g., a person) which (changes) are, e.g., caused by the heartbeats of the subject (including blood pulses or blood waves created by the heartbeats). For the purpose of obtaining the time interval (or duration) of blood pressure wave propagation between two points or two areas or two parts of a body, as well as obtaining data (e.g., numeric values) and/or information related to or associated with any of the physiologic parameters of the person mentioned in this patent document, some example embodiments refrain from using or obtaining information about any color changes of any skin area of a subject (e.g., a person) which (changes) are, e.g., caused by the heartbeats of the subject (including blood pulses or blood waves created by the heartbeats).

To determine a PWV value using the value of the duration of blood pressure wave propagation determined above, the distance value between the first area of the body and the second area of the body was determined to be 0.7 m by measuring the distance between the said areas of the person's body using a ruler. The said distance value can be also determined, for example, using depth data which can be captured for the person using the depth-sensing functionality of an Intel RealSense camera or any other depth-sensing camera that can be used by a system (or separately from the system) according to the disclosed technology.

A pulse wave velocity value was obtained by dividing the said distance value (0.7 m) by the said time interval duration (0.12 s) and was equal to 5.8 m/s. The computations described above were performed using motion values corresponding to a single heartbeat. The computations described above can be performed (e.g., repeated) for more than one heartbeat and pulse wave velocity values obtained for multiple heartbeats can be used to obtain one or more statistics related to the pulse wave velocity characteristic of the cardiovascular system of a person (for example, an average value of those pulse wave velocity values can be obtained).

The procedure of calculating a PWV value based on a single heartbeat described above can be done/repeated for a number of other heartbeats. Statistical calculations can be performed using the PWV values obtained for a number of heartbeats with a goal, for example, to obtain a PWV value which is less affected by random heartbeat-to-heartbeat variations of the pulse wave velocity arising, for example, due to (random) noise in the ALT data. As an example of such calculations, one can calculate an average value (e.g., an arithmetic average or a weighted average or any other kind of an average value) for (or using) the PWV values obtained for several heartbeats. Particular examples of the statistical calculations do not limit the scope of the disclosed technology. Any type of calculations can be done using one or more PWV values by systems according to the disclosed technology and/or using methods according to the technology disclosed herein.

Methods according to the technology disclosed in this patent document can be used to obtain information related to the pulse wave velocity characteristic of the cardiovascular system of a person when the person, for example, wears clothes or is fully or partially covered by one or more covering items such as, e.g., a blanket. This capability of the disclosed technology is illustrated with reference to FIGS. 18-20 described below.

Figure 18:
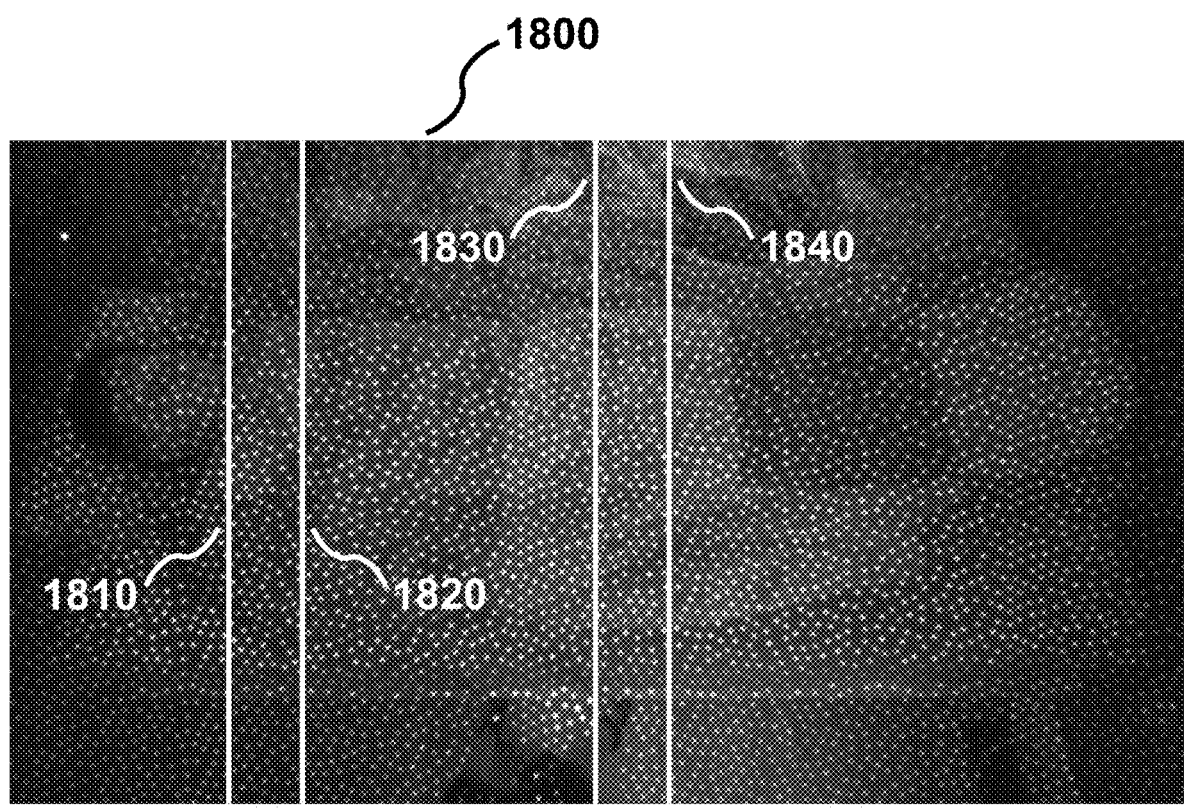
FIG. 18 illustrates an example video frame captured by a system according to the disclosed technology and showing a person lying in a bed and covered by a blanket.

FIG. 18 shows one of the IR video frames (video frame 1800) captured by the video camera element of a PWV system according to the disclosed technology. The frame shows a person lying in a bed and covered by a blanket.

The first area of the video frame 1800 in FIG. 18 is the one between the lines 1810 and 1820 in FIG. 18. The second area of the video frame 1800 in FIG. 18 is the one between the lines 1830 and 1840 in FIG. 18.

The same video frames processing and data processing steps as the ones performed to obtain the data shown in FIG. 16 and FIG. 17 were performed for the video frames captured by the PWV system for the scene shown in FIG. 18 to obtain the data shown in FIG. 19 and FIG. 20. FIG. 19 shows a plot of an example first set of average motion values obtained for the first areas of a number of video frames; all of those first areas had the same position within their respective video frames as the first area between the lines 1810 and 1820 in the video frame 1800 shown in FIG. 18. FIG. 20 shows a plot of an example second set of average motion values obtained for the second areas of a number of video frames (the same video frames for which the first set of average motion values was obtained); all of those second areas had the same position within their respective video frames as the second area between the lines 1830 and 1840 in the video frame 1800 shown in FIG. 18. The mSADaverage points in the plots in FIG. 19 and FIG. 20 are connected by lines. The fact that a system according to the disclosed technology using a method according to the disclosed technology was able to obtain data which captured pulse of a person from the second areas of video frames which correspond to the part of the person's body which is completely covered by a blanket, as shown in FIG. 18, demonstrates that devices, systems and methods according to the disclosed technology do not need to observe an area of skin (e.g., an open area of skin) of the person as well as, for example, do not have to observe or track eyes and/or head of the person which is a common feature of other technologies.

Data points under the bracket 1910 in FIG. 19 were selected (or identified) as belonging to a heartbeat of the person shown in FIG. 18. Data points under the bracket 2010 in FIG. 20 were selected (or identified) as belonging to the same heartbeat of the person.

mSADaverage data point 1920 (FIG. 19) was selected within the said heartbeat for the first set of average motion values. mSADaverage data point 2020 (FIG. 20) was selected within the said heartbeat for the second set of average motion values.

Video frames corresponding to the mSADaverage data points 1920 and 2020 were identified and are referred to below as the first and the second video frames, respectively.

The time interval corresponding to the duration of propagation of a blood pressure pulse between an area of the person's body captured in the area of the video frame 1800 shown in FIG. 18 between the lines 1810 and 1820 (the first area of the body) and an area of the person's body captured in the area of the video frame 1800 shown in FIG. 18 between the lines 1830 and 1840 (the second area of the body) was chosen to be equal to the time interval between the first video frame and the second video frame and was determined to be 0.1 s by calculating a difference between the time stamps of the first and the second video frames.

To determine a PWV value using the value of the duration of blood pressure wave propagation determined above (0.1 s), the distance value between the first area of the body and the second area of the body was determined to be 0.71 m by measuring the distance between the said areas of the person's body using a ruler. The said distance value can be also determined, e.g., using depth data which can be captured for the person using the depth-sensing functionality of a depth-sensing camera.

A pulse wave velocity value was obtained by dividing the said distance value (0.71 m) by the said time interval (0.1 s) and was equal to 7.1 m/s.

Figure 21:
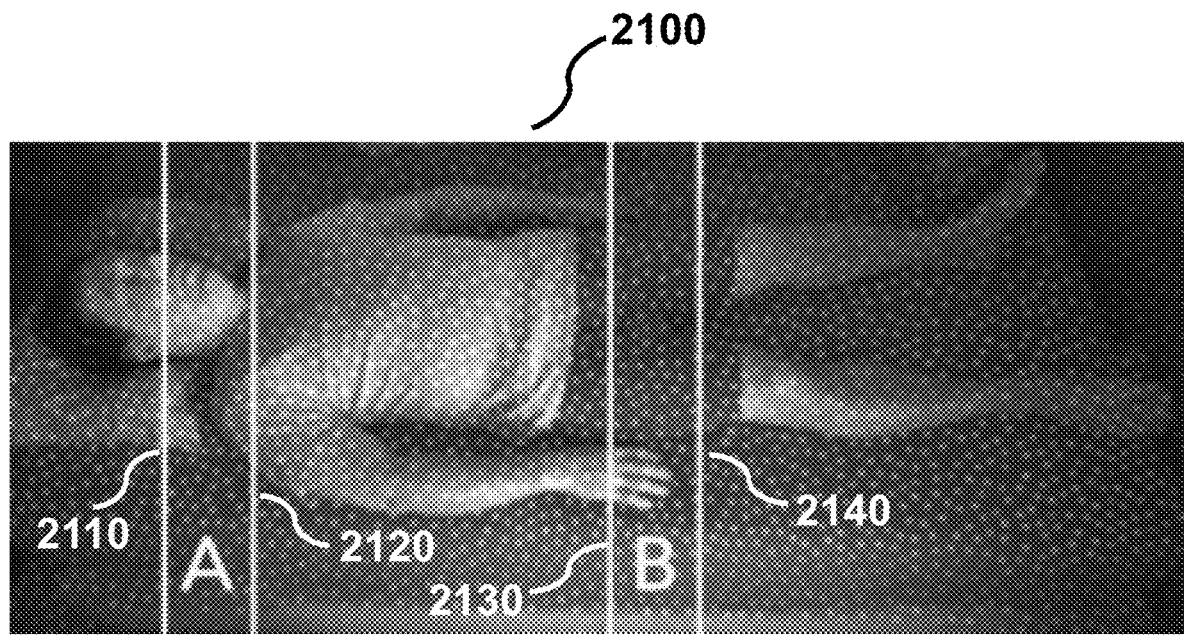
FIG. 21 illustrates an example video frame captured by a system according to the disclosed technology and showing a person lying on a bed.
Figure 22:
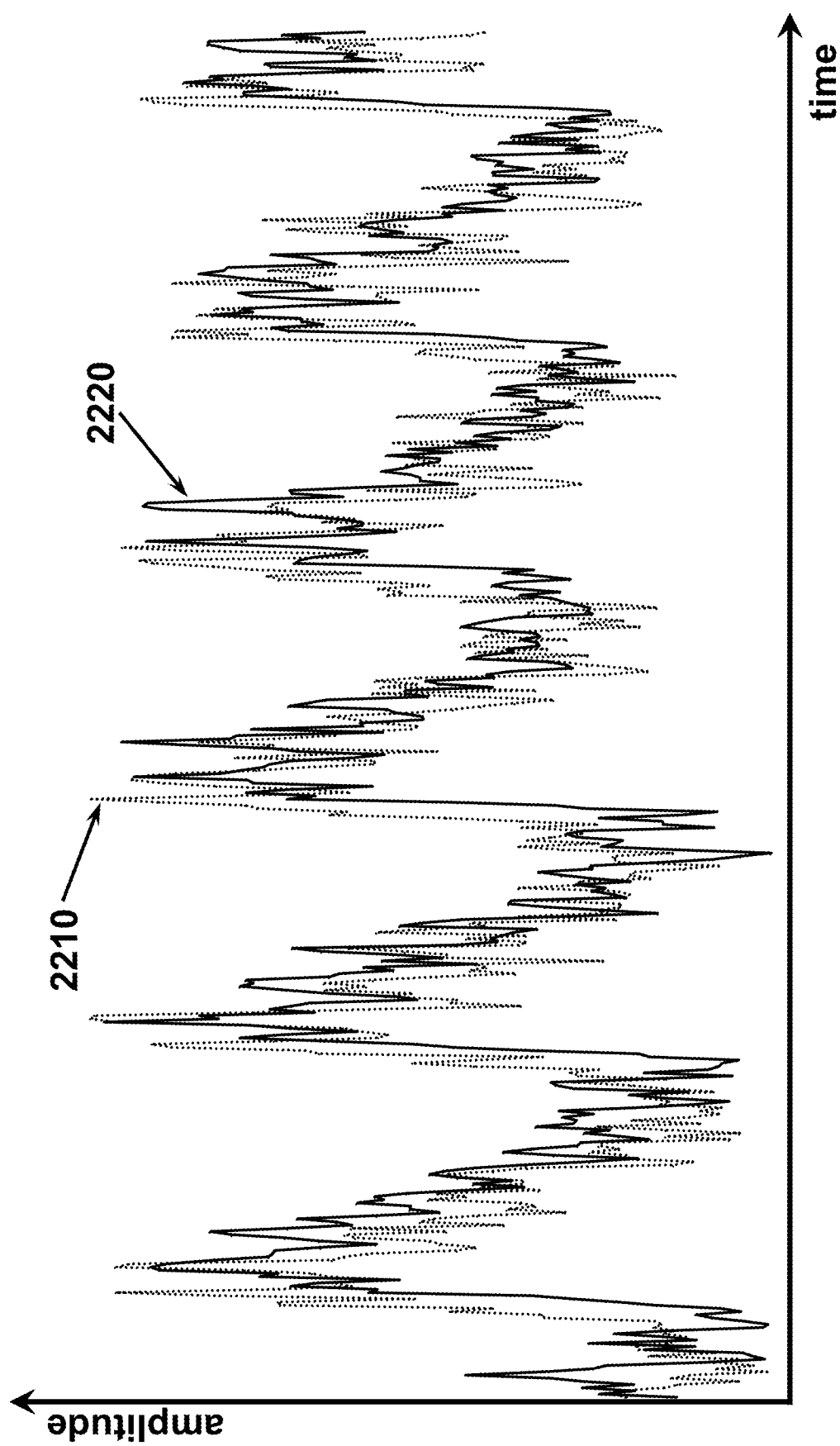
FIG. 22 shows a plot of example data obtained by a system according to the disclosed technology for the person shown in FIG. 21.

FIG. 21 shows a video frame 2100 captured by a video camera of a system according to the disclosed technology. The video frame 2100 shows a person laying on a bed. A series of mSAD data values shown by the dotted line 2210 in FIG. 22 corresponds to a series of heartbeats, as those heartbeats were captured in the areas A between the lines 2110 and 2120 (as shown for the video frame 2100 in FIG. 21) of a first number of video frames (a first set of video frames) collected by the video camera. The same heartbeats were also captured in the mSAD data corresponding to the areas B between the lines 2130 and 2140 of a second number of video frames (a second set of video frames) and are shown by the solid line 2220 in FIG. 22. The video frames that were used to obtain data shown by the line 2210 and those that were used to obtain data shown by the line 2220 in FIG. 22 can be the same video frames or the first and the second sets of the video frames can be different either completely or partially. The mSAD data set corresponding to the line 2210 has been scaled before it was plotted in the plot in FIG. 22: each mSAD number in the set was multiplied by a scaling number followed by adding a shift number to the multiplication result. That was done in order to show mSAD data sets corresponding to the lines 2210 and 2200 on the same "amplitude" scale (or withing the same "amplitude" interval) along the vertical axis of the plot shown in FIG. 22. The horizontal "time" axis in FIG. 22 shows progression of time. As data shown in FIG. 22 demonstrate, there is a clear time shift between the series of heartbeats as captured in the areas A of video frames which is shown by the line 2210 in FIG. 22, and the series of heartbeats as captured in the areas B of video frames which is shown by the line 2220 in FIG. 22. There is also a time shift for each individual heartbeat between its captures in different series: the time profile of a heartbeat, as it was captured in the areas B of the video frames, is shifted towards longer times compared to the time profile of the heartbeat, as it was captured in the areas A of the video frames. The magnitudes of these time shifts reflect durations of blood wave propagation between the parts of the body of the person shown in FIG. 21 that are shown in the area A of the video frame 2100 in FIG. 21 and areas of the body of the person that are shown in the area B of the video frame 2100 and can be determined using any of the methods according to the disclosed technology.

Figure 23:
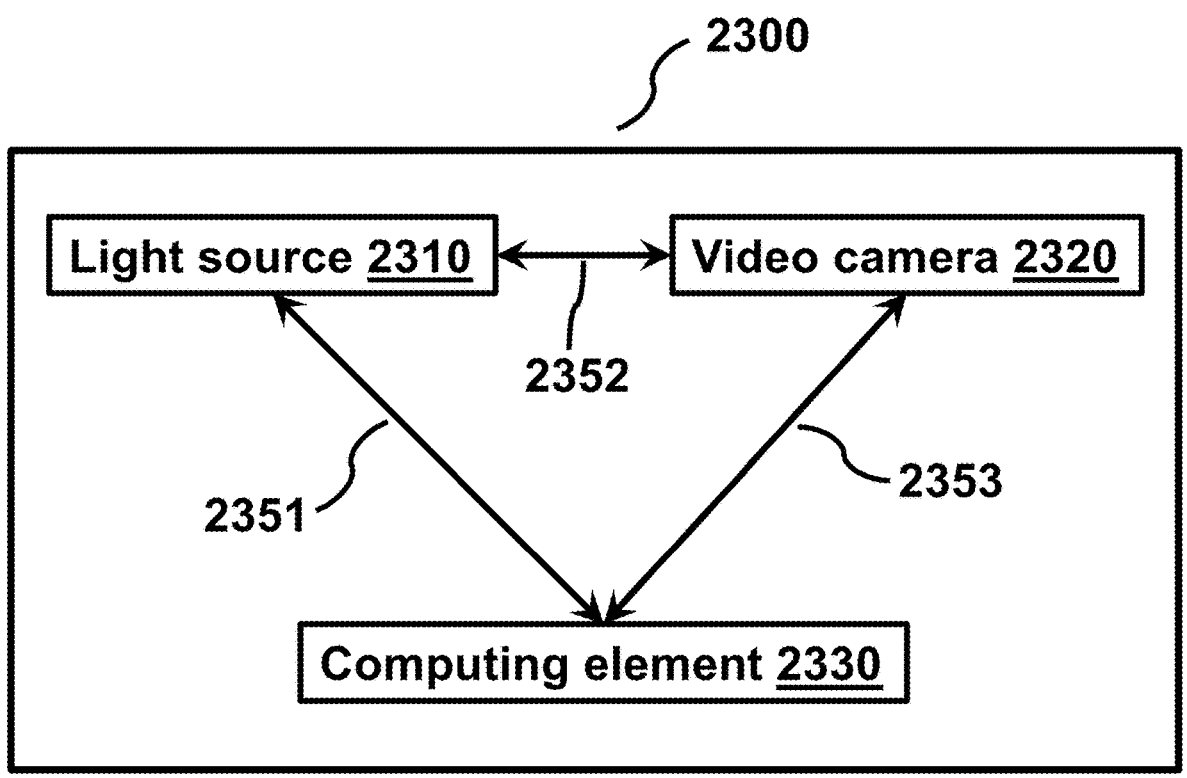
FIG. 23 shows a schematic diagram of an example device according to the disclosed technology.

FIG. 23 shows a schematic diagram of an example device 2300 according to the disclosed technology. The device 2300 includes a light source 2310, a video camera 2320 as well as a computing element 2330. Double-ended arrows 2351, 2352 and 2353 in FIG. 23 show possible communication and/or control connections and/or links between the elements 2310, 2320, and 2330 of the device 2300 with the direction of the arrows indicating direction of the communication messages and/or control commands and/or data flow. In some example implementations, the light source 2310 of the device 2300 can be configured to illuminate one or more areas in a manner described in this patent document. According to some example implementations, the video camera 2320 of the device 2300 can be configured to capture one or more video frames. In some example implementations, the computing element 2330 of the device 2300 can be configured to perform any of the computations described in this patent document, for example, any of the computations that are mentioned in relation to any method or system or device according to the disclosed technology.

Figure 24:
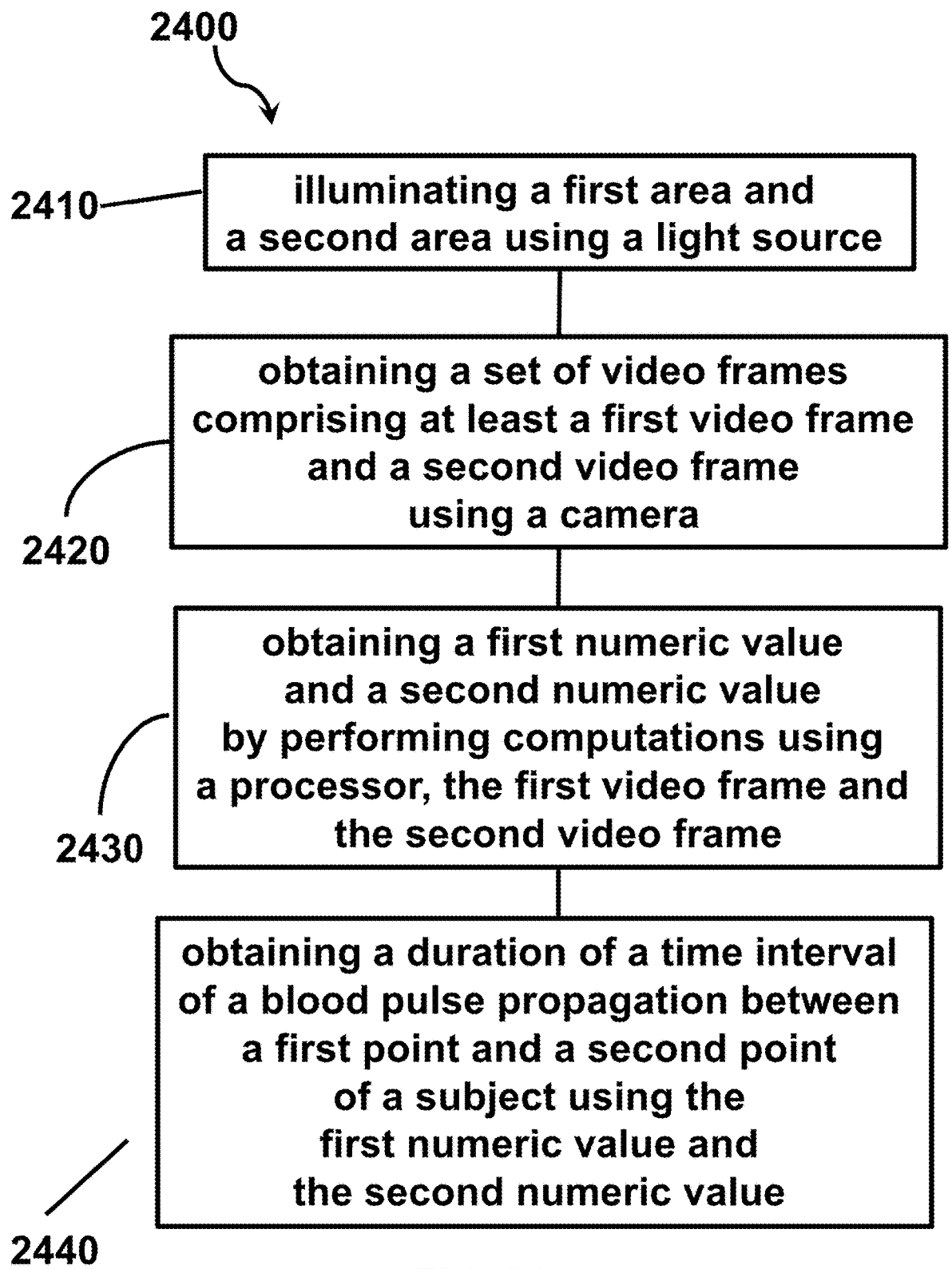
FIG. 24 shows a flowchart of an example method according to the disclosed technology.

FIG. 24 shows a flowchart of an example embodiment of a method 2400 according to the disclosed technology. The method 2400 includes a step 2410 of illuminating a first area and a second area using a light source. The method 2400 also includes a step 2420 of obtaining a set of video frames comprising at least a first video frame and a second video frame using a camera. The method 2400 further includes a step 2430 of obtaining a first numeric value and a second numeric value by performing computations using a processor, the first video frame and the second video frame. The method 2400 also includes a step 2440 of obtaining a duration of a time interval of a blood pulse propagation between a first point and a second point of a subject using the first numeric value and the second numeric value.

The pulse wave velocity values obtained for a person using devices, systems and methods according to the technology disclosed in this patent document can be used to obtain information and/or data (e.g., numeric values) related to the blood pressure of the person using any method which establishes a relationship between a pulse wave velocity value and a blood pressure (systolic and/or diastolic) value. For example, a blood pressure numeric value can be obtained by using a functional relationship between the blood pressure (systolic and/or diastolic) and pulse wave velocity. For example, the methods described in the work "Relation between blood pressure and pulse wave velocity for human arteries" by Ma et al. (DOI: https://doi.org/10.1073/pnas.1814392115), which is incorporated herein by reference, can be used for that purpose. For example, the functional relationship can be a quadratic relationship between a pulse wave velocity value pWV and a blood pressure (e.g., diastolic or systolic) value P: $P=a(pWV)^2+b$, wherein a and b are numeric coefficients. For example, the value of the numeric coefficient a can be about 0.046 $kPa \cdot s^2 \cdot m^{-2}$. For example, the value of the numeric coefficient b can be about 5.1 kPa. If one is, for example, interested in following relative changes of pulse wave velocity and/or blood pressure of a person, then, a duration of pulse wave propagation between two areas or point or parts of the body of the person can be determined following any of the methods according to the technology disclosed herein but, instead of measuring a distance between the said areas or points or parts of the person's body followed by dividing the said distance (which, for example, could be difficult for the person to measure in a reliable way or with a sufficiently high accuracy) by the determined duration, one can divide the height of the person (which the person likely knows and which can be measured with a relatively high accuracy including, for example, by the person herself) by the determined duration of the pulse wave propagation to produce a height-related ratio (referred to as a height-related velocity value). Furthermore, a blood pressure value can be obtained using such determined height-related velocity value. Changes (e.g., relative ones) in the thus determined height-related velocity values will reflect changes in the person's blood pressure and/or ("real") pulse wave velocity values. A calibration function can be determined and/or used to translate the height-related velocity values into the systolic and/or diastolic blood pressure values for the person, and/or to the pulse wave velocity values for the person, for example.

An example aspect of the disclosed technology relates to a method of obtaining information related to at least one of: a respiration rate of a person, a heart rate of the person, a respiration rate variability of the person, a heart rate variability of the person, a temporal characteristic of at least a part of a heartbeat of the person, or a temporal characteristic of at least a part of a respiration cycle of the person, comprising the steps of: 1) illuminating a set of areas of the person's body (or illuminating a set of areas of an object, or illuminating a set of areas of a body; e.g., the object is an object that is in contact (e.g., a direct contact or a contact via other objects) with the person's body; e.g., the body is a body of a female/mother having a fetus inside it if/when the method is used to determine information about the fetus or if/when the person is the fetus (as described above, the term "person" herein generally refers to an adult person, a child, an infant/baby, and/or a fetus inside the body of a female/mother); therefore, the phrase "person's body" can be replaced by any of "object" or "body" in this patent document) using a light source; 2) collecting a video frames set for at least one of the illuminated areas using a video camera; 3) performing computations for at least two video frames of the video frames set to result in a set of numeric values for the video frames set using a computer; and 4) performing computations for at least a part of the set of numeric values using the computer to obtain numeric values related to the at least one of: the respiration rate of the person, the heart rate of the person, the respiration rate variability of the person, the heart rate variability of the person, the temporal characteristic of at least a part of a heartbeat of the person, or the temporal characteristic of at least a part of a respiration cycle of the person, or display the said at least a part of the set of numeric values using a graphical representation of the said at least a part of the set of numeric values, wherein the step 3) comprises the steps of: i) for each video frame in the at least two video frames of the video frames set performing computations comprising the steps of: a) for each pixel of at least a part of the video frame associating a numeric value with the pixel using video frame data of the video frame; b) for each pixel of at least a part of another video frame in the said video frames set associating a numeric value with the pixel using video frame data of the another video frame; c) for each pixel of the said at least a part of the video frame calculating a difference between the numeric value associated with the pixel and the numeric value associated with a pixel of the said at least a part of another video frame; d) for each pixel of the said at least a part of the video frame calculating a numeric value equal to at least one of: an absolute value of the difference or a squared value of the difference; and e) calculating a sum of the numeric values calculated for the pixels of the said at least a part of the video frame in the step d) to result in a numeric value for the video frame. In some example embodiments, the method (as well as some embodiments of any other method, system, medium or device according to the disclosed technology) does not use or obtain any information about any distance related to any element of a scene captured in any video frame of the said video frames set. In some example embodiments, the method (as well as some embodiments of any other method, system, medium or device according to the disclosed technology) does not use or obtain any information about position of any element of an image of a scene captured in any video frame of the said video frames set within the said image.

In some example embodiments, computations for at least two video frames of the video frames set that result in the set of numeric values for the video frames set and computations for the said at least a part of the set of numeric values that result in numeric values related to the at least one of: the respiration rate of the person, the heart rate of the person, the respiration rate variability of the person, the heart rate variability of the person, the temporal characteristic of at least a part of a heartbeat of the person, or the temporal characteristic of at least a part of a respiration cycle of the person, or display of the said at least a part of the set of numeric values using a graphical representation of the said at least a part of the set of numeric values do not use or obtain any information about any distance related to (or associated with or assigned to, etc.) any element of a scene captured in any video frame of the said video frames set.

In some example embodiments, computations for at least two video frames of the video frames set that result in the set of numeric values for the video frames set and computations for the said at least a part of the set of numeric values that result in numeric values related to the at least one of: the respiration rate of the person, the heart rate of the person, the respiration rate variability of the person, the heart rate variability of the person, the temporal characteristic of at least a part of a heartbeat of the person, or the temporal characteristic of at least a part of a respiration cycle of the person, or display of the said at least a part of the set of numeric values using a graphical representation of the said at least a part of the set of numeric values do not use or obtain any information about position of any element of an image of a scene captured in any video frame of the said video frames set within the said image.

In some example embodiments, the said video frames set has at least three video frames. According to some example embodiments, each video frame in the said video frames set has at least two pixels.

In some example embodiments, step 1) results in the set of areas of the person's body receiving more photons during an exposure time period for any frame of the video frames set than the set of areas of the person's body would have received during the exposure time period for any frame of the video frames set without performing step 1) and under the otherwise identical conditions.

In some example embodiments, a ratio of average illumination for two areas of the person's body captured in a frame of the said video frames set is at least $1+1/(2^n-2)$, wherein n is a number of bits in a binary representation of a numeric value associated with a pixel of the said frame and contained in video frame data of the said frame, and the said ratio is determined using the numeric values associated with pixels of the said frame and contained in the video frame data of the said frame, wherein the pixels correspond to the said two areas of the person's body. In certain example embodiments, n equals to one of: 8, 16, 32, 64, 128, 256, 512, 1024, 2048, 4096 or 8192 (n does not have to be an even number or a power of two). According to some example embodiments, the ratio of the average illumination for two areas of the person's body captured in a frame of the said video frames set is at least 1.001. In some example embodiments, the ratio of the average illumination for two areas of the person's body captured in a frame of the said video frames set is at least 1.01. In some example embodiments, the ratio of the average illumination for two areas of the person's body captured in a frame of the said video frames set is at least 1.1. In some example embodiments, the ratio of the average illumination for two areas of the person's body captured in a frame of the said video frames set is at least 10. In some example embodiments, the ratio of the average illumination for two areas of the person's body captured in a frame of the said video frames set is at least 100. In some example embodiments, the ratio of the average illumination for two areas of the person's body captured in a frame of the said video frames set is at least 1000. According to some example embodiments, the numeric values associated with the said each pixel of at least a part of the video frame and the numeric values associated with the said each pixel of at least a part of another video frame in the step i) of step 3) are obtained using a same set of rules. In certain example embodiments, a pixel row number for the said pixel of the video frame and a pixel row number for the said pixel of the said another video frame in the step c) of step i) of step 3) are equal, as well as a pixel column number for the said pixel of the video frame and a pixel column number for the said pixel of the said another video frame in the step c) of step i) of step 3) are equal. In some example embodiments, the said pixel of the said another video frame in the step c) of step i) of step 3) is selected by a video encoder. According to certain example embodiments, the step 3) comprises replacing at least one numeric value in the said set of numeric values for the said video frames set by another numeric value from the said set of numeric values for the said video frames set. In some embodiments, the said graphical representation of the said at least a part of the set of numeric values is a two-dimensional plot. In some example embodiments, the method further comprises saving at least one video frame of the video frames set to a local or remote storage medium. In some example embodiments, the method further comprises saving at least one numeric value of the said set of numeric values for the video frames set to a local or remote storage medium. According to certain example embodiments, the method further comprises saving at least one numeric value of the said numeric values related to the at least one of: the respiration rate of the person, the heart rate of the person, the respiration rate variability of the person, the heart rate variability of the person, the temporal characteristic of at least a part of a heartbeat of the person, or the temporal characteristic of at least a part of a respiration cycle of the person to a local or remote storage medium. According to certain example embodiments, the local or remote storage medium is a non-transitory storage medium. In some example embodiments, the numeric values associated with the said each pixel of at least a part of the video frame in the step i) of step 3) are obtained using a first set of rules (the first set of rules includes one or more rules) and the numeric values associated with the said each pixel of at least a part of another video frame in the step i) of step 3) are obtained using a second set of rules (the second set of rules includes one or more rules), wherein the second set of rules is different from (or different then) the first set of rules (a difference may be between any rule in the first set of rules and any rule in the second set of rules; the first set of rules can have different rules compared to the second set of rules).

Another example aspect of the disclosed technology relates to a system for obtaining information related to at least one of: a respiration rate of a person, a heart rate of the person, a respiration rate variability of the person, a heart rate variability of the person, a temporal characteristic of at least a part of a heartbeat of the person, or a temporal characteristic of at least a part of a respiration cycle of the person, comprising: 1) a light source element configured to illuminate a set of areas of the person's body (the set of areas can include one or more areas of the body); 2) a video camera element configured to collect a video frames set (or a set of video frames; the video frames set can include one or more video frames) for at least one of the illuminated areas; and 3) a computing element and a non-transitory storage medium readable by the computing element and storing instructions that, when executed by the computing element, cause the computing element to perform computations comprising the steps of: i) performing computations for at least two video frames of the video frames set to result in a set of numeric values for the video frames set; and ii) performing computations for at least a part of the set of numeric values to result in at least one of: obtaining one or more numeric values related to the at least one of: the respiration rate of the person, the heart rate of the person, the respiration rate variability of the person, the heart rate variability of the person, the temporal characteristic of at least a part of a heartbeat of the person, or the temporal characteristic of at least a part of a respiration cycle of the person, or displaying at least a part of the set of numeric values using a graphical representation of the said at least a part of the set of numeric values, wherein the step i) comprises: performing computations for each video frame in the at least two video frames of the video frames set, comprising the steps of: a) for each pixel of at least a part of the video frame associating a numeric value with the pixel using video frame data of the video frame; b) for each pixel of at least a part of another video frame in the said video frames set associating a numeric value with the pixel using video frame data of the another video frame; c) for each pixel of the said at least a part of the video frame calculating a difference between the numeric value associated with the pixel and the numeric value associated with a pixel of the said at least a part of another video frame; d) for each pixel of the said at least a part of the video frame calculating a numeric value equal to at least one of: an absolute value of the difference or a squared value of the difference; and e) calculating a sum of the numeric values calculated for the pixels of the said at least a part of the video frame in the step d) to result in a numeric value for the video frame. In some example embodiments, any of the said computations performed by the computing element (as well as any (or some) computations used in some embodiments of other methods, systems, mediums or devices according to the disclosed technology) do not use or obtain any information about any distance related to any element of a scene captured in any video frame of the said video frames set. In some example embodiments, any of the said computations performed by the computing element (as well as any (or some) computations used in some embodiments of other methods, systems, mediums or devices according to the disclosed technology) do not use or obtain any information about position of any element of an image of a scene captured in any video frame of the said video frames set within the said image.

According to some example embodiments, the type of the said computing element is one of: a computer, a single-board computer, a tablet, or a smartphone. In certain example embodiments, the said computing element has a graphics processing unit. In certain example embodiments, at least a part of any of the said computations is performed using the said graphics processing unit.

In some example embodiments, the said light source element is a light source having (or characterized by) a distribution of wavelengths with a maximum above 700 nm. In some example embodiments, the said light source element is a light source capable of emitting light (or configured to emit light) on one or more wavelengths above 700 nm. According to some example embodiments, the said light source element is a light source having (or characterized by) a distribution of wavelengths with a maximum between approximately 350 nm and approximately 750 nm. In some example embodiments, the said light source element is a light source capable of emitting light on one or more wavelengths between approximately 350 nm and approximately 750 nm. In certain example embodiments, the said light source element is a laser. According to some example embodiments, the said light source element includes a laser. In certain example embodiments, the said light source element is a light-emitting diode (LED). According to certain example embodiments, the said light source element includes a light-emitting diode (LED).

In some example embodiments, the said light source element is configured to illuminate the said areas by producing one or more light spots on the said areas, wherein the light spots have illumination maxima separated by at least 1 nm distance for at least two of the said light spots. In some example embodiments, the light spots have illumination maxima separated by at least 1000 nm distance for at least two of the said light spots. According to some example embodiments, the light spots have illumination maxima separated by at least 1 mm distance for at least two of the said light spots. In some example embodiments, the light spots have illumination maxima separated by at least 10 mm distance for at least two of the said light spots. In some example embodiments, the said light source element is configured to illuminate the said areas by producing one or more light spots on the said areas, wherein a first light spot in the one or more light spots has a first illumination maximum within the first light spot, a second light spot in the one or more light spots has a second illumination maximum within the second light spot and a distance between a location of the first illumination maximum and a location of the second illumination maximum is at least 1 nm. In some example embodiments, the said distance is at least 1000 nm. According to some example embodiments, the said distance is at least 1 mm. In some example embodiments, the said distance is at least 10 mm.

In some example embodiments, the said light source element is configured to illuminate the said areas by creating light spots on the said areas, wherein the light spots are separated from each other by areas of the person's body having lower illumination compared to that of the light spots. According to some example embodiments, the said light source element is configured to illuminate the said areas by creating one or more light spots on each of the said areas, wherein at least two of the light spots are separated from each other by an area of the person's body having lower illumination compared to that of any of the two light spots.

In some example embodiments, the said light source element is configured to illuminate the said areas by creating light spots on the said areas, and wherein the said light source element has a capability to change at least one of: a distance between at least two of the said light spots, a size of at least one of the said light spots, a shape of at least one of the said light spots, or illumination intensity of at least one of the said light spots.

According to some example embodiments, the said illuminating a set of areas comprises creating light spots on the said areas, wherein the light spots are separated from each other by areas of the person's body having lower illumination compared to that of the light spots.

An example aspect of the disclosed technology relates to a method of obtaining information related to at least one of: a respiration rate of a person, a heart rate of the person, a respiration rate variability of the person, a heart rate variability of the person, a temporal characteristic of at least a part of a heartbeat of the person, or a temporal characteristic of at least a part of a respiration cycle of the person, comprising: illuminating at least one area of the person's body using a light source; collecting a set of video frames comprising at least a first video frame and a second video frame using a video camera; processing the set of video frames using a computer, the processing comprising: for each pixel of a part of the first video frame, associating a numeric value with the pixel; for each pixel of a part of the second video frame, associating a numeric value with the pixel; for each pixel of the part of the second video frame, calculating a difference between the numeric value associated with the pixel and the numeric value associated with a pixel of the part of the first video frame; for each pixel of the part of the second video frame, calculating a numeric value equal to at least one of: an absolute value of the difference calculated for the pixel or a squared value of the difference calculated for the pixel; and obtaining a first numeric value using a sum of the said numeric values calculated for the pixels of the part of the second video frame.

In some example embodiments, the method does not use or obtain any information about any distance related to any element of a scene captured in any video frame of the said set of video frames. According to some example embodiments, the said processing the set of video frames using a computer does not use or obtain any information about any distance related to any element of a scene captured in any video frame of the said set of video frames. In some example embodiments, the method (or any other method according to the disclosed technology) further includes refraining from obtaining or using any information about any distance related to any element of a scene captured in any video frame of the said set of video frames.

According to some example embodiments, the method does not use or obtain any information about position of any element of an image of a scene captured in any video frame of the said set of video frames within the said image. In some example embodiments, the said processing the set of video frames using a computer does not use or obtain any information about position of any element of an image of a scene captured in any video frame of the said set of video frames within the said image. According to some example embodiments, the method (or any other method according to the disclosed technology) further includes refraining from using or obtaining any information about position of any element of an image of a scene captured in any video frame of the said set of video frames within the said image.

In some example embodiments, the said for each pixel of a part of the first video frame, associating a numeric value with the pixel is performed using video frame data of the first video frame. According to some example embodiments, the said associating a numeric value with the pixel of the part of the first video frame is performed using video frame data of the first video frame.

In some example embodiments, the said for each pixel of a part of the second video frame, associating a numeric value with the pixel is performed using video frame data of the second video frame. According to some example embodiments, the said associating a numeric value with the pixel of the part of the second video frame is performed using video frame data of the second video frame.

In some example embodiments, the said pixel of the part of the first video frame and the said pixel of the part of the second video frame used in the said calculating a difference are such that a pixel row number of the said pixel of the part of the first video frame and a pixel row number of the said pixel of the part of the second video frame are equal, and a pixel column number of the said pixel of the part of the first video frame and a pixel column number of the said pixel of the part of the second video frame are equal.

In some example embodiments, the said pixel of the part of the first video frame and the said pixel of the part of the second video frame used in the said calculating a difference are such that a pixel row number of the said pixel of the part of the first video frame and a pixel row number of the said pixel of the part of the second video frame are different, or a pixel column number of the said pixel of the part of the first video frame and a pixel column number of the said pixel of the part of the second video frame are different.

In some example embodiments, the part of the first video frame is selected by a video encoder and the part of the second video frame is selected by the video encoder.

In some example embodiments, the method further comprises encoding at least one of the first video frame or the second video frame using a video encoder. According to some example embodiments, the video encoder is a H.264 encoder. In some example embodiments, the video encoder is a H.265 encoder or a H.266 encoder or a H.267 encoder or a H.268 encoder or a H.269 encoder or a H.270 encoder.

In some example embodiments, the method also comprises obtaining a second numeric value using the first numeric value using the computer. According to some example embodiments, the second numeric value is related to the at least one of: the respiration rate of the person, the heart rate of the person, the respiration rate variability of the person, the heart rate variability of the person, the temporal characteristic of at least a part of a heartbeat of the person, or the temporal characteristic of at least a part of a respiration cycle of the person.

Another example aspect of the disclosed technology relates to a system for obtaining information related to at least one of: a respiration rate of a person, a heart rate of the person, a respiration rate variability of the person, a heart rate variability of the person, a temporal characteristic of at least a part of a heartbeat of the person, or a temporal characteristic of at least a part of a respiration cycle of the person, comprising: a light source element configured to illuminate at least one area of the person's body; a video camera element configured to collect a set of video frames comprising at least a first video frame and a second video frame; and a computing element and a non-transitory storage medium readable by the computing element and storing instructions which, when executed by the computing element, cause the computing element to perform computations comprising: for each pixel of a part of the first video frame, associating a numeric value with the pixel; for each pixel of a part of the second video frame, associating a numeric value with the pixel; for each pixel of the part of the second video frame, calculating a difference between the numeric value associated with the pixel and the numeric value associated with a pixel of the part of the first video frame; for each pixel of the part of the second video frame, calculating a numeric value equal to at least one of: an absolute value of the difference calculated for the pixel or a squared value of the difference calculated for the pixel; and obtaining a first numeric value using a sum of the said numeric values calculated for the pixels of the part of the second video frame.

In some example embodiments, any of the said computations performed by the computing element do not use or obtain any information about any distance related to (or associated with or otherwise put into a correspondence with) any element of a scene captured in any video frame of the said set of video frames. According to some example embodiments, information or data related to any of the physiologic parameters mentioned in this patent document can be obtained without obtaining or using any information or data (e.g., numeric values) about (or related to) any distance related to (or associated with or otherwise put into a correspondence with) any element of a scene captured in any video frame of the said set of video frames.

In some example embodiments, any of the said computations performed by the computing element do not use or obtain any information about position (or coordinates) of any element of an image of a scene captured in any video frame of the said set of video frames within the said image. According to some example embodiments, information or data (e.g., numeric values) related to any of the physiologic parameters mentioned in this patent document can be obtained without obtaining or using any position and/or any distance information related to any element of an image detected or captured by a sensor of a video camera (e.g., a video camera element of a system according to the disclosed technology) or/and without obtaining or using any position and/or any distance information related to any feature of a function computed using one or more images detected by a sensor of a video camera (e.g., a video camera element of a system according to the disclosed technology).

According to some example embodiments, the computing element is one of: a computer, a single-board computer, a tablet, or a smartphone. In some example embodiments, the said computing element comprises a graphics processing unit. According to some example embodiments, at least a part of any of the said computations is performed using the said graphics processing unit.

In some example embodiments, the said light source element is an infrared light source. An infrared light source is, for example, a light source that is configured to emit or produce or generate (or is capable of emitting or producing or generating) light having a wavelength that is between approximately 700 nm and approximately 1 mm. The infrared light source can be configured to generate light having many spectral components on one or more wavelengths between approximately 700 nm and approximately 1 mm. In some example embodiments, the said light source element is configured to emit light (or is capable of emitting light) on one or more wavelengths between approximately 1 nm and approximately 10 meters (10 m). According to some example embodiments, the said light source element is configured to produce light in a visible part of the electromagnetic spectrum, e.g., light having one or more wavelengths between about 380 nm and about 750 nm. In some example embodiments, the said light source element is configured to produce light on one or more wavelengths between about 450 nm and approximately 485 nm corresponding to blue light. In some example embodiments, the said light source element is configured to produce light on one or more wavelengths between approximately 500 nm and approximately 565 nm corresponding to green light. In some example embodiments, the said light source element is configured to produce light on one or more wavelengths between approximately 625 nm and about 700 nm corresponding to red light.

According to some example embodiments, the said video camera element is an infrared camera. An infrared camera is, for example, a camera or a light detector or a light sensor or a device that is configured to register or detect (or is capable of registering or detecting) light having a wavelength that is between approximately 700 nm and approximately 1 mm. An infrared camera is, for example, a camera that is capable of obtaining (or is configured to obtain) images using light of one or more wavelengths between approximately 700 nm and approximately 1 mm. According to some example embodiments, the said video camera element is a camera or a light detector or a light sensor or a device capable of obtaining (or configured to obtain) images using light having a wavelength that is between (approximately) 1 nm and (approximately) 10 m. In some example embodiments, the said video camera element is a camera or a device configured to register light or detect light having a wavelength that is between (approximately) 1 nm and (approximately) 10 m.

In some example embodiments, the said light source element is configured to illuminate the at least one area by creating a light spot on the at least one area, wherein the light spot has an illumination due to the light source element which is higher than an illumination produced by the light source element on the at least one area around the light spot.

According to some example embodiments, the said light source element is configured to illuminate the at least one area by creating light spots on the at least one area, wherein the light spots are separated from each other by areas of the person's body having lower illumination due to the light source element compared to that of the light spots.

In some example embodiments, the said light source element is configured to illuminate the at least one area by producing light spots on the at least one area, wherein at least a first light spot and a second light spot in the light spots are such that an illumination maximum of the first light spot is separated from an illumination maximum of the second light spot by at least 1 nm distance. According to some example embodiments, the said light source element is configured to illuminate the at least one area by producing light spots on the at least one area, wherein at least a first light spot and a second light spot in the light spots are such that a center (e.g., a geometric center or a center determined using illumination distribution within the light spot) of the first light spot is separated from a center of the second light spot by at least 1 nm distance. In some example embodiments, instead of 1 nm, the said distance is at least 1 mm or at least 10 mm or at least 10 cm.

In some example embodiments, the said light source element is configured to illuminate the at least one area by creating light spots on the at least one area, and wherein the said light source element is configured to change (or is capable of changing) at least one of: a distance at least between two of the said light spots, a size of at least one of the said light spots, a shape of at least one of the said light spots, or illumination intensity of at least one of the said light spots.

In some example embodiments, the said light source element is configured to illuminate a set of areas (one or more areas) of a person's body, wherein the said illumination leads to creating or increasing illumination contrast between the said areas and other areas of the person's body, as observed in video frames captured by the video camera element.

Yet another example aspect of the disclosed technology relates to a non-transient computer-readable storage medium storing instructions that, when executed by a computer (or by one or more processors), cause the computer to (or cause the one or more processors to): cause a light source to illuminate at least one area of a subject (or an object or a body of a person); cause a video camera to collect one or more video frames; and perform computations according to a method according to the technology disclosed in this patent document.

An example aspect of the disclosed technology relates to a non-transient computer-readable storage medium storing instructions that, when executed by a computer (or by one or more processors), cause the computer to (or cause the one or more processors to): cause a light source to illuminate at least one area of an object; cause a video camera to collect a set of video frames comprising at least a first video frame and a second video frame; and perform computations, comprising: for each pixel of a part of the first video frame, associating a numeric value with the pixel; for each pixel of a part of the second video frame, associating a numeric value with the pixel; for each pixel of the part of the second video frame, calculating a difference between the numeric value associated with the pixel and the numeric value associated with a pixel of the part of the first video frame; for each pixel of the part of the second video frame, calculating a numeric value equal to at least one of: an absolute value of the difference calculated for the pixel or a squared value of the difference calculated for the pixel; and obtaining a first numeric value using a sum of the said numeric values calculated for the pixels of the part of the second video frame.

In some embodiments, the one or more processors include a graphics processing unit (GPU).

In some embodiments, the associating includes (or is) assigning a (numeric) value to the pixel and/or selecting a (numeric) value from (or for) the pixel. In some embodiments, the value is included in the pixel (a pixel of a video frame as a set of numeric values corresponding to a pixel of a video sensor). According to some embodiments, the associating includes (or is) obtaining the pixel from a camera or from a memory of a computer. In some embodiments, the associating includes (or is) using one or more (numeric) values of the pixel in a calculation or a computation. In some embodiments of methods, devices, systems and media/medium according to the disclosed technology, any of the steps including associating a numeric value with a/the pixel of a video frame are optional and can be omitted from those embodiments. For example, an example aspect of the disclosed technology relates to a method of obtaining information related to at least one of: a respiration rate of a person, a heart rate of the person, a respiration rate variability of the person, a heart rate variability of the person, a temporal characteristic of at least a part of a heartbeat of the person, or a temporal characteristic of at least a part of a respiration cycle of the person, comprising: illuminating at least one area of the person's body using a light source; collecting a set of video frames comprising at least a first video frame and a second video frame using a video camera; processing the set of video frames using a computer, the processing comprising: for each pixel of a part of the second video frame, calculating a difference between a numeric value associated with the pixel and a numeric value associated with a pixel of a part of the first video frame; for each pixel of the part of the second video frame, calculating a numeric value equal to at least one of: an absolute value of the difference calculated for the pixel or a squared value of the difference calculated for the pixel; and obtaining a first numeric value using a sum of the said numeric values calculated for the pixels of the part of the second video frame.

In certain implementations of the disclosed technology, an absolute value of a numeric value (e.g., of a numeric value b) or a squared value of the numeric value (e.g., of the numeric value b) can be replaced by the numeric value raised to any power (or exponent) m, e.g., $b^m$. For example, the power (or the exponent) m can be equal to any integer number or to any floating point or fractional number. In certain implementations of the disclosed technology, the said absolute value of the numeric value or squared value of the numeric value as well as the numeric value raised to a power m (e.g., $b^m$, wherein m is any number (floating point or integer)) can be replaced by a numeric value which is a result of any calculations or computations involving any of the absolute value of the numeric value or the squared value of the numeric value or the numeric value raised to the power m (e.g., $b^m$, wherein m is any number (floating point or integer)).

In some example embodiments, any portion of the video frame(s) obtain by a system or a device according to the disclosed technology as well as any part of the data obtained or produced or computed by the system or the device can be stored on a local or remote storage medium. For example, a local storage medium is the one which is included in the device or the system or the one which is directly connected to the system or the device via a wired link (e.g., USB or Ethernet) or the one which is located in the same computer network which includes the device or the system. For example, a remote storage medium is the one which is typically referred to as located "in the cloud" or, generally, the one that is located in a part of a computer network other than a local computer network (or sub-network) that includes the device or the system. For example, the said video frames and/or data can be transferred to the said medium using a wired or a wireless connection or communication link (e.g., Wi-Fi, Ethernet, Bluetooth, LTE, Internet, etc.) as well as using any communication protocol (e.g., TCP/IP).

In some example embodiments, devices, systems, or storage medium(s) according to the disclosed technology can be embedded into other devices or systems. For example, a system according to the disclosed technology can be incorporated into a floor lamp or any other source of illumination. For example, a system according to the disclosed technology can be embedded into a bed (e.g., into bed's headboard). According to some example implementations, the technology disclosed in this patent document provides an article of manufacture which includes a device or a system or a computer-readable storage medium according to the technology disclosed herein.

An example aspect of the disclosed technology relates to a method of determining a duration (or length) of a time interval of a blood pulse (or a blood wave) propagation between a first point (or a first area or a first part) and a second point (or a second area or a second part) of a subject, comprising: illuminating a first area proximate to the first point and a second area proximate to the second point using a light source; obtaining a set of video frames (one or more video frames) comprising at least a first video frame and a second video frame using a camera; and performing computations, using a processor, the computations comprising: for each pixel of a first part of the second video frame, calculating a difference between a numeric value associated with the pixel and a numeric value associated with a pixel of a first part of the first video frame; for each pixel of the first part of the second video frame, calculating a numeric value using the difference calculated for the pixel; obtaining a first numeric value using a sum of the said numeric values calculated for the pixels of the first part of the second video frame; for each pixel of a second part of the second video frame, calculating a difference between a numeric value associated with the pixel and a numeric value associated with a pixel of a second part of the first video frame; for each pixel of the second part of the second video frame, calculating a numeric value using the difference calculated for the pixel; obtaining a second numeric value using a sum of the said numeric values calculated for the pixels of the second part of the second video frame; and obtaining the duration of the time interval of the blood pulse (or the blood wave) propagation between the first point and the second point of the subject using the first numeric value and the second numeric value.

In some example embodiments, the said illuminating the first area (or the said illuminating the second area; the phrase "first area" in the text below can be replaced by the phrase "second area"; the statements below related to the first area are applicable to the second area as well) comprises illuminating one or more sub-areas (a sub-area of an area is a part or a section or a region of the area) within the first area such that any of the illuminated sub-areas is at least partially surrounded by (or encompassed by) a part (or an area) of the first area having a lower illumination compared to illumination of the sub-area. In some example embodiments, the said illuminating the first area comprises illuminating one or more sub-areas within (or inside) the first area such that any of the illuminated sub-areas is proximate to a part (or an area) of the first area having a lower average illumination compared to an average illumination of the sub-area. In certain example embodiments, an average illumination of an area or a part of the first area or a sub-area of the first area is illumination averaged over the area or the part of the first area or the sub-area of the first area. In certain example embodiments, an average illumination of an area or a part of the first area or a sub-area of the first area is illumination (e.g., an average illumination over the area or over the part of the first area or over the sub-area of the first area) averaged over time (e.g., over a certain time interval) for the area or the part of the first area or the sub-area of the first area. In certain example embodiments, illumination is proportional to (e.g., equal to) irradiance or illuminance or any other measure of a flux or a level of electromagnetic radiation produced by the light source on (and/or through) an area (e.g., a sub-area or any other part of the first area).

In some example embodiments, the said illuminating the first area comprises illuminating one or more sub-areas in the first area such that any of the illuminated sub-areas is at least partially surrounded by a part of the first area receiving (e.g., on average, timewise) a lower amount (or level) of light from the light source per a unit of time compared to the amount of light that the sub-area is receiving (e.g., on average, timewise) from the light source per the unit of time (e.g., 1 second). In certain example embodiments, the amount of light is proportional to (e.g., is equal to) irradiance or illuminance or any other measure of a flux or a level of electromagnetic radiation produced by the light source on (and/or through) an area (e.g., a sub-area or any other part of the first area). In some example embodiments, the said illuminating the first area comprises illuminating one or more sub-areas within the first area such that any of the illuminated sub-areas is at least partially surrounded by a part (or an area) of the first area receiving a lower irradiance from the light source compared to an irradiance that the sub-area is receiving from the light source. In some example embodiments, the said illuminating the first area comprises illuminating one or more sub-areas within the first area such that any of the illuminated sub-areas is at least partially surrounded by (or encompassed by) or is proximate to a part of the first area receiving a lower average (e.g., an average over the surface of the part of the first area) irradiance from the light source compared to an average (e.g., an average over the surface of the sub-area) irradiance that the sub-area is receiving from the light source.

In some example embodiments, the illuminating the first area comprises imparting photons from the light source to a sub-area of the first area and avoiding or refraining from imparting photons from the light source to an area (or a part or a region) of the first area that is proximate to or at least partially surrounding or at least partially encompassing or at least partially contacting the sub-area.

In some example embodiments, the said illuminating the first area comprises creating (or producing) one or more light spots on the first area. According to some example embodiments, a light spot among the said light spots is a light spot as described in this patent document and/or as demonstrated in the Figures accompanying this patent document.

In certain example embodiments, the light source is configured to provide illumination of a sub-area in the first area (or provide an amount (or level) of light to the sub-area) which is (at least) K times higher compared to illumination (e.g., due to the light source) of a part or a section or an area of the first area that is different from the sub-area. In some example embodiments, K is larger than 1. According to some example embodiments, K is larger than $1+10^{-100}$. In some example embodiments, K is larger than $1+10^{-6}$. In some example embodiments, K is larger than $1+10^{-3}$. In some example embodiments, K is larger than $1+10^{-2}$. In some example embodiments, K is larger than $1+10^{-1}$. In some example embodiments, K is larger than 2. In some example embodiments, K is larger than 5. In some example embodiments, K is larger than 10. In some example embodiments, K is larger than 100. In some example embodiments, K is larger than 1000. In some example embodiments, K is larger than 10000. In some example embodiments, K is larger than 100000. In some example embodiments, K is larger than 1000000. In some example embodiments, K is larger than 1000000000. In some example embodiments, K is larger than 1000000000000. In some example embodiments, K is smaller than 1000000000000. In some example embodiments, K is smaller than 1000000000. In some example embodiments, K is smaller than 1000000. In some example embodiments, K is smaller than 100000. In some example embodiments, K is smaller than 10000. In some example embodiments, K is smaller than 1000. In some example embodiments, K is smaller than 100. In some example embodiments, K is smaller than 50. In some example embodiments, K is smaller than 10. In some example embodiments, K is smaller than 5. In some example embodiments, K is smaller than 2.

In some example embodiments, the first area and/or the second area are located on the subject (e.g., on the body (e.g., skin) of the subject and/or on the clothes the subject is wearing and/or on a blanket that the subject is covered with such that a part of the body of the subject is located under the first area and/or the second area located on the subject's clothes or the blanket, as viewed by the camera (from the point of view of the camera)). In some embodiments, at least one of the first area or the second area is not on the subject (e.g., such that there is no any part of the subject's body under such area when the area is observed from the point of view of the camera). Any of the first area and/or the second area can be located on any part of the subject or on any part of the objects other than the subject. In certain example embodiments, the first area is located proximate to a carotid artery in the neck of the subject. In certain example embodiments, the first area includes an area on the neck of the subject. In certain example embodiments, the first area is located proximate to a heart of the subject. In certain example embodiments, the first area includes an area on the chest (or thorax) of the subject. In certain example embodiments, the second area is located proximate to a femoral artery in the groin of the subject. In certain example embodiments, the second area includes an area on a hip or a thigh of the subject. The first area and/or the second area can have any size and any shape (e.g., any size relative to the subject). The said illumination of the first area and/or the second area can cover any part or parts of any of these areas and can cover any fraction or any percentage of the first area and/or the second area.

In some example embodiments, the said numeric value calculated for a pixel of the first part of the second video frame using the difference calculated for the pixel is equal to at least one of: an absolute value of the difference calculated for the pixel or a squared value of the difference calculated for the pixel. According to some example embodiments, the said numeric value calculated for a pixel of the second part of the second video frame using the difference calculated for the pixel is equal to at least one of: an absolute value of the difference calculated for the pixel or a squared value of the difference calculated for the pixel.

In some example embodiments, the first numeric value is equal to a sum of the said numeric values calculated for the pixels of the first part of the second video frame. According to some example embodiments, the second numeric value is equal to a sum of the said numeric values calculated for the pixels of the second part of the second video frame.

In some example embodiments, any of the said first part of the second video frame, first part of the first video frame, second part of the second video frame, or second part of the first video frame (as well as any part or area or section of any video frame mentioned in this patent document) can have any position or location or coordinates or indices (or any other type of identification labels or information associated with the part or area or section) within a video frame, and can have any shape and/or any size (e.g., a size relative to that of the video frame).

The technology disclosed in this patent document removes a frequent/common requirement of other technologies to have an area of skin of a subject (e.g., a person) exposed to a system or a device in order to measure a heart rate of the person, for example, due to the fact that the camera of a device or a system according to the disclosed technology does not need to observe any area or areas of skin of the subject as well as it does not have to observe the eyes of the subject, for example. Methods, systems and devices according to the disclosed technology can function in situations when the person is completely covered by one or more items such as a blanket or items of clothing (e.g., they can function when the person is wearing any clothes, including loose-fitting ones, which can cover the whole body of the person, for example, or when the person is completely covered by one or more blankets such that all areas and parts of the person's body are completely covered by the one or more blankets), as long as the movements of the person's body which are related to the person's respiration and/or heartbeats are at least partially imparted onto the said one or more items (e.g., to a surface area of any of such items that is observed by a video camera element of a system according to the disclosed technology), as discussed and as demonstrated on a number of examples in this patent document. Furthermore, information related to any of the physiologic parameters of a person (e.g., the ones mentioned above) can be determined even when a video camera element of a system or a device according to the disclosed technology does not observe the person or does not have the person in its view (e.g., when the camera does not observe even a region or area of space occupied by the person and/or any items (e.g., clothes) which are on the person or covering the person); the video camera element can, instead, observe objects around the person, a light source element of the system can impart additional light texture according to the disclosed technology to one or more of those objects and a computing element of the systems can perform computations according to a method according to the disclosed technology to obtain numeric values or other types of information about or related to any of the physiologic parameters of the person. Propagation of mechanical movements of the person's body to objects around the person makes such type of monitoring feasible. The features of devices, methods, and systems according to the disclosed technology described in this patent document allow detecting heartbeats of a fetus inside the body of a mother using the technology disclosed herein. For example, a light source element of a system according to the disclosed technology can illuminate one or more areas of the body of the mother, a video camera element of the system can collect one or more video frames capturing those areas and a computing element of the system can perform computations using the collected video frames according to a method according to the disclosed technology to obtain numeric values (ALT data) that contain information about fetal heartbeats as well as heartbeats and respiration of the mother. As mentioned above, in some implementations, the video camera element of the system does not even have to observe the body of the mother directly; instead, it can be focused on one or more objects around the mother and collect a number of video frames capturing those objects; in such a case, the light source of the system will illuminate one or more areas on those objects; the same algorithms according to the disclosed technology that were used when the camera observed the body of the mother directly can be used in this case to obtain numeric values (ALT data) that contain information about fetal heartbeats as well as heartbeats and/or respiration of the mother. Similarly, when monitoring heartbeats and respiration of a baby, the camera element of a system according to the disclosed technology does not have to have the baby in its field of view; instead, the camera can be focused, for example on a crib in which the baby is sleeping.

An example aspect of the disclosed technology relates to a system for determining a duration of a time interval of a blood pressure wave propagation between a first point (or a first area or a first part) and a second point (or a second area or a second part) of a subject, comprising: a light source configured to illuminate a first area proximate to the first point and a second area proximate to the second point; a camera configured to obtain a set of video frames comprising at least a first video frame and a second video frame; and a processor and a non-transient processor-readable storage medium storing one or more instructions which, when executed by the processor, cause the processor to: for each pixel of a first part of the second video frame, calculate a difference between a numeric value associated with the pixel and a numeric value associated with a pixel of a first part of the first video frame; for each pixel of the first part of the second video frame, calculate a numeric value using the difference calculated for the pixel; obtain a first numeric value using a sum of the said numeric values calculated for the pixels of the first part of the second video frame; for each pixel of a second part of the second video frame, calculate a difference between a numeric value associated with the pixel and a numeric value associated with a pixel of a second part of the first video frame; for each pixel of the second part of the second video frame, calculate a numeric value using the difference calculated for the pixel; obtain a second numeric value using a sum of the said numeric values calculated for the pixels of the second part of the second video frame; and obtain the duration of the time interval of the blood pressure wave propagation between the first point and the second point of the subject using the first numeric value and the second numeric value.

According to some example embodiments, the processor is one of or includes one of: an electric circuit, a microprocessor, a computer, a single-board computer, a tablet, a smartphone, a GPU, an ASIC chip, or an FPGA chip.

In some example embodiments, the said light source is an infrared light source. In some example embodiments, the said light source is configured to emit light (or is capable of emitting light) on one or more wavelengths between approximately 1 nm and approximately 10 meters (10 m).

According to some example embodiments, the said camera is an infrared camera. An infrared camera is, for example, a camera or a light detector or a light sensor or a device that is configured to register or detect (or is capable of registering or detecting) light having a wavelength that is between approximately 700 nm and approximately 1 mm or that is between approximately 700 nm and approximately 750 nm or that is between approximately 700 nm and approximately 800 nm or that is between approximately 700 nm and approximately 850 nm or that is between approximately 700 nm and approximately 900 nm or that is between approximately 700 nm and approximately 950 nm or that is between approximately 700 nm and approximately 1000 nm or that is below approximately 10 m or that is below approximately 1 mm or that is below approximately 1000 nm or that is below approximately 900 nm or that is below approximately 800 nm. An infrared camera is, for example, a camera that is capable of obtaining (or is configured to obtain) images using light of one or more wavelengths between approximately 700 nm and approximately 1 mm. According to some example embodiments, the said camera is a camera or a light detector or a light sensor or a device capable of obtaining (or configured to obtain) images using light having a wavelength that is between approximately 1 nm and approximately 10 m. In some example embodiments, the said camera is a camera or a sensor or a detector or a device that is configured to register light or detect light having a wavelength that is between approximately 1 nm and approximately 10 m.

In some example embodiments, the said light source is configured to illuminate the first area by creating a first light spot on the first area, wherein the first light spot has an illumination due to the light source which is higher than an illumination produced by the light source on a part or an area of the first area which is around (or proximate to or at least partially encompassing or at least partially bordering or touching) the first light spot. In some example embodiments, the said light source is configured to illuminate the second area by creating a second light spot on the second area, wherein the second light spot has an illumination due to the light source which is higher than an illumination produced by the light source on a part or an area of the second area which is around (or proximate to or at least partially encompassing or at least partially bordering or touching) the second light spot.

According to some example embodiments, the said light source is configured to illuminate the first area by creating light spots on the first area, wherein the light spots are separated from each other by regions or parts of the first area having lower illumination due to the light source compared to that of the light spots. According to some example embodiments, the said light source is configured to illuminate the second area by creating light spots on the second area, wherein the light spots are separated from each other by regions or parts of the second area having lower illumination due to the light source compared to that of the light spots.

In some example embodiments, the said light source is configured to illuminate the first area and the second area by producing light spots on the first area and the second area, wherein at least a first light spot and a second light spot among the light spots on the first area are such that an illumination maximum of the first light spot is separated from an illumination maximum of the second light spot by at least 1 nm distance and wherein at least a third light spot and a fourth light spot among the light spots on the second area are such that an illumination maximum of the third light spot is separated from an illumination maximum of the fourth light spot by at least 1 nm distance. According to some example embodiments, the said light source is configured to illuminate the first area and the second area by producing light spots on the first area and the second area, wherein at least a first light spot and a second light spot among the light spots on the first area are such that a center (e.g., a geometric center or a center determined using illumination distribution due to the light source within the light spot) of the first light spot is separated from a center of the second light spot by at least 1 nm distance, and wherein at least a third light spot and a fourth light spot among the light spots on the second area are such that a center (e.g., a geometric center or a center determined using illumination distribution due to the light source within the light spot) of the third light spot is separated from a center of the fourth light spot by at least 1 nm distance. In some example embodiments, instead of 1 nm, the said distance is at least 1 micrometer or at least 1 mm or at least 10 mm or at least 20 mm or at least 50 mm or at least 100 mm. In some example embodiments, the said distance is less than 1 m or is less than 50 cm or is less than 30 cm or is less than 15 cm or is less than 10 cm or is less than 5 cm or is less than 1 cm.

In some example embodiments, the said light source is configured to illuminate the first area and the second area by creating light spots on the first area and the second area, and wherein the said light source is configured to change (or is capable of changing) at least one of: a distance at least between two of the said light spots on the first area or a distance at least between two of the said light spots on the second area, a size of at least one of the said light spots, a shape of at least one of the said light spots, or an illumination intensity of at least one of the said light spots.

In some example embodiments, the said light source is configured to illuminate one or more areas within the first area and one or more areas within the second area, wherein the said illumination leads to creating or increasing illumination contrast between the said one or more areas within the first area and other parts of the first area, as well as leads to creating or increasing illumination contrast between the said one or more areas within the second area and other parts of the second area, as observed in video frames captured by the camera.

Yet another example aspect of the disclosed technology relates to a non-transient computer-readable storage medium storing instructions that, when executed by a computer (or by one or more processors), cause the computer to (or cause the one or more processors to): cause a light source to illuminate a first area proximate to a first point and a second area proximate to a second point; cause a video camera to collect one or more video frames; and perform computations which are described in this patent document (e.g., in relation to a method according to the technology disclosed in this patent document).

An example aspect of the disclosed technology relates to a non-transient computer-readable storage medium storing instructions that, when executed by a computer (or by one or more processors), cause the computer to (or cause the one or more processors to): cause a light source to illuminate a first area proximate to a first point of a subject and a second area proximate to a second point of the subject; cause a camera to obtain a set of video frames comprising at least a first video frame and a second video frame; and perform computations comprising: for each pixel of a first part of the second video frame, calculate a difference between a numeric value associated with the pixel and a numeric value associated with a pixel of a first part of the first video frame; for each pixel of the first part of the second video frame, calculate a numeric value using the difference calculated for the pixel; obtain a first numeric value using a sum of the said numeric values calculated for the pixels of the first part of the second video frame; for each pixel of a second part of the second video frame, calculate a difference between a numeric value associated with the pixel and a numeric value associated with a pixel of a second part of the first video frame; for each pixel of the second part of the second video frame, calculate a numeric value using the difference calculated for the pixel; obtain a second numeric value using a sum of the said numeric values calculated for the pixels of the second part of the second video frame; and obtain a duration of a time interval of a blood pressure wave propagation between the first point and the second point of the subject using the first numeric value and the second numeric value.

According to some example embodiments, determining the time interval (or duration) of blood pressure wave propagation between two points or two areas or two parts of a body according to the disclosed technology does not involve using or obtaining any information about any distance or any displacement or any depth related to any element of a scene captured in any video frame obtained by a video camera element of a system according to the technology disclosed herein. According to some example embodiments, determining the time interval (or duration) of blood pressure wave propagation between two points or two areas or two parts of a body according to the disclosed technology does not include using or obtaining any information about any distance or any displacement or any depth at all. According to some example embodiments, determining the time interval (or duration) of blood pressure wave propagation between two points or two areas or two parts of a body according to the disclosed technology does not comprise using or obtaining any information about any position of any element of an image of a scene within the said image in any video frame captured by a video camera element of a system according to the technology disclosed herein. According to some example embodiments, determining the time interval (or duration) of blood pressure wave propagation between two points or two areas or two parts of a body according to the disclosed technology does not comprise using or obtaining any information about any position of any feature of a function computed using an image (e.g., captured in a video frame obtained using a video camera element of a system according to the disclosed technology) within the said image. According to some example embodiments, determining the time interval (or duration) of blood pressure wave propagation between two points or two areas or two parts of a body according to the disclosed technology does not include using or obtaining any information about any color changes of any area of skin of a subject (e.g., a person) which (changes) are caused by the heartbeats of the subject (including blood pulses or blood waves created by the heartbeats). In some example embodiments, the said determining the duration of the time interval of the blood pulse propagation between the first point and the second point of the subject does not include using or obtaining any information about any distance. In some example embodiments, the said determining the duration of the time interval of the blood pulse propagation between the first point and the second point of the subject does not comprise using or obtaining any information about any change of (or in) skin color of the subject (e.g., a change that is caused by or is related to heartbeats of the subject, including blood (pressure) wave(s) or pulse(s) caused by the heartbeats). In some example embodiments, the instructions and/or computations do not cause the processor or the computer or a computing element to use or obtain any information about any distance. In some example embodiments, the instructions and/or computations do not cause the processor or the computer or a computing element to use or obtain any information about any change of (or in) skin color of the subject (e.g., about a change that is caused by or is related to heartbeats of the subject, including blood (pressure) wave(s) or pulse(s) caused by the heartbeats).

Note that although descriptions of the methods according to the disclosed technology presented in this patent document include listing method steps in a particular order and/or numbering individual method steps (which is done solely for the purpose of convenience of referring to the individual steps of a method), such descriptions do not in any way limit the disclosed technology and any steps of any method according to the technology disclosed in this patent document can be performed (or done or executed) in any order. Moreover, any step of any method according to the disclosed technology can be performed either sequentially or in parallel with (or relative to) any other step or steps of the method or of any other method according to the disclosed technology. Any of the methods according to the disclosed technology can include any additional step or steps. Any step or multiple steps of any method according to the technology disclosed herein can be omitted (e.g., not performed or not executed) from the method. Moreover, any step of any method according to the disclosed technology can be performed by any device or any system or any component of the device or the system (e.g., a computing element of the system or the device) according to the technology disclosed herein. Similarly, any element or any feature of any device or system according to the technology disclosed herein can be used by any other device of system according to the disclosed technology.

LISTING 1

```
#!python3
#Please see picamera.readthedocs.io for the 'picamera' library documentation.
import picamera
import numpy as np
import picamera.array
import time
import datetime
import os
experimentDurationHours = 0.5 #Duration of the ALT data collection, hours.
timeSliceDurationMinutes = 6 #The whole 'experimentDurationHours' time is split into
#'timeSliceDurationMinutes' minutes long intervals ('time
# slices').
experimentDir ="./experiment/" #Location where ALT data, video, etc. will be saved.
# Each 'time slice' has its own sub-folder, see below.
os.makedirs(experimentDir)
class ALT(picamera.array.PiMotionAnalysis):
    def analyse(self, a):
        # This is the "sSAD" value referred to above:
        sSAD = np.sum(a['sad'])
        sSADs.append(sSAD)
        # Note that the sSAD value for an I-frame in the captured video data stream will be
        # equal to zero. Please consult documentation for the
        'start_recording( )' method of
        # the 'picamera.PiCamera' class
        # (picamera.readthedocs.io/en/release-1.12/
        api_camera.html#picamera.PiCamera.start_recording).
        # Particularly, setting the 'intra_period' parameter of the
        istart_recording(y method
        # to zero will cause "the encoder to produce a single initial I-frame,
        and then only
        # P-frames subsequently". If you would like to keep I-frames in
        the captured video
        # stream, you can adjust the 'intra_period' parameter
        accordingly (or leave it at its
        # default value). A way to process the I-frame sSAD values
        would be to replace
        # them with the sSAD value of the previous frame, as the following
        'pseudo code'
        # shows:
        # if sSAD !=0:
        # sSADsNoZeros.append(sSAD)
        # else:
        # if len(sSADsNoZeros) >=1:
        # sSADsNoZeros.append(sSADsNoZeros[-1])
with picamera.PiCamera( ) as camera:
    with ALT(camera) as mvdOutput: #motion vector data (mvd) output
        camera.resolution = (1280, 720)
        camera.framerate = 49
        camera.exposure_mode = 'night'
        camera.awb_mode = 'auto'
        camera.iso = 1600
        camera.sharpness = 100
        camera.contrast = 100
        while camera.analog_gain <=1:
            time.sleep(0.1)
        #'seep' delays below give you some time before the camera parameters are locked
        # and video recording and ALT data collection start
        # which might be helpful, for example, if you start ALT before going to sleep
        # so that there is time for you to turn off the lights and let the camera adjust to
        # low-light environment.
        print('Preparing ...')
        print('60 ...')
        time.sleep(45)
        print('15 ...')
        time.sleep(5)
        # Fixing the camera's video acquisition parameters:
        camera.shutter_speed = camera.exposure_speed
        camera.exposure_mode = 'off'
        g = camera.awb_gains
        camera.awb_mode = 'off'
        camera.awb_gains = g
```

-continued

LISTING 1

```
print('10 ...')
time.sleep(5)
print('5 ...')
time.sleep(5)
print('RUNNING ...')
for t in range(int(experimentDurationHours*60/
timeSliceDurationMinutes)):
startDateTime = datetime.datetime.now( )
timeSliceDir = experimentDir + str(startDateTime) + "T"
print('timeSliceDir = ', timeSliceDir)
os.makedirs(timeSliceDir)
sSADs = [ ]
sSADsfile = open(timeSliceDir + 'SADs.txt', 'w')
# Note that the 'quality' parameter of the 'start_recording
( )' method might be
# useful to keep the size of the captured video files reasonably low.
# Please see
# picamera.readthedocs.io/en/release-1.12/
api_camera.html#picamera.PiCamera.start_recording
# for details.
camera.start_recording(timeSliceDir + '1280x720.h264', format = 'h264',
motion_output = mvdOutput)
camera.wait_recording(timeSliceDurationMinutes*60)
camera.stop_recording( )
# Note that saving ALT data into a file and stopping/restarting video
recording will
# cause a short time 'gap' between the consecutive "time slices"
for i in range(len(sSADs)):
sSADsfile.write(str(i +1) + ":" +str(sSADs[i]) + "\n")
sSADsfile.close( )
```

The invention claimed is:

1. A method of determining a duration of a time interval of a blood pulse propagation between a first point and a second point of a subject, comprising:
   illuminating a first area proximate to the first point and a second area proximate to the second point using a light source;
   obtaining a set of video frames comprising at least a first video frame and a second video frame using a camera; and
   performing computations, using a processor, the computations comprising:
      for each pixel of a first part of the second video frame, calculating a difference between a numeric value associated with the pixel and a numeric value associated with a pixel of a first part of the first video frame;
      for each pixel of the first part of the second video frame, calculating a numeric value using the difference calculated for the pixel;
      obtaining a first numeric value using a sum of the said numeric values calculated for the pixels of the first part of the second video frame;
      for each pixel of a second part of the second video frame, calculating a difference between a numeric value associated with the pixel and a numeric value associated with a pixel of a second part of the first video frame;
      for each pixel of the second part of the second video frame, calculating a numeric value using the difference calculated for the pixel;
      obtaining a second numeric value using a sum of the said numeric values calculated for the pixels of the second part of the second video frame; and
      obtaining the duration of the time interval of the blood pulse propagation between the first point and the second point of the subject using the first numeric value and the second numeric value.

2. The method of claim 1, wherein the said determining the duration of the time interval of the blood pulse propagation between the first point and the second point of the subject does not include using any information about any distance.

3. The method of claim 1, wherein the said determining the duration of the time interval of the blood pulse propagation between the first point and the second point of the subject does not comprise using any information about any change of skin color of the subject caused by heartbeats of the subject.

4. The method of claim 1, wherein the said illuminating the first area and the second area comprises illuminating one or more sub-areas within the first area and illuminating one or more sub-areas within the second area such that any sub-area from the illuminated sub-areas of the first area is at least partially encompassed by a part of the first area having a lower level of illumination compared to illumination of the sub-area from the illuminated sub-areas of the first area and any sub-area from the illuminated sub-areas of the second area is at least partially encompassed by a part of the second area having a lower level of illumination compared to illumination of the sub-area from the illuminated sub-areas of the second area.

5. The method of claim 1, wherein the said illuminating the first area and the second area comprises providing photons from the light source to a sub-area of the first area and refraining from providing photons from the light source to a part of the first area that is proximate to the sub-area of the first area and further comprises providing photons from the light source to a sub-area of the second area and refraining from providing photons from the light source to a part of the second area that is proximate to the sub-area of the second area.

6. The method of claim 1, wherein the light source is configured to provide illumination of a sub-area in the first area that is at least K times higher compared to illumination due to the light source of a part of the first area that is different from the sub-area in the first area and wherein the light source is configured to provide illumination of a sub-area in the second area that is at least M times higher compared to illumination due to the light source of a part of the second area that is different from the sub-area in the second area.

7. The method of claim 6, wherein K is larger than $1+10^{-100}$ and M is larger than $1+10^{-100}$.

8. The method of claim 1, wherein the said numeric value calculated for a pixel of the first part of the second video frame using the difference calculated for the pixel is equal to at least one of: an absolute value of the difference calculated for the pixel or a squared value of the difference calculated for the pixel, and wherein the said numeric value calculated for a pixel of the second part of the second video frame using the difference calculated for the pixel is equal to at least one of: an absolute value of the difference calculated for the pixel or a squared value of the difference calculated for the pixel.

9. A system for determining a duration of a time interval of a blood pressure wave propagation between a first point and a second point of a subject, comprising:
   a light source configured to illuminate a first area proximate to the first point and a second area proximate to the second point;

a camera configured to obtain a set of video frames comprising at least a first video frame and a second video frame; and a processor and a non-transient processor-readable storage medium storing one or more instructions which, when executed by the processor, cause the processor to:

for each pixel of a first part of the second video frame, calculate a difference between a numeric value associated with the pixel and a numeric value associated with a pixel of a first part of the first video frame;

for each pixel of the first part of the second video frame, calculate a numeric value using the difference calculated for the pixel;

obtain a first numeric value using a sum of the said numeric values calculated for the pixels of the first part of the second video frame;

for each pixel of a second part of the second video frame, calculate a difference between a numeric value associated with the pixel and a numeric value associated with a pixel of a second part of the first video frame;

for each pixel of the second part of the second video frame, calculate a numeric value using the difference calculated for the pixel;

obtain a second numeric value using a sum of the said numeric values calculated for the pixels of the second part of the second video frame; and obtain the duration of the time interval of the blood pressure wave propagation between the first point and the second point of the subject using the first numeric value and the second numeric value.

10. The system of claim 9, wherein the instructions do not cause the processor to use any information about any distance.

11. The system of claim 9, wherein the instructions do not cause the processor to use any information about any change of skin color of the subject caused by heartbeats of the subject.

12. The system of claim 9, wherein the light source is an infrared light source.

13. The system of claim 9, wherein the camera is an infrared camera.

14. The system of claim 9, wherein the said light source is configured to illuminate the first area by creating a first light spot on the first area, wherein the first light spot has an illumination due to the light source which is higher than an illumination produced by the light source on a part of the first area which is proximate to the first light spot, and wherein the said light source is configured to illuminate the second area by creating a second light spot on the second area, wherein the second light spot has an illumination due to the light source which is higher than an illumination produced by the light source on a part of the second area proximate to the second light spot.

15. The system of claim 9, wherein the light source is configured to illuminate the first area by creating light spots on the first area, wherein the light spots on the first area are separated from each other by regions of the first area having lower illumination due to the light source compared to that of the light spots, and wherein the light source is configured to illuminate the second area by creating light spots on the second area, wherein the light spots on the second area are separated from each other by regions of the second area having lower illumination due to the light source compared to that of the light spots.

16. The system of claim 9, wherein the said light source is configured to illuminate the first area and the second area by producing light spots on the first area and the second area, wherein at least a first light spot and a second light spot among the light spots on the first area are such that an illumination maximum of the first light spot is separated from an illumination maximum of the second light spot by at least 1 nm distance and wherein at least a third light spot and a fourth light spot among the light spots on the second area are such that an illumination maximum of the third light spot is separated from an illumination maximum of the fourth light spot by at least 1 nm distance.

17. The system of claim 9, wherein the said light source is configured to illuminate the first area and the second area by creating light spots on the first area and the second area, and wherein the said light source is capable of changing at least one of: a distance at least between two of the said light spots on the first area or a distance at least between two of the said light spots on the second area, a size of at least one of the said light spots, a shape of at least one of the said light spots, or illumination intensity of at least one of the said light spots.

18. A non-transient computer-readable storage medium storing instructions that, when executed by one or more processors, cause the one or more processors to:

cause a light source to illuminate a first area proximate to a first point of a subject and a second area proximate to a second point of the subject;

cause a camera to obtain a set of video frames comprising at least a first video frame and a second video frame; and perform computations comprising:

for each pixel of a first part of the second video frame, calculate a difference between a numeric value associated with the pixel and a numeric value associated with a pixel of a first part of the first video frame;

for each pixel of the first part of the second video frame, calculate a numeric value using the difference calculated for the pixel;

obtain a first numeric value using a sum of the said numeric values calculated for the pixels of the first part of the second video frame;

for each pixel of a second part of the second video frame, calculate a difference between a numeric value associated with the pixel and a numeric value associated with a pixel of a second part of the first video frame;

for each pixel of the second part of the second video frame, calculate a numeric value using the difference calculated for the pixel;

obtain a second numeric value using a sum of the said numeric values calculated for the pixels of the second part of the second video frame; and obtain a length of a time interval of a blood pressure wave propagation between the first point and the second point of the subject using the first numeric value and the second numeric value.

19. The non-transient computer-readable storage medium of claim 18, wherein the instructions do not cause the one or more processors to use any information about any distance.

20. The non-transient computer-readable storage medium of claim 18, wherein the instructions do not cause the one or more processors to use any information about any change of skin color of the subject caused by heartbeats of the subject.

* * * * *